(12) United States Patent
Inoue et al.

(10) Patent No.: US 8,512,880 B2
(45) Date of Patent: Aug. 20, 2013

(54) ORGANOMETALLIC COMPLEX, AND LIGHT-EMITTING ELEMENT AND LIGHT-EMITTING DEVICE USING THE ORGANOMETALLIC COMPLEX

(75) Inventors: Hideko Inoue, Atsugi (JP); Satoshi Seo, Kawasaki (JP); Nobuharu Ohsawa, Zama (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 117 days.

(21) Appl. No.: 12/878,049

(22) Filed: Sep. 9, 2010

(65) Prior Publication Data

US 2011/0001133 A1 Jan. 6, 2011

Related U.S. Application Data

(62) Division of application No. 11/791,832, filed as application No. PCT/JP2005/022593 on Dec. 1, 2005, now Pat. No. 7,795,429.

(30) Foreign Application Priority Data

Dec. 3, 2004 (JP) ................................ 2004-351770

(51) Int. Cl.
*H01L 51/54* (2006.01)

(52) U.S. Cl.
USPC ........... 428/690; 428/917; 313/504; 313/506; 257/E51.044

(58) Field of Classification Search
None
See application file for complete search history.

(56) References Cited

U.S. PATENT DOCUMENTS

| | | | |
|---|---|---|---|
| 6,303,238 B1 | 10/2001 | Thompson et al. | |
| 6,821,645 B2 | 11/2004 | Igarashi et al. | |
| 6,821,646 B2 | 11/2004 | Tsuboyama et al. | |
| 6,835,469 B2 | 12/2004 | Kwong et al. | |
| 6,911,271 B1 | 6/2005 | Lamansky et al. | |
| 6,939,624 B2 | 9/2005 | Lamansky et al. | |
| 6,953,628 B2 | 10/2005 | Kamatani et al. | |
| 7,094,477 B2 | 8/2006 | Kamatani et al. | |
| 7,147,935 B2 | 12/2006 | Kamatani et al. | |
| 7,220,495 B2 | 5/2007 | Tsuboyama et al. | |
| 7,238,437 B2 | 7/2007 | Igarashi et al. | |
| 7,238,806 B2 | 7/2007 | Inoue et al. | |
| 7,339,317 B2 | 3/2008 | Yamazaki | |
| 7,381,479 B2 | 6/2008 | Lamansky et al. | |
| 7,400,087 B2 | 7/2008 | Yamazaki | |
| 7,413,816 B2 | 8/2008 | Inoue et al. | |
| 7,553,560 B2 | 6/2009 | Lamansky et al. | |
| 7,771,844 B2 | 8/2010 | Inoue et al. | |
| 2003/0218418 A9 * | 11/2003 | Sato et al. | 313/504 |
| 2005/0191527 A1 | 9/2005 | Fujii et al. | |
| 2007/0213527 A1 | 9/2007 | Inoue et al. | |
| 2007/0241667 A1 | 10/2007 | Ohsawa et al. | |
| 2008/0113216 A1 | 5/2008 | Inoue et al. | |
| 2010/0044689 A1 * | 2/2010 | Nishimura et al. | 257/40 |

FOREIGN PATENT DOCUMENTS

| | | |
|---|---|---|
| EP | 1 191 612 | 3/2002 |
| EP | 1 348 711 | 10/2003 |
| EP | 1 349 435 | 10/2003 |
| EP | 1 574 514 | 9/2005 |
| EP | 1 690 866 | 8/2006 |
| JP | 63-159856 | 7/1988 |
| JP | 06-207169 | 7/1994 |

(Continued)

OTHER PUBLICATIONS

Yamamoto et al., "Preparation of New Electron-Accepting π-Conjugated Polyquinoxalines. Chemical and Electrochemical Reduction, Electrically Conducting Properties, and Use in Light-Emitting Diodes," Journal of the American Chemical society, vol. 118, No. 16, pp. 3930-3937, 1996.

International Search Report (Application No. PCT/JP2005/022593) dated Mar. 14, 2006.

Written Opinion (Application No. PCT/JP2005/022593) dated Mar. 14, 2006.

Tsutsui et al., "Electroluminescence in Organic Thin Films," Photochemical Processes in Organized Molecular Systems, 1991, pp. 437-450.

(Continued)

*Primary Examiner* — Marie R. Yamnitzky
(74) *Attorney, Agent, or Firm* — Eric J. Robinson; Robinson Intellectual Property Law Office, P.C.

(57) ABSTRACT

A material which can emit phosphorescence is disclosed. Further, a light-emitting element having good chromaticity is disclosed. An embodiment of the present invention is an organometallic complex including a structure as represented by the general formula (1): wherein $R_1$ represents an alkyl group having 1 to 4 carbon atoms; each of $R_2$ to $R_5$ represents any one of hydrogen, a halogen element, an acyl group, an alkyl group, an alkoxyl group, an aryl group, a cyano group, and a heterocyclic group; Ar represents an aryl group or a heterocyclic group, preferably, an aryl group having an electron withdrawing group or a heterocyclic group having an electron withdrawing group; and M represents a Group 9 element or a Group 10 element. By virtue that the Ar has an electron withdrawing group, an organometallic complex which emits phosphorescence with higher emission intensity can be obtained.

Formula 1

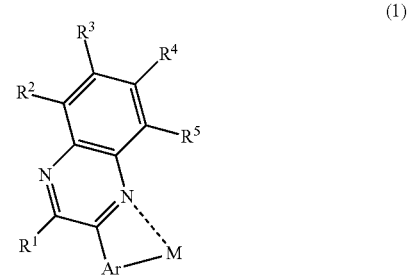

(1)

32 Claims, 42 Drawing Sheets

(56) References Cited

FOREIGN PATENT DOCUMENTS

| | | |
|---|---|---|
| JP | 2001-247859 | 9/2001 |
| JP | 2003-040873 | 2/2003 |
| JP | 2003-058473 | 2/2003 |
| JP | 2004-155728 | 6/2004 |
| JP | 2005-506361 | 3/2005 |
| JP | 2005-239648 | 9/2005 |
| JP | 2006-073992 | 3/2006 |
| JP | 2006-182775 | 7/2006 |
| JP | 3810789 | 8/2006 |
| WO | WO 00/70655 | 11/2000 |
| WO | WO 01/41512 | 6/2001 |
| WO | WO 02/15645 | 2/2002 |
| WO | WO 02/45466 | 6/2002 |
| WO | WO 03/033617 | 4/2003 |
| WO | WO 2004/056839 | 7/2004 |
| WO | WO 2005/054261 | 6/2005 |
| WO | WO 2005/115061 | 12/2005 |

OTHER PUBLICATIONS

Baldo et al., "Highly Efficient Phosphorescent Emission From Organic Electroluminescent Devices," Nature, Sep. 10, 1998, vol. 395, pp. 151-154.

Baldo et al., "Very High-Efficiency Green Organic Light-Emitting Devices Based on Electrophosphorescence," Appl. Phys. Lett. (Applied Physics Letters), Jul. 5, 1999, vol. 75, No. 1, pp. 4-6.

Tsutsui et al., "High Quantum Efficiency in Organic Light-Emitting Devices with Iridium-Complex as a Triplet Emissive Center," Jpn. J. Appl. Phys. (Japanese Journal of Applied Physics), Dec. 15, 1999, vol. 38/Part 2, No. 12b, pp. L1502-L1504.

O'Brien et al., "Improved Energy Transfer in Electrophosphorescent Devices," Appl. Phys. Lett. (Applied Physics Letters), Jan. 18, 1999, vol. 74, No. 3, pp. 442-444.

Baldo et al., "High-Efficiency Fluorescent Organic Light-Emitting Devices Using a Phosphorescent Sensitizer," Nature, Feb. 17, 2000, vol. 403, pp. 750-753.

Tsutsui, "Mechanism of Organic EL Element and Luminous Efficiency," Textbook of the 3$^{rd}$ Seminar at Division of Organic Molecular Electronics and Bioelectronics, 1993, pp. 31-37, The Japan Society of Applied Physics.

Nishi et al., "High Efficiency TFT-OLED Display with Iridium-Complex as Triplet Emissive Center," Proceedings of the 10$^{th}$ International Workshop on Inorganic and Organic Electroluminescence (EL'00), Dec. 4, 2000, pp. 353-356.

Tang et al., "Organic Electroluminescent Diodes," Appl. Phys. Lett. (Applied Physics Letters), Sep. 21, 1987, vol. 51, No. 12, pp. 913-915.

Thompson et al., "Phosphorescent Materials and Devices," Proceedings of the 10$^{th}$ International Workshop on Inorganic and Organic Electroluminescence (EL'00), Dec. 4, 2000, pp. 35-38.

Duan et al., "New Iridium Complexes as Highly Efficient Orange-Red Emitters in Organic Light-Emitting Diodes," Adv. Mater. (Advanced Materials), Feb. 5, 2003, vol. 15, No. 3, pp. 224-228.

Fujii et al., "04-O Efficient Red Organometallic Phosphors Bearing 2,3-Diphenylquinoxalines and their Application to Electrophosphorescent Diodes," Korea-Japan Joint Forum, Organic Materials for Electronics and Photonics, Nov. 3, 2004.

Kulikova et al., "Effects of the Nature of the Ligand Environment and Metal Center on the Optical and Electrochemical Properties of Platinum ( II ) and Palladium ( II ) Ethylenediamine Complexes with Heterocyclic Cyclometalated Ligands ," Russian Journal of General Chemistry, 2000, vol. 70, No. 2, pp. 163-170.

Steel et al., "Cyclometallated compounds V. Double cyclopalladation of diphenyl pyrazines and related ligands," Journal of Organometallic Chemistry, 1990, vol. 395, No. 3, pp. 359-373.

Balashev et al., "Synthesis and Properties of Palladium ( II ) and Platinum ( II ) (2,3-diphenylquinoxalinato-C,N) ethylenediamine Complexes," Russian Journal of General Chemistry, Aug. 1, 1999, vol. 69, No. 8, pp. 1348-1349.

Rasmussen et al., "Synthesis and Characterization of a Series of Novel Rhodium and Iridium Complexes Containing Polypyridyl Bridging Ligands: Potential Uses in the Development of Multimetal Catalysts for Carbon Dioxide Reduction," Inorg. Chem. (Inorganic Chemistry), 1990, vol. 29, No. 20, pp. 3926-3932.

Zhang et al., "Synthesis and Photoluminescence of a New Red Phosphorescent Iridium(III) Quinoxaline Complex," Chinese Chemical Letters, 2004, vol. 15, No. 11, pp. 1349-1352.

Seo et al., "P-132: Long-Lived Deeply Red Phosphorescent OLEDs Based on Electrochemically Stable Ir Complexes," SID Digest '05 : SID International Symposium Digest of Technical Papers, 2005, vol. 36, pp. 806-809.

Fujii et al., "Highly Efficient and Vivid-Red Phosphors Bearing 2,3-Diphenylquinoxaline Units and their Application to Organic Light-Emitting Devices," IEICE Trans. Electron. (IEICE Transactions on Electronics), Dec. 1, 2004, vol. E87-C, No. 12, pp. 2119-2121.

International Search Report (Application No. PCT/JP2004/018079) dated Apr. 5, 2005.

Written Opinion (Application No. PCT/JP2004/018079) dated Apr. 5, 2005.

Lewis, Hawley's Condensed Chemical Dictionary, vol. Twelfth Edition, p. 594, Van Nostrand Reinhold, (1993).

Jakubke et al., Concise Encyclopedia Chemistry, p. 490, Walter De Gruyter, (1993).

Ito et al., "Asymmetric Synthesis of Helical Poly(Quinoxaline-2, 3-Diyl)S by Palladium-Mediated Polymerization of 1, 2-Diisocyanobenzenes: Effective Control of the Screw-Sense by a Binaphthyl Group at the Chain-End," J. Am. Chem. Soc. (Journal of the American Chemical Society), 1998, vol. 120, pp. 11880-11893.

Ito et al., "Living Polymerization of 1, 2-Diisocyanoarenes Promoted by (Quinoxalinyl)Nickel Complexes," Polymer Journal, 1992, vol. 24, No. 3, pp. 297-299.

International Search Report (Application No. PCT/JP2005/009310) dated Aug. 30, 2005.

Written Opinion (Application No. PCT/JP2005/009310) dated Aug. 30, 2005.

International Search Report (Application No. PCT/JP2005/022507) dated Feb. 21, 2006.

Written Opinion (Application No. PCT/JP2005/022507) dated Feb. 21, 2006.

European Search Report (Application No. 04799935.4) dated Jan. 23, 2009.

Brooks et al., "Synthesis and Characterization of Phosphorescent Cyclometalated Platinum Complexes," Inorg. Chem. (Inorganic Chemistry), 2002, vol. 41, No. 12, pp. 3055-3066.

Parker, Mcgraw-Hill Dictionary of Chemical Terms, Jan. 1, 1985, vol. 3$^{rd}$ Ed, p. 200, Mcgraw-Hill.

Patani et al., "Bioisosterism: A Rational Approach in Drug Design," 1996, Chem. Rev., 96, No. 8, 3147-3176.

* cited by examiner

ORGANOMETALLIC COMPLEX, AND LIGHT-EMITTING ELEMENT AND LIGHT-EMITTING DEVICE USING THE ORGANOMETALLIC COMPLEX

TECHNICAL FIELD

The present invention relates to a material which can emit Light by current excitation, and more particularly such an organometallic complex which emits light by current excitation. Further, the present invention relates to a light-emitting element and a light-emitting device, each of which uses the material.

BACKGROUND ART

A light-emitting element including a layer containing a light-emitting material between a pair of electrodes is used as a pixel, a light source, or the like and is provided in a light-emitting device such as a display device or a lighting device. Upon applying current between the pair of electrodes of the light-emitting element, an excited light-emitting material emits fluorescence or phosphorescence.

In theory, internal quantum efficiency of phosphorescence is three times as large as that of fluorescence in the case of current excitation by comparing phosphorescence with fluorescence. Therefore, it is considered that luminous efficiency is increased by using a light-emitting material which emits phosphorescence instead of using a light-emitting material which emits fluorescence, and so a material which emit phosphorescence has been developed.

For example, a patent document 1 discloses a metal complex having iridium as its central metal. In accordance with the patent document 1, the metal complex can be used as a light-emitting material.

Patent document 1: Unexamined patent publication No. 2001-247859

DISCLOSURE OF INVENTION

It is an object of the present invention to provide a material which can emit phosphorescence. It is another object of the present invention to provide a light-emitting element with good chromaticity.

As a result of painstaking research by the present inventors, it can be found that an organometallic complex including a structure as represented by general formulae (1) or (2) can emit phosphorescence. Further, an organometallic complex as represented by general formula (3) or (4) can emit phosphorescence.

An embodiment of the present invention is an organometallic complex including a structure as represented by the general formula (1):

Formula 1

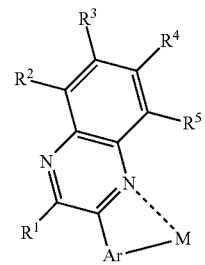

(1)

wherein $R^1$ represents an alkyl group having 1 to 4 carbon atoms; each of $R^2$ to $R^5$ represents any one of hydrogen, a halogen element, an acyl group, an alkyl group, an alkoxyl group, an aryl group, a cyano group, and a heterocyclic group; Ar represents an aryl group or heterocyclic group; and M represents a Group 9 element or a Group 10 element. By virtue that the Ar has an electron-withdrawing group, an organometallic complex which emits phosphorescence with higher emission intensity can be obtained.

An embodiment of the present invention is an organometallic complex including a stucture as represented by the general formula (2):

Formula 2

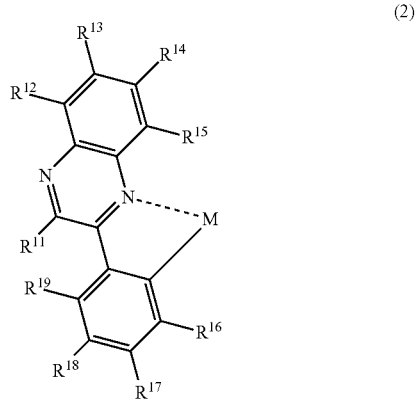

(2)

wherein $R^{11}$ represents an alkyl group having 1 to 4 carbon atoms; each of $R^{12}$ to $R^{15}$ represents any one of hydrogen, a halogen element, an acyl group, an alkyl group, an alkoxyl group, an aryl group, a cyano group, and a heterocyclic group; each of $R^{16}$ to $R^{19}$ represents any one of hydrogen, an acyl group, an alkyl group, an alkoxyl group, an aryl group, a heterocyclic group, and an electron withdrawing group; and M represents a Group 9 element or a Group 10 element. By virtue that $R^{16}$ to $R^{19}$ have individually an electron withdrawing group, an organometallic complex which emits phosphorescence with higher emission intensity can be obtained.

An embodiment of the present invention is an organometallic complex including a structure as represented by the general formula (3):

Formula 3

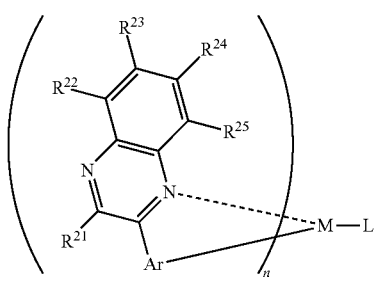

wherein $R^{21}$ represents an alkyl group having 1 to 4 carbon atoms; each of $R^{22}$ to $R^{25}$ represents any one of hydrogen, a halogen element, an acyl group, an alkyl group, an alkoxyl group, an aryl group, a cyano group, and a heterocyclic group; Ar represents an aryl group or a heterocyclic group; and M represents a Group 9 element or a Group 10 element, in which n=2 when M represents a Group 9 element whereas n=1 when M represents a Group 10 element; and L represents a monoanionic ligand having a beta-diketone structure, or a monoanionic bidentate chelate ligand having a carboxyl group, or a monoanionic bidentate chelate ligand having a phenolic hydroxyl group. By virtue that the Ar has an electron withdrawing group, an organometallic complex which emits phosphorescence with higher emission intensity can be obtained.

An embodiment of the present invention is an organometallic complex including a structure as represented by the general formula (4):

Formula 4

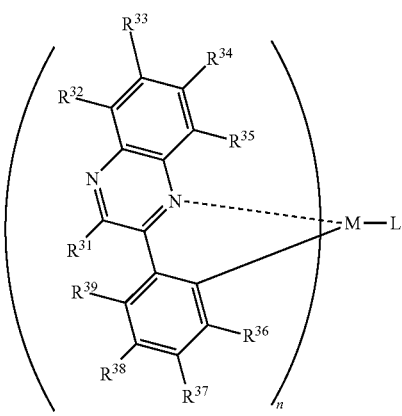

wherein $R^{31}$ represents an alkyl group having 1 to 4 carbon atoms; each of $R^{32}$ to $R^{35}$ represents any one of hydrogen, a halogen element, an acyl group, an alkyl group, an alkoxyl group, an aryl group, a cyano group, and a heterocyclic group; each of $R^{36}$ to $R^{39}$ represents any one of hydrogen, an acyl group, an alkyl group, an alkoxyl group, an aryl group, a heterocyclic group, and an electron withdrawing group; M represents a Group 9 element or a Group 10 element, in which n=2 in the case that M represents a Group element whereas n=1 in the case that M represents a Group 10 element; and L represents a monoanionic ligand having a beta-diketone structure, or a monoanionic bidentate chelate ligand having a carboxyl group, or a monoanionic bidentate chelate ligand having a phenolic hydroxyl group. By virtue that $R^{36}$ to $R^{39}$ have individually an electron withdrawing group, an organometallic complex which emits phosphorescence with higher emission intensity can be obtained.

In the organometallic complex having a structure represented by the general formula (1) or (2), and the organometallic complex represented by the general formula (3) or (4), the electron withdrawing group is preferably a halogen group, a haloalkyl group, or a cyano group. Accordingly, chromaticity and quantum efficiency of the organometallic complex are improved. Further, a fluoro group is preferably in particular among halogen groups and a trifluoromethyl group is preferably in particular among haloalkyl groups. Accordingly, electrons can be trapped efficiently.

In the organometallic complex having a structure represented by the general formula (1) or (2), and the organometallic complex represented by the general formula (3) or (4), a central metal M is preferably heavy metal, more preferably, iridium or platinum. Accordingly, a heavy atom effect can be obtained.

In the organometallic complex represented by the general formula (3) or (4), L is preferably a monoanionic ligand in particular represented by structural formulae (5) to (11). Monoanionic chelate ligands represented by structural formulae (5) to (11) are useful since they have high coordinative ability and are inexpensive.

Structural Formulae 5 to 11

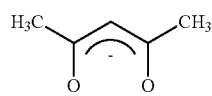

(5)

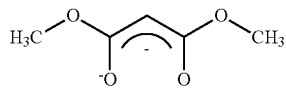

(6)

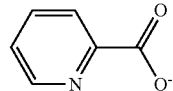

(7)

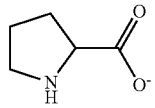

(8)

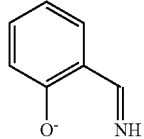

(9)

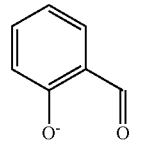

(10)

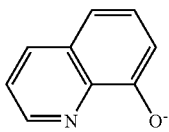

(11)

An embodiment of the present invention is an organometallic complex having a structure represented by the general formula (1) or (2), and a light-emitting element having an organometallic complex represented by the general formula (3) or (4).

An embodiment of the present invention is an organometallic complex having a structure represented by the general formula (1) or (2), and a light-emitting device including a light-emitting element having an organometallic complex represented by the general formula (3) or (4).

According to the present invention, an organometallic complex which can emit phosphorescence can be obtained. According to the present invention, an organometallic complex which can be used as a light-emitting material or a sensitizer can be obtained.

By using the organometallic complex according to the present invention as a light-emitting material, a light-emitting element which can exhibit reddish emission with good chromaticity can be obtained. By using the organometallic complex according to the present invention as a sensitizer, a light-emitting element which can emit light efficiently can be obtained.

These and other objects, features and advantages of the present invention will become more apparent upon reading of the following detailed description along with the accompanied drawings.

Figure 1:
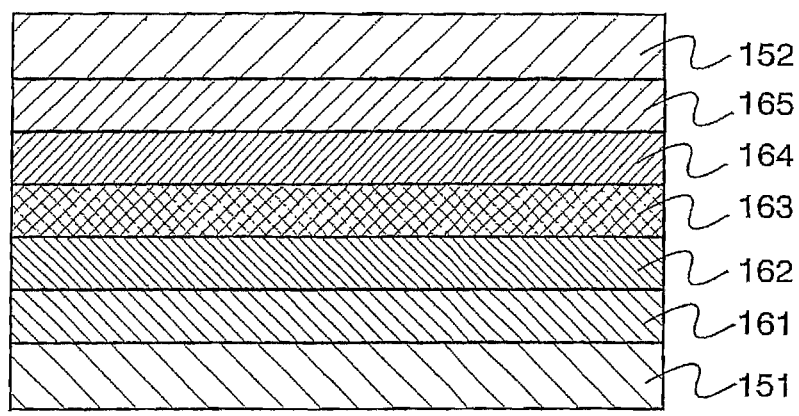
FIG. 1 is an explanatory view for showing a light-emitting element according to the present invention.

BEST MODE FOR CARRYING OUT THE INVENTION
Embodiment 1
As one of embodiments according to the present invention, an organometallic complex as represented by structural formulae 12 to 39 can be nominated. The present invention is not limited to the one described here.
formula 6
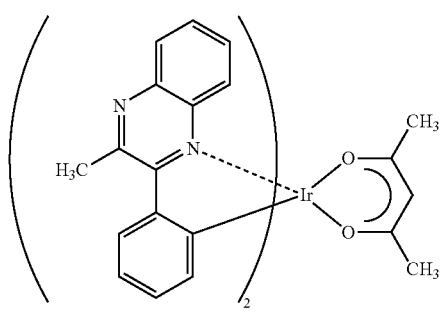
(12)
formula 7
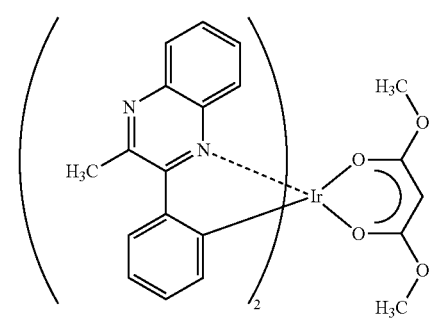
(13)
formula 8
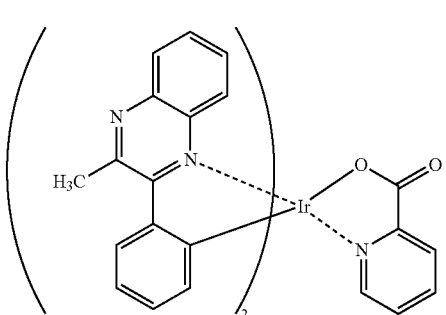
(14)
formula 9
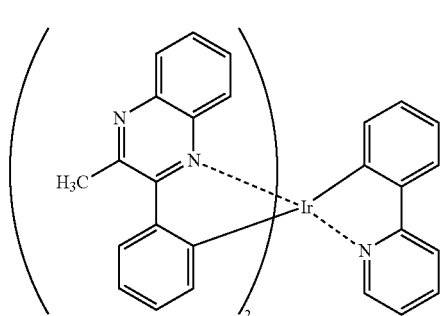
(15)
formula 10
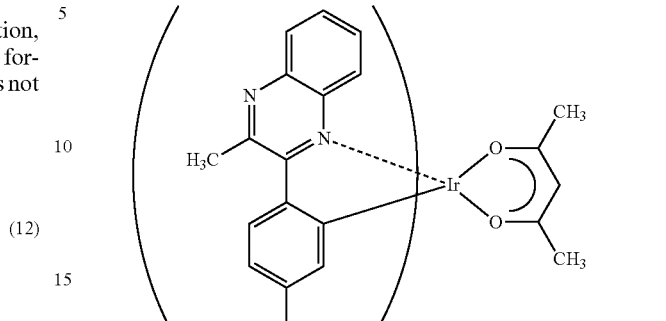
(16)
formula 11
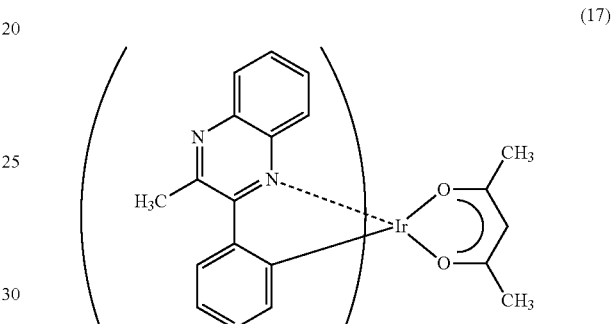
(17)
formula 12
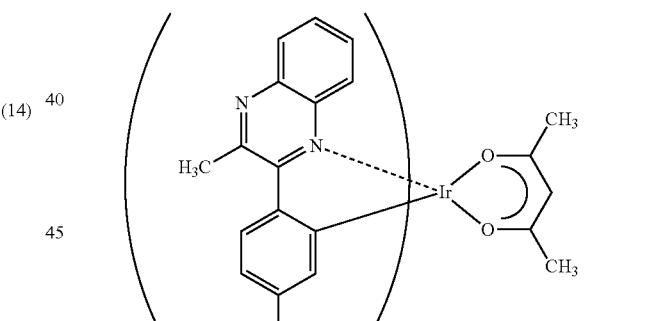
(18)
formula 13
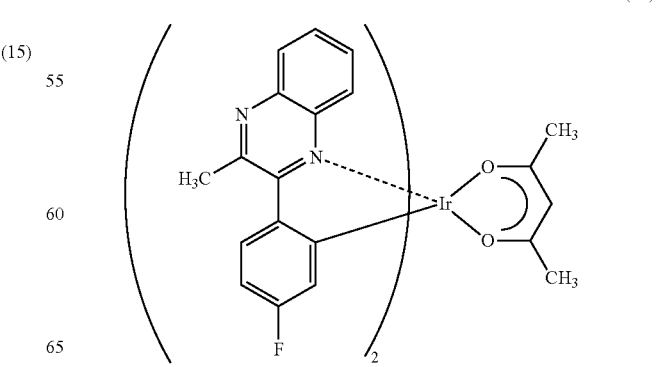
(19)

-continued
formula 14 (20)
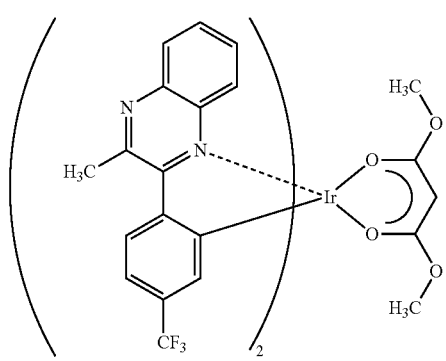
formula 15 (21)
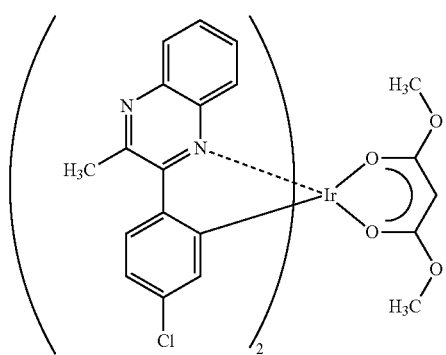
formula 16 (22)
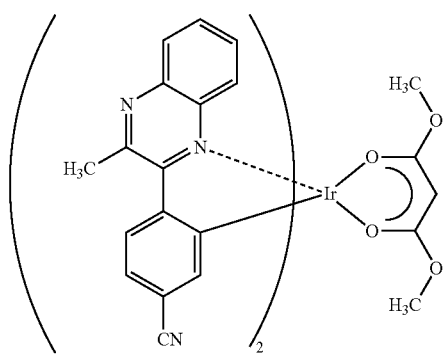
formula 17 (23)
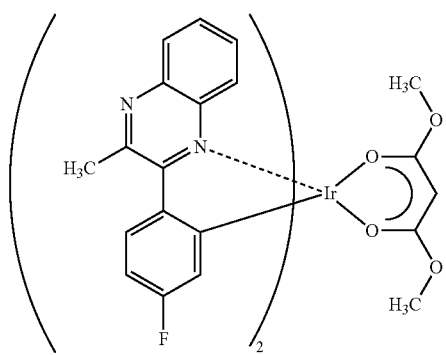
-continued
formula 18 (24)
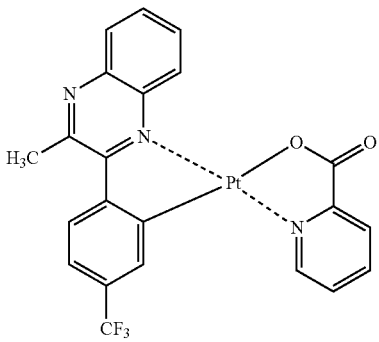
formula 19 (25)
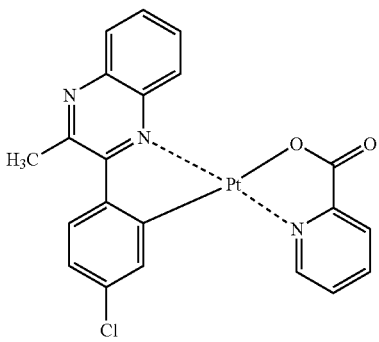
formula 20 (26)
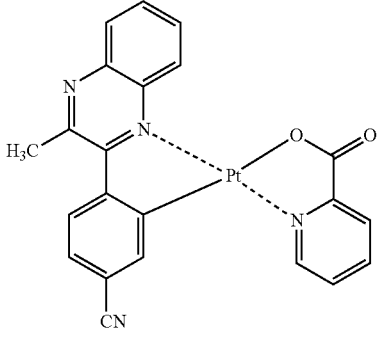
formula 21 (27)
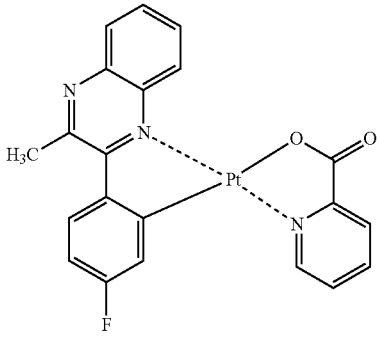

-continued
formula 22
(28)
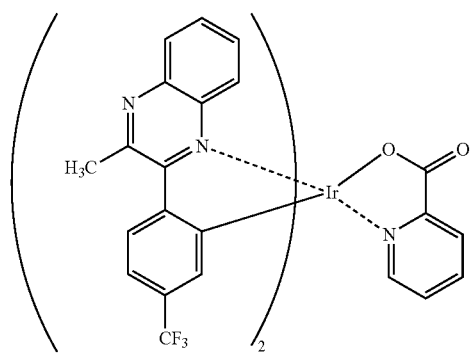
formula 23
(29)
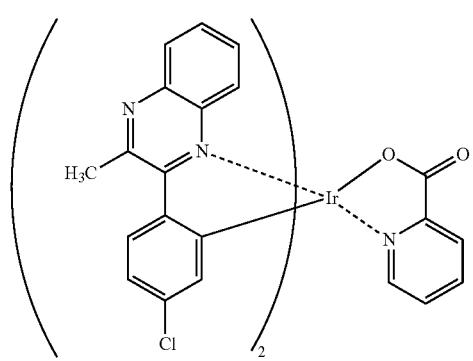
formula 24
(30)
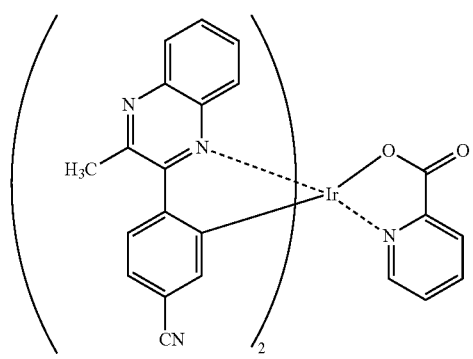
formula 25
(31)
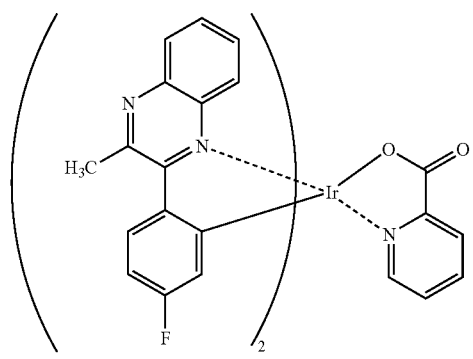
-continued
formula 26
(32)
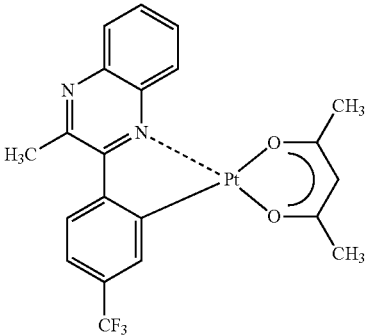
formula 27
(33)
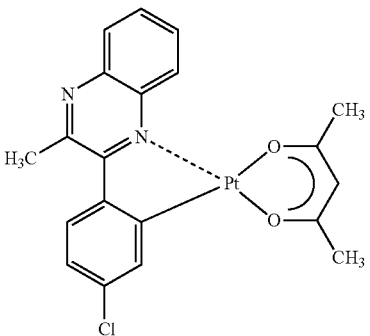
formula 28
(34)
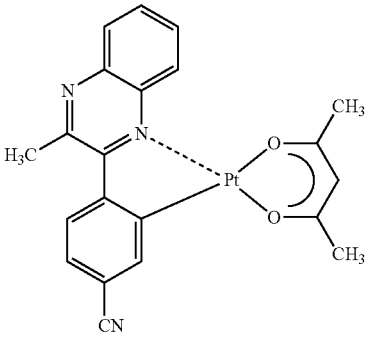
formula 29
(35)
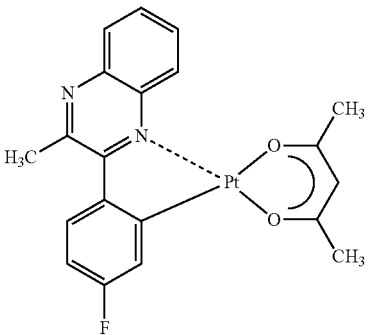

formula 30
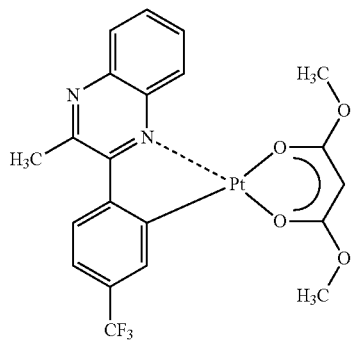
(36)
formula 31
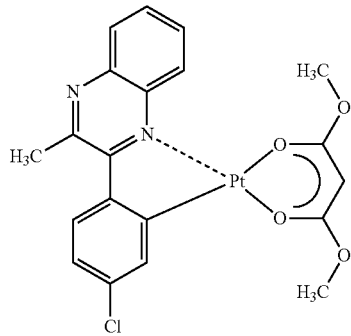
(37)
formula 32
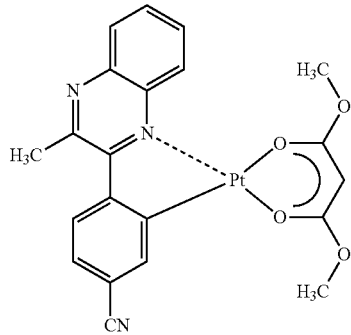
(38)
formula 33
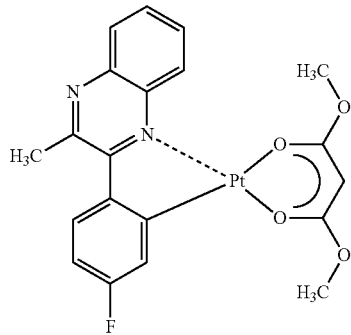
(39)
formula 34
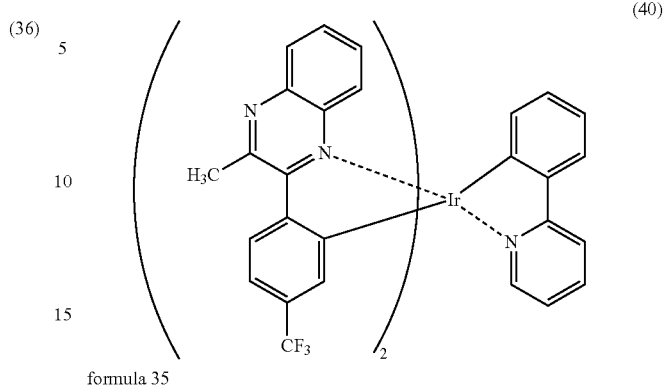
(40)
formula 35
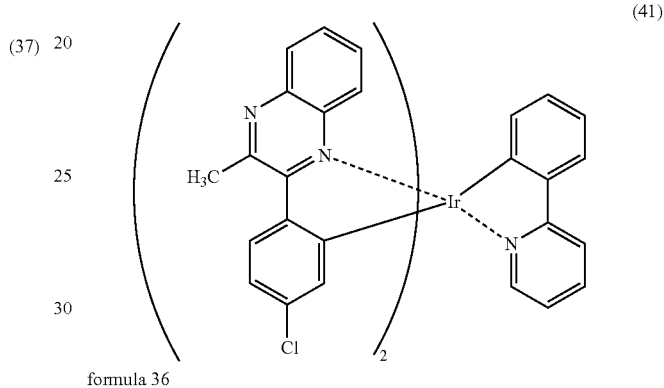
(41)
formula 36
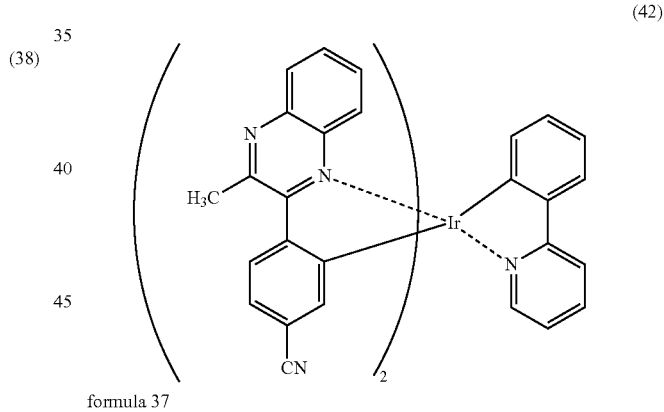
(42)
formula 37
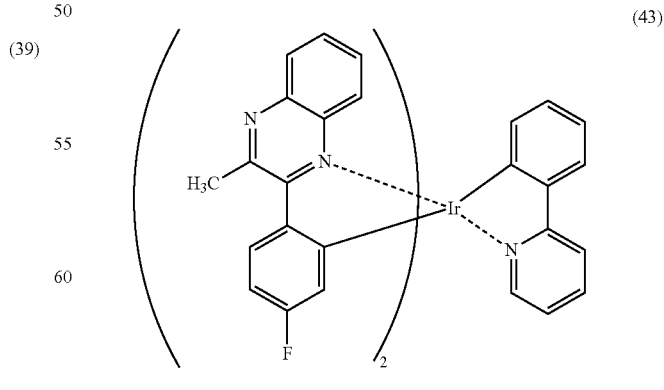
(43)
The organometallic complex according to the present invention as noted above can emit phosphorescence. Further, the organometallic complex according to the present invention can be applied to a light-emitting element as a light-emitting material. The organometallic complex according to the present invention can be applied to a light-emitting element as a photosensitizer.

Embodiment 2

An organometallic complex according to the present invention can be obtained by coordinating a compound represented by the following general formula (44) with a metal atom by an ortho metalation reaction. A mode of a synthesis method of the organometallic complex according to the present invention is explained hereinafter. The synthesis method of the organometallic complex according to the present invention is not limited to that represented by the general formula (44).

Formula 38

(44)

Formula 39

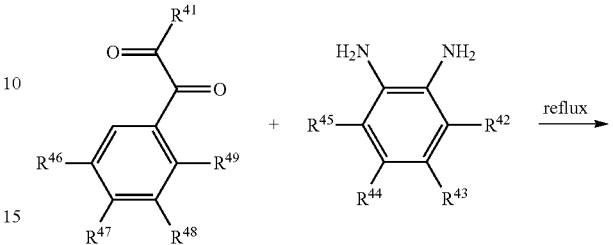

(a-1)

Firstly, a compound including 1-phenyl-1,2-propanedione in its skeleton is reacted with a compound including 1,2-phenylenediamine in its skeleton according to a synthesis scheme (a-1) to synthesize a compound A including 2-methyl-3-phenylquinoxaline in its skeleton.

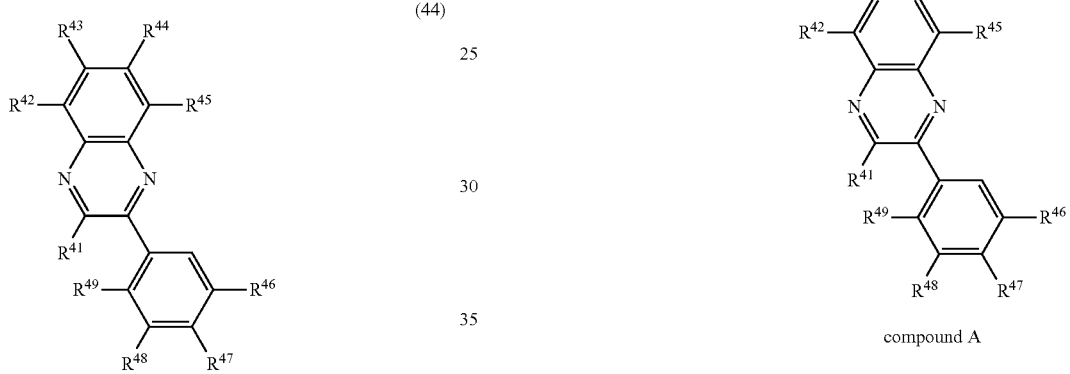

compound A

The compound A is reacted with hydrate of iridium chloride according to a synthesis scheme (a-2) to synthesize a compound B having a structure in which the compound A is coordinated with iridium. The compound B of a chloride bridge is also referred to as a binuclear complex. The reaction according to the synthesis scheme (a-2) is referred to as ortho metalation reaction.

Formula 40

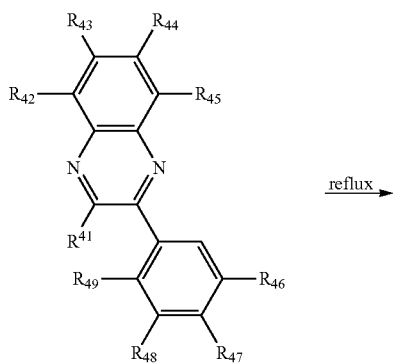

(a-2)

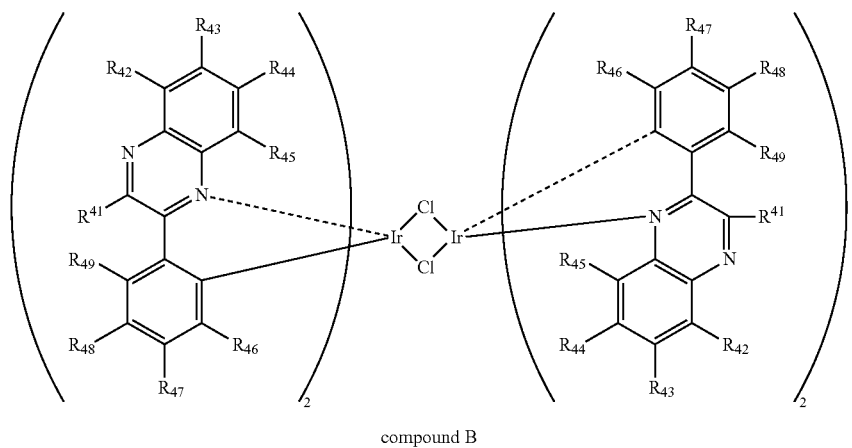
compound B
In the compound B, a monoanionic compound is coordinated with iridium according to a synthesis scheme (a-3), accordingly, an organometallic complex according to the present invention can be obtained as represented by a general formula 45.
Formula 41
(a-3)
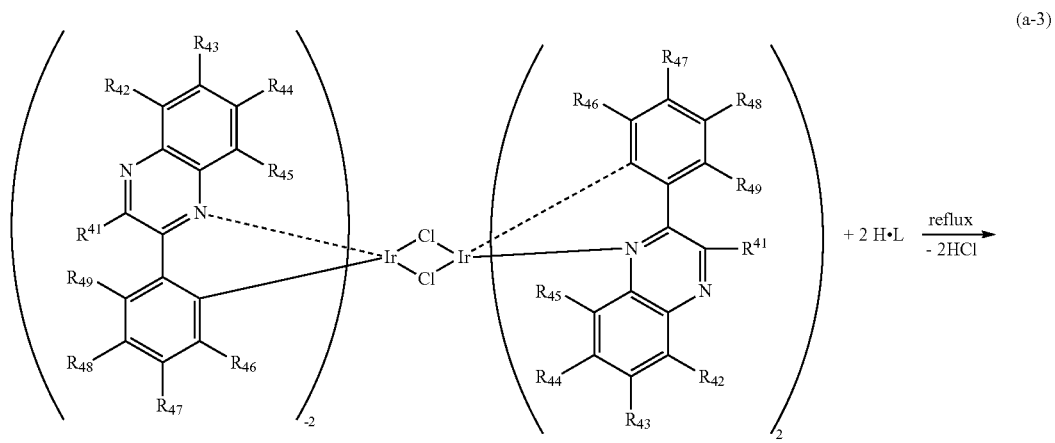
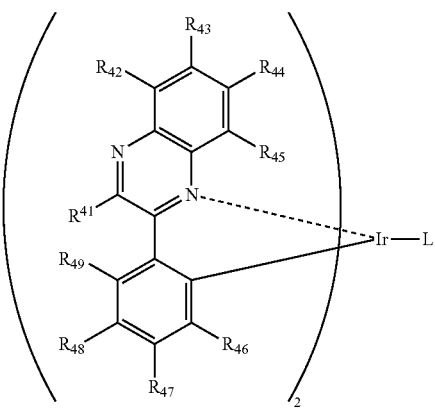

Formula 42

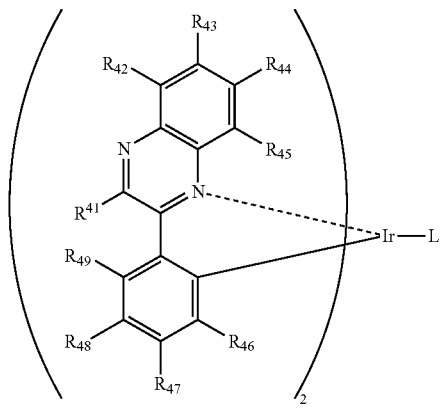

(45)

In the foregoing synthesis schemes (a-1), (a-2), and (a-3), and general formulae (44) and (45), $R^{41}$ is preferably an alkyl group having 1 to 4 carbon atoms. By employing the alkyl group having 1 to 4 carbon atoms for the $R^{41}$ instead of employing hydrogen, the compound B generated in the synthesis scheme (a-2) can be prevented from degradation during the reaction according to the synthesis scheme (a-3). By preventing the degradation of the compound B, the organometallic complex according to the present invention can be obtained. $R^{42}$ to $R^{45}$ are individually hydrogen, a halogen element, an acyl group, an alkyl group, an alkoxyl group, an aryl group, a cyano group, a heterocyclic group, and an electron withdrawing group. $R^{46}$ to $R^{49}$ are individually hydrogen, a halogen element, an acyl group, an alkyl group, alkoxyl group, an aryl group, a heterocyclic group, and an electron withdrawing group. There is especially no limitation on the monoanionic compound; however, a compound represented by any one of structural formulae (5) to (11) is preferably used as the monoanionic compound.

In the organometallic complex represented by the general formula (45), the monoanionic compound coordinated with iridium can be further substituted by a compound represented by the general formula (44) and the organometallic complex according to the present invention can be obtained as represented by a general formula 46.

Formula 43

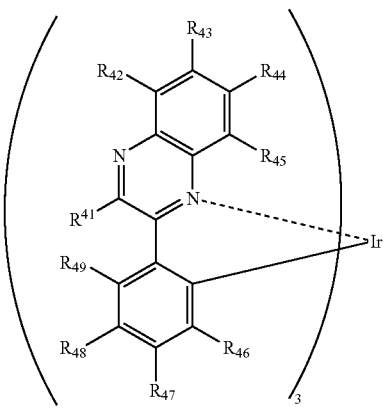

(46)

In addition, hydrate of iridium chloride can be used instead of hydrate of iridium chloride hydrochloride. Moreover, an organometallic complex having platinum as a central metal can be obtained by replacing hydrate of iridium chloride by salt including platinum such as potassium tetrachloroplatinate.

Embodiment 3

A mode of a light-emitting element using an organometallic complex according to the present invention is explained with reference to FIG. 1.

FIG. 1 shows a light-emitting element having a light-emitting layer 163 between a first electrode 151 and a second electrode 152. The light-emitting layer 163 includes the organometallic complex according to the present invention having a structure represented by a general formula (1) or (2), alternatively, the organometallic complex according to the present invention represented by a general formula (3) or (4).

In addition to the light-emitting layer 163, a hole injecting layer 161, a hole transporting layer 162, an electron transporting layer 164, an electron injecting layer 165, and the like are provided between the first electrode 151 and the second electrode 152. When applying voltage so that electric potential of the first electrode 151 is higher than that of the second electrode 152, these layers are stacked so that holes are injected from the first electrode 151 side and electrons are injected from the second electrode 152 side.

Holes injected from the first electrode 151 side and electrons injected from the second electrode 152 side are recombined with each other within the light-emitting layer 163 in the light-emitting element to make the organometallic complex be an excited state. Then, the organometallic complex in the excited state emits light while returning to the ground state. Therefore, the organometallic complex according to the present invention serves as a light-emitting material.

Here, the light-emitting layer 163 is a layer including the organometallic complex according to the present invention. The light-emitting layer 163 is a layer made from only the organoinetallic complex according to the present invention. Alternatively, the light-emitting layer 163 is preferably formed by dispersing light-emitting materials into a layer having a larger energy gap than that of the light-emitting material in the case of occurring concentration quenching. Light emission can be prevented from quenching due to concentration by dispersing the organometallic complex according to the present invention to be included in the light-emitting layer 163. As used herein, the term "energy gap" refers to an energy gap between an LUMO level and a HOMO level.

A material used to make the organometallic complex according to the present invention be a dispersion state is not especially limited. In addition to a compound having an aryl amine skeleton such as 2,3-bis(4-diphenylaminophenyl) quinoxaline (abbreviated as TPAQn) or 4,4'-bis[N-(1-naphtyl)-N-phenylamino]biphenyl (abbreviated as NPB); a carbazole derivative such as 4,4'-bis(N-carbazolyl) biphenyl (abbreviated as CBP) or 4,4',4"-tris(N-carbazolyl) triphenylamine (abbreviated as TCTA); a metal complex such as bis[2-(2-hydroxyphenyl)pyridinato]zinc (abbreviated as $Znpp_2$) or bis [2-(2-hydroxyphenyl)benzoxazolate]zinc (abbreviated as $Zn(BOX)_2$), tris(8-quinolinolato) aluminum (abbreviated as $Alq_3$), or the like is preferably used. One or two or more of these materials are selected to be mixed to the light-emitting layer 163 so that the organometallic complex according to the present invention becomes a dispersion state. By mixing especially the organometallic complex according to the present invention into a bipolar substance such as TPAQn, the organometallic complex according to the present invention can be more efficiently emitted. Such the layer formed a mixed plurality of compounds can be formed by co-evaporation. As used herein, the term "co-evaporation" refers to a method that raw materials are vaporized respectively from a plurality of evaporation sources provided in one processing chamber and the vaporized raw materials are mixed in a gaseous state to be deposited over a subject.

The first electrode 151 and the second electrode 152 are not especially limited. In addition to indium tin oxide, indium tin oxide containing silicon oxide, or indium oxide formed using a target mixed with 2 to 20 wt. % of zinc oxide (ZnO); Gold (Au), platinum (Pt), nickel (Ni), tungsten (W), chromium (Cr), molybdenum (Mo), iron (Fe), cobalt (Co), copper (Cu), palladium (Pd), or tantalum nitride can be used as a material for the first electrode 151 and the second electrode 152. In addition to aluminum; alloy of magnesium and silver, alloy of aluminum and lithium, or the like can be used for forming the first electrode 151. A method for forming the first electrode 151 and the second electrode 152 is not especially limited. For example, a sputtering method, a vapor deposition method, or the like can be used. In order to extract light emission to the outside, either or both of the first electrode 151 and the second electrode 152 are preferably formed by using indium tin oxide or the like or by depositing silver, aluminum, or the like to have a thickness of from several nanometers to several tens nanometers.

As shown in FIG. 1, the hole transporting layer 162 can be provided between the first electrode 151 and the light-emitting layer 163. A hole transporting layer is a layer having a function of transporting holes injected from the first electrode 151 side to the light-emitting layer 163. By providing the hole transporting layer 162, the distance between the first electrode 151 and the light-emitting layer 163 can be increased. As a result, quenching due to metal included in the first electrode 151 can be prevented. The hole transporting layer is preferably formed by a material having a high hole transporting property, especially, a material having hole mobility of $1 \times 10^{-6}$ $cm^2/Vs$ or more. As used herein, the term "material having a high hole transporting property" refers to a material having higher mobility of holes than that of electrons and having a ratio value of hole mobility to electron mobility (=hole mobility/electron mobility) of more than 100. As a specific example of a material for forming the hole transporting layer 162, 4,4'-bis[N-(1-naphtyl)-N-phenylamino]biphenyl (abbreviated as NPB), 4,4'-bis[N-(3-methylphenyl)-N-phenylamino]biphenyl (abbreviated as TPD), 4,4',4"-tris(N, N-diphenylamino) triphenylamine (abbreviated as TDATA), 4,4',4"-tris[N-(3-methylphenyl)-N-phenylamino]triphenylamine (abbreviated as MTDATA), 4,4'-bis{N-[4-(N,N-di-m-tolylamino)phenyl]-N-phenylamino}biphenyl (abbreviated as DNTPD), 1,3,5-tris[N,N-di(m-tolyl)amino]benzene (abbreviated as m-MTDAB), 4,4',4"-tris(N-carbazolyl) triphenylamine (abbreviated as TCTA), phthalocyanine (abbreviated as $H_2Pc$), copper phthalocyanine (abbreviated as CuPc), vanadylphthalocyanine (abbreviated as VOPc), or the like can be nominated. Further, the hole transporting layer 162 can be formed to have a multilayer structure formed by stacking two or more of layers made from the foregoing materials.

As shown in FIG. 1, the electron transporting layer 164 can be provided between the second electrode 152 and the light-emitting layer 163. Here, an electron transporting layer is a layer having a function of transporting electrons injected from the second electrode 152 to the light-emitting layer 163. By providing the electron transporting layer 164, the distance between the second electrode 152 and the light-emitting layer 163 can be increased. As a result, quenching due to; metal included in the second electrode 152 can be prevented. The electron transporting layer is preferably formed by a material having a high electron transporting property, especially, a material having electron mobility of $1 \times 10^{-6}$ $cm^2/Vs$ or more. As used herein, the term "material having a high electron transporting property" refers to a material having higher mobility of electrons than that of holes and having a ratio value of electron mobility to hole mobility (=electron mobility/hole mobility) of more than 100. As a specific example of a material for forming the electron transporting layer 164, in addition to a metal complex such as tris(8-quinolinolato) aluminum (abbreviated as $Alq_3$), tris(4-methyl-8-quinolinolato) aluminum (abbreviated as $Almq_3$), bis(10-hydroxybenzo[h]-quinolinato) berylium (abbreviated as $BeBq_2$), bis (2-methyl-8-quinolinolato)-4-phenylphenolate-aluminum (abbreviated as BAlq), bis[2-(2-hydroxyphenyl)benzoxazolate]zinc (abbreviated as $Zn(BOX)_2$), bis[2-(2-hydroxyphenyl)benzothiazorato]zinc (abbreviated as $Zn(BTZ)_2$); 2-(4-biphenylyl)-5-(4-tent-buthylphenyl)-1,3,4-oxadiazole (abbreviated as PBD), 1,3-bis[5-(p-tert-buthylphenyl)-1,3,4-oxadiazole-2-yl]benzene (abbreviated as OXD-7), 3-(4-tert-buthylphenyl)-4-phenyl-5-(4-biphenylyl)-1,2,4-triazole (abbreviated as TAZ), 3-(4-tert-buthylphenyl)-4-(4-ethylphenyl)-5-(4-biphenylyl)-1,2,4-triazole (abbreviated as p-EtTAZ), bathophenanthroline (abbreviated as BPhen), bathocuproin (abbreviated as BCP), 4,4-bis(5-methylbenzoxazol-2-yl) stilbene (abbreviated as BzOs), or the like can be used can be nominated. Further, the electron transporting layer 164 can be formed to have a multilayer structure formed by stacking two or more of layers made from the foregoing materials.

In addition to the above substances, the hole transporting layer 162 and the electron transporting layer 164 may be respectively formed by a bipolar substance. The bipolar substance indicates the following substance: when carrier mobility of either electrons or holes is compared with other carrier's mobility, a value of a ratio of one carrier mobility to the other carrier mobility is 100 or less, preferably 10 or less. As for the bipolar substance, for example, 2,3-bis(4-diphenylaminophenyl) quinoxaline (abbreviated as TPAQn), 2,3-bis{-4-[N-(1-naphthyl)-N-phenylamino]phenyl}-dibenzo[f,h]quinoxaline (abbreviated as NPADiBzQn), and the like can be given. It is preferable to use a substance of which hole and electron mobility are each $1 \times 10^{-6}$ $cm^2/Vs$ or more in particular among the bipolar substance. In addition, the hole transporting layer 162 and the electron transporting layer 164 may be formed by the same bipolar substance.

As shown in FIG. 1, the hole injecting layer 161 can be provided between the first electrode 151 and the hole transporting layer 162. The hole injecting layer 161 is a layer having a function of assisting injection of holes from the first electrode 151 to the hole transporting layer 162. By providing the hole injecting layer 161, the difference in ionization potential between the first electrode 151 and the hole transporting layer 162 is relieved and holes become easy to be injected. The hole injecting layer 161 is preferably formed by a material having smaller ionization potential than that of a material which forms the hole transporting layer 162 and larger ionization potential than that of a material which forms the first electrode 151, or a material having an energy band which bends when the material is formed into a thin film having a thickness of 1 to 2 nm between the hole transporting layer 162 and the first electrode 151. As a specific example of a material for forming the hole injecting layer 161, a phthalocyanine-based compound such as phthalocyanine (abbreviated as $H_2Pc$) or copper phthalocyanine (CuPc), a high molecular weight material such as poly(ethylenedioxythiophene)/poly(styrenesulfonic acid) solution (PEDOT/PSS), or the like can be given. That is, the hole injecting layer 161 can be formed by selecting a material so that ionization potential of the hole injecting layer 161 is relatively smaller than that of the hole transporting layer 162.

As shown in FIG. 1, the electron injecting layer 165 can be provided between the second electrode 152 and the electron transporting layer 164. Here, the electron injecting layer 165 is a layer having a function of assisting injection of electrons from the second electrode 152 to the electron transporting layer 164. By providing the electron injecting layer 165, the difference in electron affinity between the second electrode 152 and the electron transporting layer 164 can be relieved and electrons become easy to be injected. The electron injecting layer 165 is preferably formed by a material having larger electron affinity than that of a material which fowls the electron transporting layer 164 and smaller electron affinity than that of a material which forms the second electrode 152, or a material having an energy band which bends when the material is formed into a thin film of having a thickness of 1 to 2 nm between the electron transporting layer 164 and the second electrode 152. As a specific example of a material for forming the electron injecting layer 165, an inorganic material such as alkaline metal, alkaline earth metal, a fluoride of alkaline metal, a fluoride of alkaline earth metal, an oxide of alkaline metal, or an oxide of alkaline earth metal. In addition to the inorganic material, a substance which can be used to form the electron transporting layer 164 such as BPhen, BCP, p-EtTAZ, or TAZ can also be used as a substance for forming the electron injecting layer 165 by selecting a substance of which electron affinity is higher than that of a substance for forming the electron transporting layer 164 among these substances. That is, the electron injecting layer 165 can be formed by using a material so that electron affinity of the electron injecting layer 165 is relatively higher than that of the electron transporting layer 164.

In the light-emitting element according to the present invention, the hole injecting layer 161, the hole transporting layer 162, the light-emitting layer 163, the electron transporting layer 164, and the electron injecting layer 165 can be respectively formed by any one of a vapor deposition method, an ink jetting method, and a coating method. Further, the first electrode 151 or the second electrode 152 can be formed by either of a sputtering method or a vapor deposition method.

A hole generating layer can be provided instead of the hole injecting layer 161 or an electron generating layer can be provided instead of the electron injecting layer 165.

Here, the hole generating layer is a layer for generating holes. The hole generating layer can be formed by mixing at least one material selected from a material having higher mobility of holes than that of electrons and a bipolar substance to a material which has electron accepting property with respect to the foregoing materials. As the material selected from a material having higher mobility of holes than that of electrons, a material similarly to a material which can be used to form the hole transporting layer 162 can be used. As the bipolar substance, the above mentioned material such as TPAQn can be used. In particular, a material having a triphenylamine as a skeleton is preferably used among the material having higher mobility of holes than that of electrons and the bipolar substance. Holes can become easy to be generated by using the material having triphenylamine as a skeleton. As the material having electron accepting property, metal oxide such as molybdenum oxide, vanadium oxide, ruthenium oxide, or rhenium oxide is preferably used.

The electron generating layer is a layer for generating electrons. The electron generating layer can be formed by mixing at least one material selected from a material having higher mobility of electrons than that of holes and a bipolar substance to a material which has electron releasing property with respect to the foregoing materials. As the material selected from a material having higher mobility of electrons than that of holes, a material similarly to a material which can be used to form the electron transporting layer 164 can be used. As the material having electron releasing property, a material selected from an alkali metal and an alkaline earth metal, specifically, lithium (Li), calcium (Ca), natrium (Na), kalium (Ka), magnesium (Mg), or the like. At least one material selected from an alkali metal oxide and an alkaline earth metal oxide, specifically, a lithium oxide ($Li_2O$), a calcium oxide (CaO), a natrium oxide ($Na_2O$), a kalium oxide ($K_2O$), a magnesium oxide (MgO), or the like can be used as a material having electron releasing property. At least one material selected from alkali metal fluoride and alkaline earth metal fluoride, specifically, a lithium fluoride (LiF), a cesium fluoride (CsF), a calcium fluoride ($CaF_2$), or the like. Further, at least one material selected from an alkali metal nitride and an alkaline earth metal nitride, specifically, a calcium nitride, a magnesium nitride, or the like can be used.

The light-emitting element according to the present invention can exhibit red emission with good chromaticity since it uses the organometallic complex according to the present invention. Further, the light-emitting element according to the present invention has good light emission efficiency since it can emit phosphorescence.

Embodiment 4

A light-emitting element according to the present invention can have a plurality of light-emitting layers. For example, white emission can be obtained by providing a plurality of light-emitting layers and mixing light emissions from each of the plurality of the light-emitting layers. In this embodiment, a mode of a light-emitting element including a plurality of light-emitting layers is explained with reference to FIGS. 2 and 3.

Figure 2:
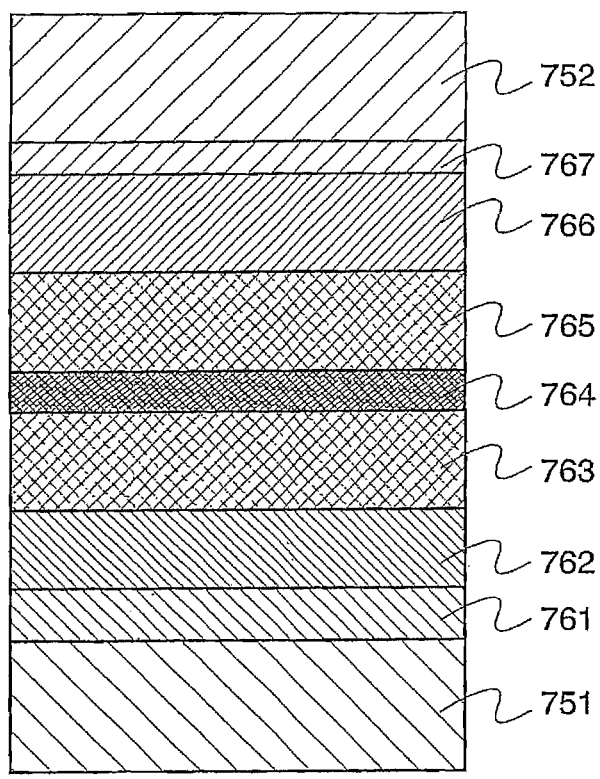
FIG. 2 is an explanatory view for showing a light-emitting element according to the present invention.

In FIG. 2, a first light-emitting layer 763 and a second light-emitting layer 765 are provided between a first electrode 751 and a second electrode 752. An energy generating layer 764 is preferably provided between the first light-emitting layer 763 and the second light-emitting layer 765.

When applying voltage so that electric potential of the first electrode 751 is higher than that of the second electrode 752, current is flown between the first electrode 751 and the second electrode 752, and holes and electrons are recombined with each other within the first light-emitting layer 763, the second light-emitting layer 765, or the energy generating layer 764. Excitation energy generated due to the recombination is moved from the energy generating layer 764 to each of the first light-emitting layer 763 and the second light-emitting layer 765, and a first light-emitting material included in the first light-emitting layer 763 and a second light-emitting material included in the second light-emitting layer 765 are made to be excited states. The excited first and second light-emitting materials emit light while returning to the ground states.

The first light-emitting layer 763 includes a fluorescent material such as parylene, 2,5,8,11-tert-butylperylene (TBP), 4,4'-bis[2-diphenylvinyl]biphenyl (DPVBi), 4,4'-bis[2-(N-ethylcarbazole-3-yl)vinyl]biphenyl (BCzVBi), bis(2-methyl-8-quinolinolato)-4-phenylphenolato-aluminum (BAlq), bis(2-methyl-8-quinolinonato)-chlorogallium (Gamq$_2$Cl); or a light-emitting material as typified by a phosphorescent material such as bis[2-(3,5-bis(trifluoromethyl)phenyl)pyridinato-N,C$^{2'}$]iridium (III) picolinate (Ir(CF$_3$ppy)$_2$(pic)), bis[2-(4,6-difluorophenyl) pyridinato-N,C$^{2'}$]iridium (III) acetylacetonato (Fir(acac)), bis[2-(4,6-difluorophenyl) pyridinato-N,C$^{2'}$]iridium (III) picolinate (Fir(pic)). The first light-emitting layer 763 exhibits light emission having a peak at 450 to 510 nm in an emission spectrum. The second light-emitting layer 765 includes the organometallic complex according to the present invention serving as a light-emitting material and exhibits light emission having a peak at 580 to 680 nm in an emission spectrum. Emission color of light emission generated in the first light-emitting layer 763 and emission color of light emission generated in the second light-emitting layer 765 are emitted to the outside through either or both of the first electrode 751 and the second electrode 752. Each of the light emission emitted to the outside is mixed with each other visually and is visible as white emission.

The first light-emitting layer 763 is preferably formed by dispersing a light-emitting material which can exhibit light at 450 to 510 nm into a layer formed by a material having a larger energy gap (the first host) than that of the light-emitting material, alternatively, the first light-emitting layer 763 is formed by a layer made from a light-emitting material which can exhibit light at 450 to 510 nm. As the first host, in addition to NPB, CBP, TCTA, Znpp$_2$, or ZnBOX, 9,10-di(2-naphtyl) anthracene (abbreviated as DNA), 9,10-di(2-naphtyl)-2-tent-buthylanthracence (abbreviated as t-BuDNA), or the like. The second light-emitting layer 765 is preferably formed by dispersing the organometallic complex according to the present invention into a layer made from a material having a larger energy gap (the second host) than that of the organometallic complex according to the present invention. As the second host, TPAQn, NPB, CBP, TCTA, Znpp$_2$, Zn(BOZ)$_2$, Alq$_3$, or the like can be used. The energy generating layer 764 is preferably formed to have functions of moving energy generated in the first light-emitting layer 763, the second light-emitting layer 765, or the energy generating layer 764 to both the first light-emitting layer 763 and the second light-emitting layer 765 and blocking the move of the energy only to either of the first light-emitting layer 763 or the second light-emitting layer 765. Specifically, the energy generating layer 764 can be made from TPAQn, NPB, CBP, TCTA, Znpp$_2$, Zn(BOZ)$_2$, or the like. Therefore, a problem with obtaining white emission can be prevented by providing the energy generating layer 764, which arises from the fact that emission intensity of only either of the first light-emitting layer 763 or the second light-emitting layer 765 is increased.

A light-emitting material included in the first light-emitting layer 763 and the second light-emitting layer 765 is not especially limited.

The light-emitting element including two light-emitting layers is described as shown in FIG. 2 in this embodiment; however, the number of the light-emitting layers is not limited to two. For example, the light-emitting layer can be formed by three layers. Light emissions generated from each of the light-emitting layers are mixed with each other to make visible white emission.

As shown in FIG. 2, an electron transporting layer 762 can be provided between the first light-emitting layer 763 and the first electrode 751. In addition to the electron transporting layer 762, an electron injecting layer 761 can be provided between the electron transporting layer 762 and the second electrode 752 as shown in FIG. 2. Further, a hole injecting layer 767 can be provided between a hole transporting layer 766 and the second electrode 752.

Figure 3:
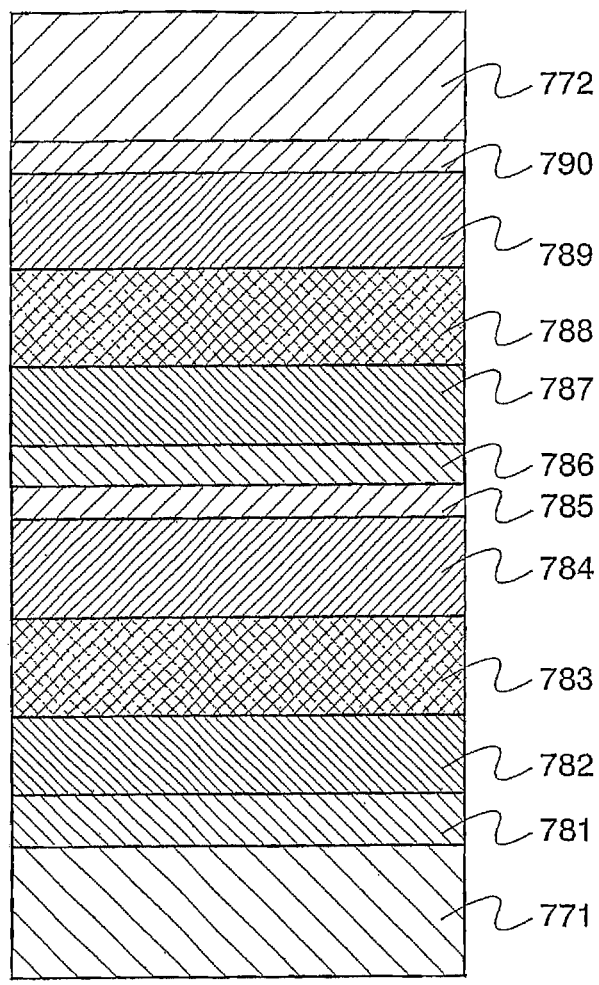
FIG. 3 is an explanatory view for showing a light-emitting element according to the present invention.

Besides the light-emitting element explained with reference to FIG. 2, a light-emitting element as shown in FIG. 3 can be fowled. The light-emitting element shown in FIG. 3 has a first light-emitting layer 783 and a second light-emitting layer 788 between a first electrode 771 and a second electrode 772, and has a first layer 785 and a second layer 786 between the first light-emitting layer 783 and the second light-emitting layer 788.

The first layer 785 is a layer for generating holes, whereas the second layer 786 is a layer for generating electrons. When applying voltage so that electric potential of the first electrode 771 is higher than that of the second electrode 772, electrons injected from the first electrode 771 and holes injected from the first layer 785 are recombined with each other within the first light-emitting layer 783, and light-emitting materials included in the first light-emitting layer 783 emit light. Moreover, holes injected from the second electrode and electrons injected from the second layer 786 are recombined with each other within the second light-emitting layer 788 and light-emitting materials included in the second light-emitting layer 788 emit light.

The organometallic complexes according to the present invention are included in the first light-emitting layer 783 so as to be served as light-emitting materials. Light emission having a peak at 580 to 680 nm can be obtained from the first light-emitting layer 783. The second light-emitting layer 788 includes light-emitting materials as typified by fluorescent materials such as parylene, TBP, DPVBi, BCzVBi, BAlq, or Gamq$_2$CL, or phosphorescent materials such as Ir(CF$_3$ppy)$_2$(pic), Fir(acac), or Fir(pic), and emits light having a peak at 450 to 510 nm in an emission spectrum. Light emissions from the first light-emitting layer 783 and the second light-emitting layer 788 are emitted from either or both of the first electrode 771 and the second electrode 772. Light emissions from both of the light-emitting layers are visually mixed and are visible as white emission.

In the light-emitting layer 783, the organometallic complex is preferably included in a dispersion state in the first host as noted above. The second light-emitting layer 788 is preferably formed in a similar way to the above mentioned second light-emitting layer 788.

The first layer 785 is preferably a layer composed of a material having a higher transporting property of holes than that of electrons and including a material having electron accepting property to the material. As the material having a higher transporting property of holes than that of electrons, a similar material to the material used for forming a hole transporting layer is used. As the material having electron accepting property to the material having a higher transporting property of holes than that of electrons, an molybdenum oxide, a vanadium oxide, 7,7,8,8-tetracyanoquinodime thane (abbreviated as TCNQ), 2,3,5,6-tetrafluoro-7,7,8,8-tetracyanoquinodimethane (abbreviated as F4-TCNQ), or the like can be used.

The second layer 786 is preferably a layer composed of a material having a higher transporting property of electrons than that of holes and including a material having electron releasing property to the material. As the material having a higher transporting property of electrons than that of holes, a similar material to the material used for forming an electron transporting layer is used. As the material having electron releasing property to the material having a higher transporting property of electrons than that of holes, an alkali metal such as lithium or cesium, an alkaline earth metal such as magnesium or calcium, or a rare earth metal such as erbium or ytterbium can be used.

As shown in FIG. 3, an electron transporting layer 782 can be provided between the first light-emitting layer 783 and the first electrode 771. Further, an electron injecting layer 781 can be provided between the electron transporting layer 782 and the first electrode 771. A hole transporting layer 784 can be provided between the first light-emitting layer 783 and the first layer 785. A hole transporting layer 789 can be provided between the second light-emitting layer 788 and the second electrode 772. A hole injecting layer 790 can be provided between the hole transporting layer 789 and the second electrode 772. An electron transporting layer 787 can be provided between the second light-emitting layer 788 and the second layer 786.

The light-emitting element including two light-emitting layers is described as shown in FIG. 3 in this embodiment; however, the number of the light-emitting layers is not limited to two. For example, the light-emitting layer can be formed by three layers. Light emissions generated from each of the light-emitting layers are mixed with each other to make visible white emission.

Embodiment 5

Figure 4:
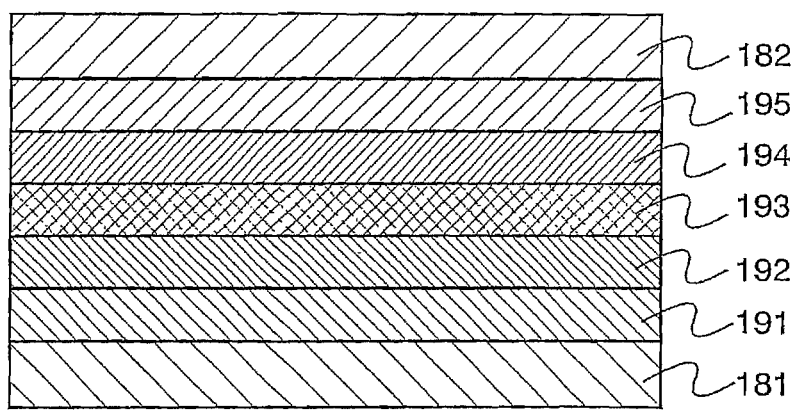
FIG. 4 is an explanatory view for showing a light-emitting element according to the present invention.

A mode of a light-emitting element using an organometallic complex according to the present invention as a sensitizer is explained in this embodiment with reference to FIG. 4.

FIG. 4 shows a light-emitting element having a light-emitting layer 193 between a first electrode 181 and a second electrode 182. The light-emitting layer 193 includes the organometallic complex according to the present invention having a structure represented by any one of general formulae (1), (2), (12), and (13), the organometallic complex according to the present invention represented by any one of general formulae (3), (4), (14), and (15), and a fluorescent compound capable of exhibiting longer wavelength emission than that of the organometallic complex according to the present invention.

In the light-emitting element, hole injected from the first electrode 181 and electrons injected from the second electrode are recombined with each other within the light-emitting layer 193 to make the fluorescent compound be an excited state. The fluorescent compound at an excited state emits light while returning to the ground state. At this time, the organometallic complex according to the present invention serves as a sensitizer for the fluorescent compound to amplify the number of fluorescent compounds at singlet excited states. As noted above, a light-emitting element with good light emission efficiency can be obtained by using the organometallic complex according to the present invention as a sensitizer. In the light-emitting element according to this embodiment, the first electrode 181 serves as an anode, whereas the second electrode 182 serves as a cathode.

The light-emitting layer 193 is not especially limited. The light-emitting layer 193 is preferably a layer formed by dispersing the organometallic complex according to the present invention and the fluorescent compound into a layer made from a material having a larger energy gap than that of the organometallic complex according to the present invention. Accordingly, light emission generated in the organometallic complex according to the present invention can be prevented from quenching due to concentration. Further, the energy gap means an energy gap between an LUMO level and a HOMO level.

Here, the fluorescent compound is not especially limited. As the fluorescent compound, a compound exhibiting light at 650 to 1000 nm such as magnesium phthalocyanine or phthalocyanine is preferably used.

A material which makes the organometallic complex according to the present invention and the fluorescent compound be dispersion states is not especially limited. A material or the like which can be used to make the organometallic complex according to the present invention be a dispersion state descried in Embodiment 3 can be used.

The first and second electrodes are not especially limited. Similar electrodes to the first electrode 181 and the second electrode 182 described in Embodiment 3 can be used.

As shown in FIG. 4, a hole transporting layer 191, a hole injecting layer 192, and the like can be provided between the first electrode 181 and the light-emitting layer 193. An electron transporting layer 194, an electron injecting layer 195, or the like can be provided between the second electrode 182 and the light-emitting layer 193.

The hole transporting layer 191, the hole injecting layer 192, the electron transporting layer 194, and the electron injecting layer 195 can be formed by similar layers to the hole transporting layer 162, the hole injecting layer 161, the electron transporting layer 164, and the electron injecting layer 165. Other functional layers having different functions as those of the hole transporting layer 191, the hole injecting layer 192, the electron transporting layer 194, and the electron injecting layer 195 can be provided.

The light-emitting element described above is obtained by using the organometallic complex according to the present invention as a sensitizer.

Embodiment 6

Since the light-emitting element according to the present invention including the organometallic complex according to the present invention exhibits good emission color, a light-emitting device having a function of displaying an image with good color can be obtained by using the light-emitting element according to the present invention as a pixel.

In this embodiment, a circuit structure and a driving method of a light-emitting device having a display function are explained with reference to FIGS. 5 to 8.

Figure 5:
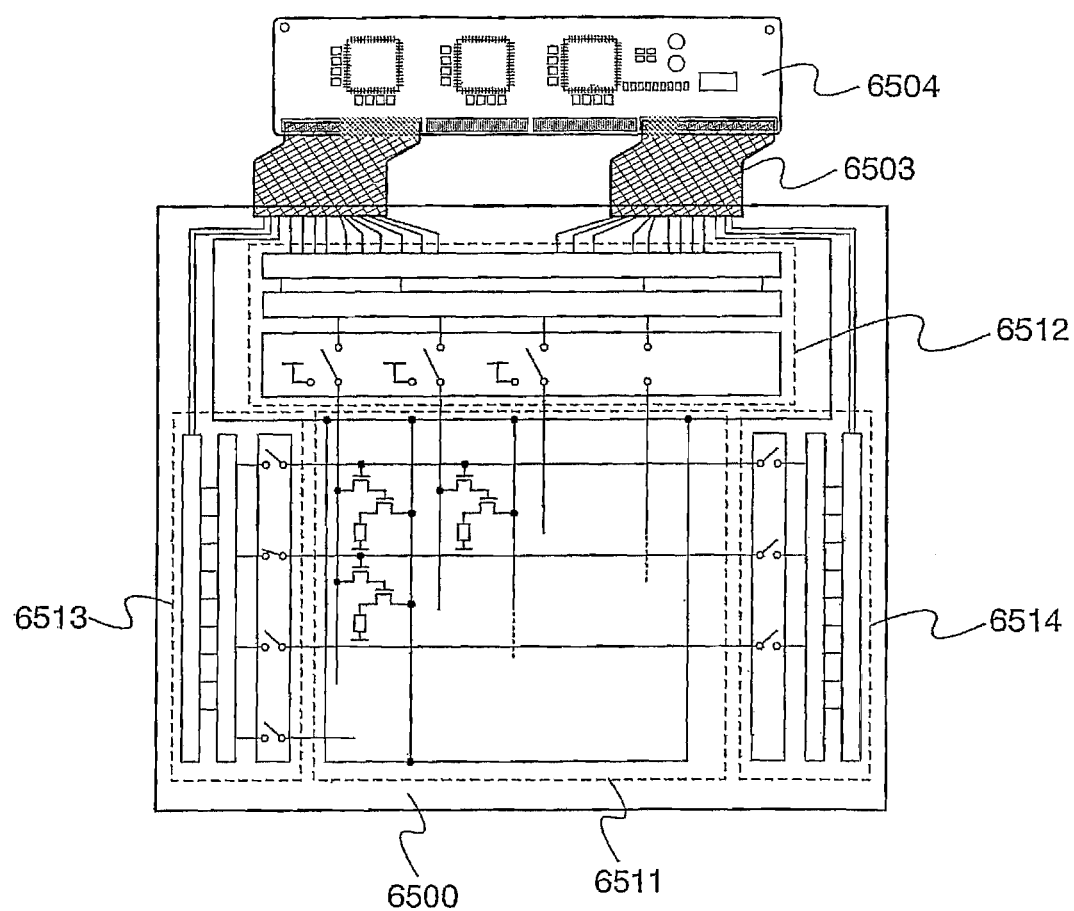
FIG. 5 is an explanatory view for showing a light-emitting device applied with the present invention.

FIG. 5 is a schematic view for showing a top view of a light-emitting device applied with the present invention. In FIG. 5, a pixel portion 6511, a source signal line driver circuit 6512, a writing gate signal line driver circuit 6513, and an erasing gate signal line driver circuit 6514 are provided over a substrate 6500. The source signal line driver circuit 6512, the writing gate signal line driver circuit 6513, and the erasing gate signal line driver circuit 6514 are respectively connected to an FPC (flexible printed circuit) 6513 which is an external input terminal via wiring groups. The source signal line driver circuit 6512, the writing gate signal line driver circuit 6513, and the erasing gate signal line driver circuit 6514 receive respectively a video signal, a clock signal, a start signal, a reset signal, or the like from the FPC 6503. The FPC 6503 is mounted with a printed wiring board (PWB) 6504. The driving circuit portion and with the pixel portion 6511 is not necessarily formed over a common substrate as mentioned above. For example, the driving circuit portion can be formed at the outside of the substrate by utilizing a TCP or the like which is formed by mounting an IC chip over an FPC provided with a wiring pattern.

A plurality of source signal lines are arranged in rows in the pixel portion 6511. Further, current supply lines are arranged in rows. A plurality of gate signal lines which are extending in lines are arranged in rows in the pixel portion 6511. A plurality of pairs of circuits including light-emitting elements is arranged in the pixel portion 6511.

Figure 6:
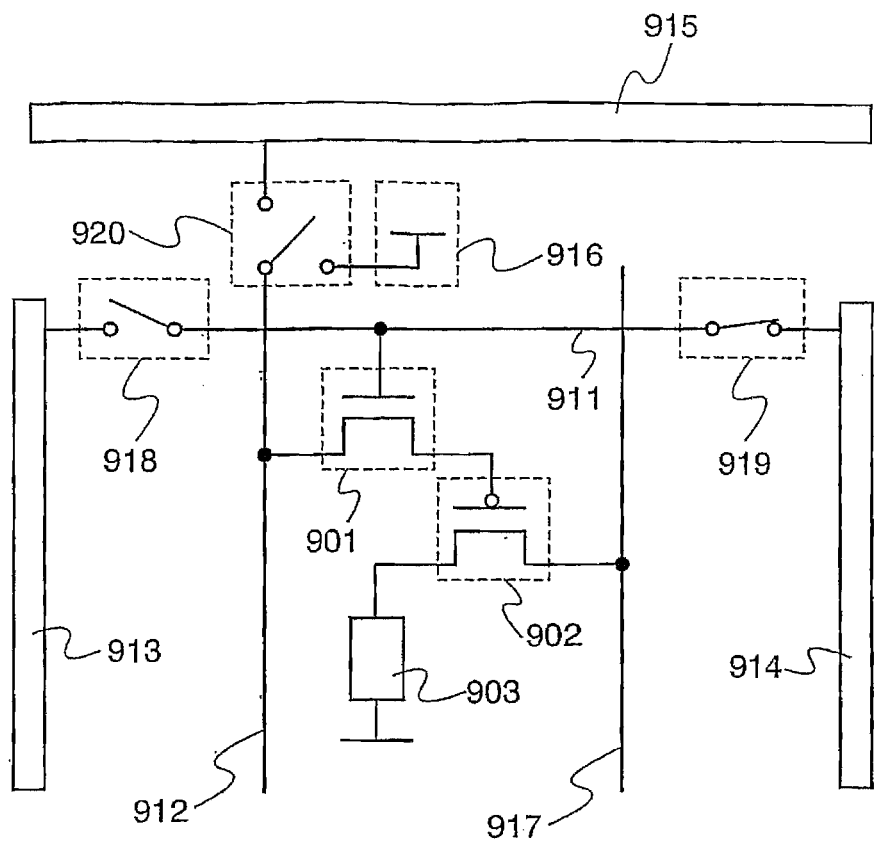
FIG. 6 is an explanatory view for showing a circuit included in a light-emitting device applied with the present invention.

FIG. 6 is a view for showing a circuit for operating one pixel. The circuit shown in FIG. 6 includes a first transistor 901, a second transistor 902, and a light-emitting element 903. The first transistor 901 and the second transistor 902 are three-terminal elements respectively including a gate electrode, a drain region, and a source region. A channel region is interposed between the drain region and the source region. Since the source region and the drain region are changed to each other depending on the structure of a transistor, an operating condition, or the like, it is difficult to determine which region is the source region or the drain region. In this embodiment, regions serving as a source or a drain are respectively denoted by a first electrode and a second electrode.

A gate signal line 911 and a writing gate signal line driver circuit 913 are electrically connected or not connected by a switch 918. The gate signal line 911 and an erasing gate signal line driver circuit 914 are electrically connected or not connected by a switch 919. A source signal line 912 is electrically connected to a source signal line driver circuit 915 or a power source 916 by a switch 920. A gate of the first transistor 901 is electrically connected to the gate signal line 911. A first electrode of the first transistor 901 is electrically connected to the source signal line 912, whereas a second electrode of the first transistor 901 is electrically connected to a gate electrode of the second transistor 902. A first electrode of the second transistor 902 is electrically connected to a current supply line 917, whereas a second electrode of the second transistor 902 is electrically connected to one electrode included in the light-emitting element 903. The switch 918 can be included in the writing gate signal line driver circuit 913. The switch 919 can be included in the erasing gate signal line driver circuit 914. The switch 920 can be included in the source signal line driver circuit 915.

Figure 7:
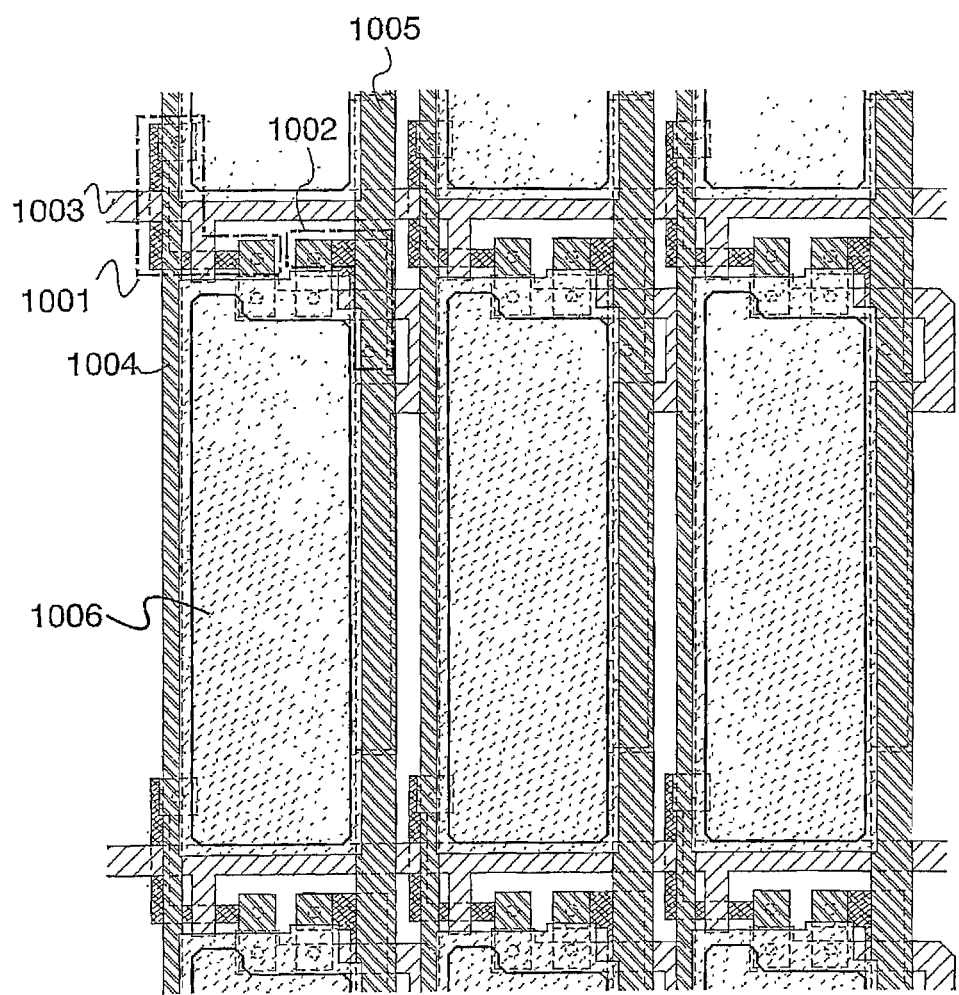
FIG. 7 is a top view of a light-emitting device applied with the present invention.

Arrangement of the transistor, the light-emitting element, or the like in the pixel portion is not especially limited. For example, they can be arranged as illustrated in a top view of FIG. 7. In FIG. 7, a first electrode of a first transistor 1001 is connected to a source signal line 1004, whereas a second electrode of the first transistor 1001 is connected to a gate electrode of a second transistor 1002. A first electrode of a second transistor 1002 is connected to a current supply line 1005, whereas a second electrode of the second transistor 1002 is connected to an electrode 1006 of a light-emitting element. A part of the gate signal line 1003 serves as a gate electrode of the first transistor 1001.

Figure 8:
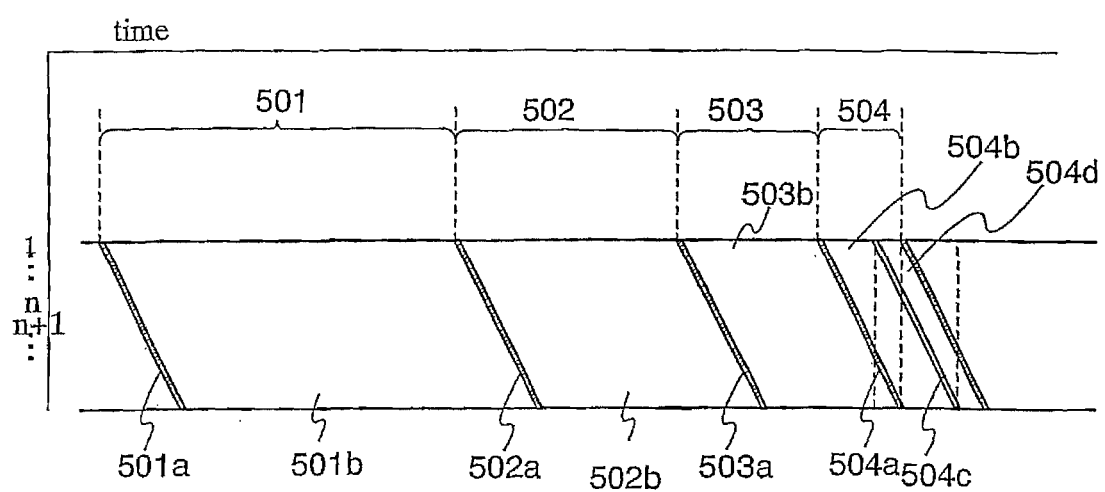
FIG. 8 is an explanatory view for showing a frame operation of a light-emitting device applied with the present invention.

A driving method is explained. FIG. 8 is an explanatory view for showing an operation of a frame with time. In FIG. 8, a crosswise direction represents time proceeding, whereas a lengthwise direction represents the number of scanning stages of the gate signal line.

When image display is performed by using the light-emitting device according to the present invention, a rewrite operation and a display operation of a screen are repeatedly carried out. The number of rewrite operations is not especially limited. The rewrite operation is preferably carried out at least at approximately 60 times per one second so that a person who views the image does not feel a flicker. Here, a period in which the rewrite operation and the display operation of one screen (one frame) is referred to as one frame period.

As shown in FIG. 8, one frame is time-divided into four sub-frames 501, 502, 503, and 504 respectively including writing periods 501a, 502a, 503a, and 504a and retention periods 501b, 502b, 503b, and 504b. In the retention period, a light-emitting element which is given a signal for emitting light is made to be into an emitting state. The ratio of the length of the retention period in each sub-frame is first sub-frame 501: second sub-frame 502: third sub-frame 503: fourth sub-frame 504=$2^3:2^2:2^1:2^0$=8:4:2:1. This makes possible 4-bit gradation. However, the number of bits or the number of gradations is not limited to that described here. For example, eight sub-frames may be provided so as to perform 8-bit gradation.

Operation in one frame will be described. First, writing operation is sequentially performed for each of the first line to the last line in the sub-frame 501. Accordingly, starting time of the writing period depends on lines. Lines of which the writing periods 501a are completed are sequentially moved into the retention periods 501b. In the retention period 501b, a light-emitting element which is given a signal for emitting light is made to be into an emitting state. Further, lines of which the retention periods 501b are completed are sequentially moved into the next sub-frames 502, and writing operation is sequentially performed for each of the first line to the last line as in the case of the sub-frame 501. The operation described above is repeated to complete up to the retention period 504b of the sub-frame 504. When the operation in the sub-frame 504 is completed, the line is moved into the next frame. Thus, the total time of emitting light in each sub-frame is emission time of each light-emitting element in one frame. By varying this emission time with respect to each light-emitting element and combining variously the emission time in one pixel, various display colors having difference in luminosity and chromaticity can be made.

As in the sub-frame 504, before writing up to the last line is completed, when it is required that a retention period is forcibly terminated in lines where writing is finished and which is moved into the retention period, it is preferable that an erasing period 504c be provided after the retention period 504b and a line be controlled so as to be forcibly into a non-emitting state. Further, the line made forcibly to be in the non-emitting state is kept the non-emitting state for a certain period (this period is referred to as a non-emission period 504d). Then, immediately after the writing period of the last line is completed, the lines are sequentially moved into the next writing period (or the next frame) from the first line. This makes it possible to prevent the writing period of the sub-frame 504 from overlapping with the writing period of the next sub-frame.

Although the sub-frames 501 to 504 are arranged in the order of from the longest retention period to the shortest retention period in this embodiment, the arrangement as in this embodiment is not always necessary. For example, the sub-frames 501 to 504 may be arranged in the order of from the shortest retention period to the longest retention period or may be arranged in random order. In addition, the sub-frames may be divided further into a plurality of frames. Namely, scanning of the gate signal lines may be performed at a plurality of times while giving the same image signal.

Hereinafter, operation of the circuit shown in FIG. 6 in a writing period and an erasing period will be described.

First, operation in a writing period will be described. In the writing period, the n-th (n is a natural number) gate signal line 911 is electrically connected to the writing gate signal line driver circuit 913 via the switch 918, and unconnected to the erasing gate signal line driver circuit 914. In addition, the source signal line 912 is electrically connected to the source signal line driver circuit 915 via the switch 920. At this time, a signal is input to the gate of the first transistor 901 connected to the n-th (n is a natural number) gate signal line 911 to turn on the first transistor 901. Then, image signals are input simultaneously to the first to last source signal lines. It is to be noted that the image signals input from the source signal lines 912 at each columns are independent from each other. The image signal input from the source signal lines 912 is input to the gate electrode of the second transistor 902 via the first transistor 901 connected to each the source signal line. At this moment, the value of current to be supplied from the current supply line 917 to the light-emitting element 903 is determined in accordance with the signal input to the second transistor 902. Then, whether the light-emitting element 903 emits light or not is determined depending on the value of the current. For example, in the case that the second transistor 902 is a p-channel transistor, the light-emitting element 903 is made to emit light by inputting a Low Level signal to the gate electrode of the second transistor 902. On the other hand, in the case that the second transistor 902 is an n-channel transistor, the light-emitting element 903 is made to emit light by inputting a High Level signal to the gate electrode of the second transistor 902.

Next, operation in an erasing period will be described. In the erasing period, the n-th (n is a natural number) gate signal line 911 is electrically connected to the erasing gate signal line driver circuit 914 via the switch 919. In addition, the source signal line 912 is electrically connected to the power source 916 via the switch 920. In this case, a signal is input to the gate of the first transistor 901 connected to the n-th gate signal line 911 to turn on the first transistor 901. Then, at this moment, erasing signals are input simultaneously to the first to last source signal lines. The erasing signal input from each of the source signal lines 912 is input to the gate electrode of the second transistor 902 via the first transistor 901 connected to the source signal line 912. At this moment, current supply from the current supply line 917 to the light-emitting element 903 is stopped in accordance with the signal input to the second transistor 902. Then, the light-emitting element 903 is forcibly made to be into a non-emitting state. For example, in the case that the second transistor 902 is a p-channel transistor, the light-emitting element 903 is made not to emit light emitted light by inputting a High Level signal to the gate electrode of the second transistor 902. On the other hand, in the case that the second transistor 902 is an n-channel transistor, the light-emitting element 903 is made not to emit light by inputting a Low Level signal to the gate electrode of the second transistor 902.

As for the n-th line (n is a natural lumber), signals for erasing are input by the operation as described above in an erasing period. However, as described above, the other line (referred to as the m-th line (m is a natural number)) may be a writing period and the n-th line may be an erasing period. In such a case, it is necessary to input a signal for erasing to the n-th line and input a signal for writing to the m-th line by using the source signal line in the same row. Therefore, operation described below is preferably carried out.

Immediately after the n-th light-emitting element 903 is, made not to emit light by the operation in the erasing period described above, the gate signal line 911 and the erasing gate signal line driver circuit 914 are made to be unconnected to each other, and the switch 920 is switched to connect the source signal line 912 and the source signal line driver circuit 915. Then, the source signal line 912 is connected to the source signal line driver circuit 915, simultaneously; the gate signal line 911 is connected to the writing gate signal line driver circuit 913. Then, a signal is input selectively to the m-th signal line from the writing gate signal line driver circuit 913 to turn on the first transistor 901, and signals for writing are input to the first to last source signal lines from the source signal line driver circuit 915. This signal makes the m-th light-emitting element 903 is made to be in an emitting or non-emitting state.

Immediately after the writing period for the m-th line is completed as described above, an erasing period for the (n+1)-th line is started. For that purpose, the gate signal line 911 and the writing gate signal line driver circuit 913 are made to be unconnected to each other, simultaneously; the switch 920 is switched to connect the source signal line and the power source 916. Further, the gate signal-line 911 is made to be unconnected to the writing gate signal line driver circuit 913, simultaneously; the gate signal line 911 is made to be connected to the erasing gate signal line driver circuit 914. Then, a signal is input selectively to the (n+1)-th gate signal line 911 from the erasing gate signal line driver circuit 914 to turn on the first transistor 901, simultaneously; an erasing signal is input from the power source 916. Immediately after the erasing period for the (n+1)-th line is completed, a writing period for the (m+1)-th line is started. Then, an erasing period and a writing period may be repeated in the same way until an erasing period for the last line is completed.

Although the example in which the writing period for the m-th line is provided between the erasing period for the n-th line and the erasing period for the (n+1)-th line is described in this embodiment, the present invention is not limited thereto. The writing period for the m-th line may be provided between an erasing period for (n−1)-th line and an erasing period for n-th line.

In this embodiment, the operation that the erasing gate signal line driver circuit 914 and a certain gate signal line 911 are made to be unconnected to each other, simultaneously; the writing gate signal line driver circuit 913 and the other gate signal line 911 are made to be connected to each other is repeated when the non-emission period 504d is provided in the sub-frame 504. This type of operation may be performed in a frame in which a non-emission period is not particularly provided.

Embodiment 7

A mode of a cross-sectional view of a light-emitting device including a light-emitting element according to the present invention will be explained with reference to FIGS. 9A to 9C.

Figure 9A:
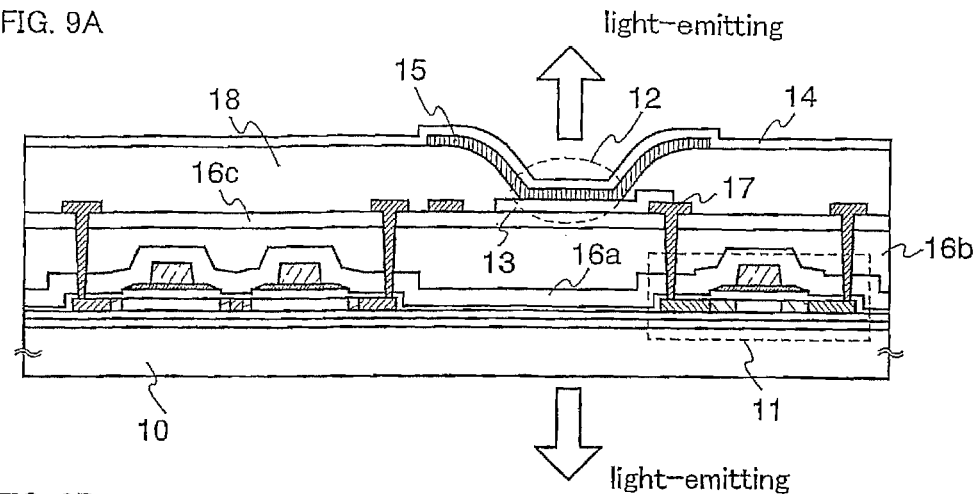
FIGS. 9A to 9C are cross-sectional views of a light-emitting device applied with the present invention.
Figure 9B:
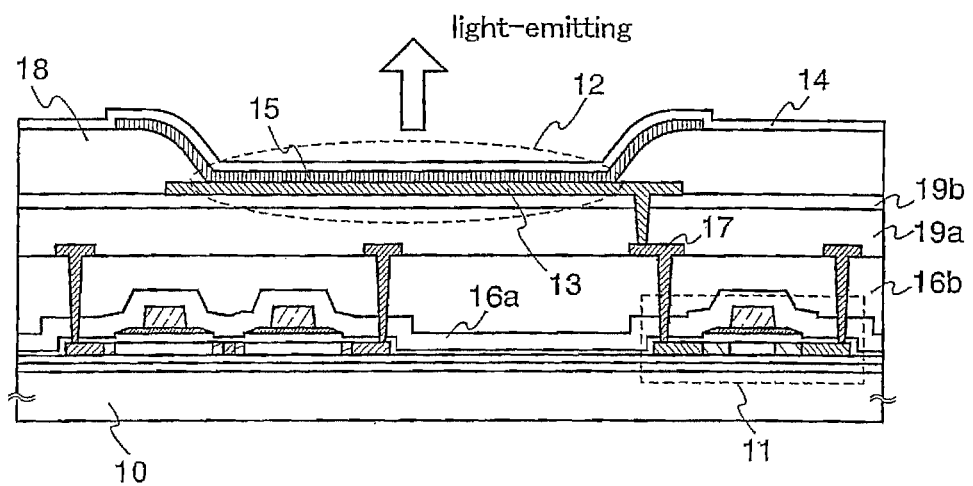
Figure 9C:
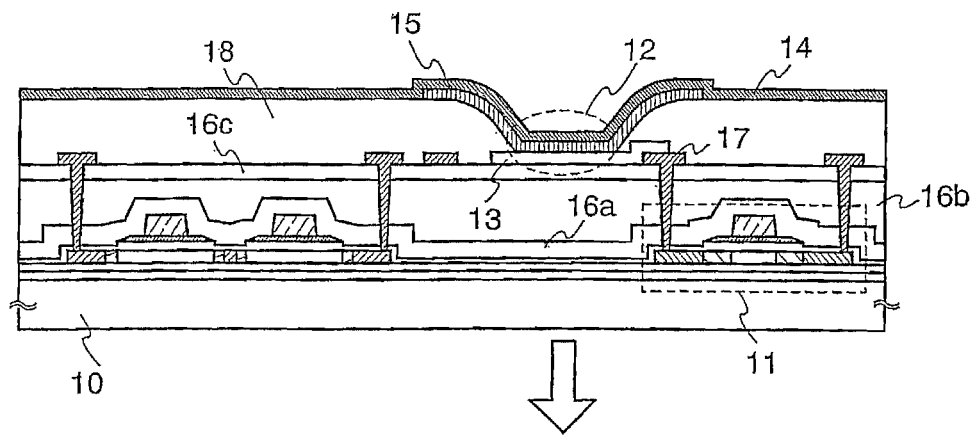

In each of FIGS. 9A to 9C, a region surrounded by a dotted line represents a transistor 11 which is provided for driving a light-emitting element 12 according to the present invention. The light-emitting element 12 of the present invention includes a layer 15 where a hole-generating layer, an electron-generating layer, and a layer containing a light-emitting substance are stacked between a first electrode 13 and a second electrode 14. A drain of the transistor 11 and the first electrode 13 are electrically connected to each other by a wiring 17 which penetrates a first interlayer insulating film 16 (16a, 16b and 16c). The light-emitting element 12 is isolated from another light-emitting elements provided adjacent to the light-emitting element 12 by a partition wall layer 18. A light-emitting device of the present invention having such a structure is provided over a substrate 10 in this embodiment.

Note that the transistor 11 shown in each of FIGS. 9A to 9C is a top-gate transistor in which a gate electrode is provided on a side of a semiconductor layer opposite to the substrate. However, the structure of the transistor 11 is not particularly limited. For example, a bottom-gate transistor may be employed. In the case of using a bottom-gate transistor, either a transistor in which a protection film is formed over a semiconductor layer of a channel (a channel protection transistor) or a transistor in which part of a semiconductor layer of a channel is etched in a concave (a channel etched transistor) may be used.

The semiconductor layer included in the transistor 11 may be either of a crystalline semiconductor or an amorphous semiconductor. In addition, the semiconductor layer included in the transistor 11 may be a semi-amorphous semiconductor, or the like.

Note that a semi-amorphous semiconductor has an intermediate structure between an amorphous structure and a crystalline structure (including a single crystalline structure and a polycrystalline structure), and a third condition that is stable in term of free energy. The semi-amorphous semiconductor further includes a crystalline region having a short-range order along with lattice distortion. A crystal grain with a size of 0.5 nm to 20 μm is included at least in part of a semi-amorphous semiconductor film. A Raman spectrum is shifted to a lower wavenumber side less than 520 cm$^{-1}$. The diffraction peaks of (111) and (220), which are believed to be derived from silicon crystal lattice, are observed in the semi-amorphous semiconductor by the X-ray diffraction. The semi-amorphous semiconductor contains hydrogen or halogen of at least 1 atomic % or more for terminating dangling bonds. The semi-amorphous semiconductor is also referred to as a so-called microcrystalline semiconductor. The semi-amorphous semiconductor is formed by glow discharge decomposition with silicide gas (plasma CVD). As for the silicide gas, $SiH_4$, and besides, $Si_2H_6$, $SiH_2Cl_2$, $SiHCl_3$, $SiCl_4$, $SiF_4$, and the like can be used. The silicide gas may also be diluted with $H_2$, or a mixture of $H_2$ and one or more of rare gas elements of He, Ar, Kr, and Ne. The dilution ratio is set to be in the range of 1:2 to 1:1,000. The pressure is set to be approximately in the range of 0.1 Pa to 133 Pa. The power frequency is set to be 1 to 120 MHz, preferably, 13 to 60 MHz. The substrate heating temperature may be set to be 300° C. or less, more preferably, 100 to 250° C. As for impurity elements contained in the film, each concentration of impurities for atmospheric constituents such as oxygen, nitrogen and carbon is preferably set to be $1\times10^{20}$/cm$^3$ or less. In particular, the oxygen concentration is set to be $5\times10^{19}$/cm$^3$ or less, preferably, $1\times10^{19}$/cm$^3$ or less. Further, the mobility of a TFT (thin film transistor) using a semi-amorphous semiconductor is set to be approximately 1 to 10 m$^2$/Vsec.

As a specific example of a crystalline semiconductor layer, a semiconductor layer made from single crystal silicon, polycrystalline silicon, silicon germanium, or the like can be given. These materials may be formed by laser crystallization. For example, these materials may be formed by crystallization with the use of a solid phase growth method using nickel or the like.

When a semiconductor layer is made from an amorphous substance, for example, amorphous silicon, it is preferable to use a light-emitting device having circuits including only N-channel transistors as the transistor n and the other transistor (a transistor included in a circuit for driving a light-emitting element). Alternatively, a light-emitting device having circuits including either N-channel transistors or P-channel transistors may be employed. Also, a light-emitting device having circuits including both an N-channel transistor and a P-channel transistor may be used.

The first interlayer insulating film 16 may be a multilayer as shown in FIGS. 9A and 9C or a single layer. The interlayer insulating film 16a is made from an inorganic material such as silicon oxide or silicon nitride. The interlayer insulating film 16b is made from acrylic, siloxane (which is a compound composed of a skeleton structure formed by the bond of silicon (Si) and oxygen (O), in which an organic group such as hydrogen or an alkyl group is contained), or a substance with self-planarizing properties which can be formed into a film by coating such as silicon oxide. The interlayer insulating film 16c is made from a silicon nitride film containing argon (Ar). The substances constituting the respective layers are not particularly limited thereto. Therefore, substances other than the above substances may be employed. Alternatively, the above substances may be combined with each other. Accordingly, the first interlayer insulating film 16 may be formed using both an inorganic material and an organic material or by using any one of an inorganic material and an organic material.

The partition wall layer 18 preferably has an edge portion in a shape having the radius of curvature which is variable continuously. This partition wall layer 18 is formed by acrylic, siloxane, resist, silicon oxide, or the like. Note that the partition wall layer 18 may be made from either or both an inorganic material and an organic material.

Each of FIGS. 9A and 9C shows a structure in which only the first interlayer insulating film 16 is interposed between the transistor 11 and the light-emitting element 12. Alternatively, as shown in FIG. 9B, in addition to the first interlayer insulating film 16 (16a and 16b), a second interlayer insulting film 19 (19a and 19b) can be provided. In the light-emitting device as shown in FIG. 9B, the first electrode 13 penetrates the second interlayer insulating film 19 to be electrically connected to the wiring 17.

The second interlayer insulating film 19 may be a multilayer or a single layer as well as the first interlayer insulating film 16. The interlayer insulating film 19a is made from acrylic, siloxane, or a substance with a self-planarizing property which can be formed into a film by, coating such as silicon oxide. The interlayer insulating film 19b is made from a silicon nitride film containing argon (Ar). The substances constituting the respective layers are not particularly limited thereto. Therefore, substances other than the above substances may be employed. Alternatively, the above substances may be combined with each other. Accordingly, the second interlayer insulating film 19 may be formed using both an inorganic material and an organic material or using any one of an inorganic material and an organic material.

When both the first electrode and the second electrode in the light-emitting element 12 are formed by a material having a light-transmitting property, light generated in the light-emitting element can be extracted from both the first electrode 13 and the second electrode 14 as shown in outline arrows in FIG. 9A. When only the second electrode 14 is made from a Material having a light-transmitting property, light generated in the light-emitting element can be extracted only from the second electrode 14 as shown in an outline arrow in FIG. 9B. In that case, the first electrode 13 is preferably made from a material with high reflectance or a film (reflection film) made from a material with high reflectance is preferably provided under the first electrode 13. When only the first electrode 13 is made from a material having a light-transmitting property, light generated in the light-emitting element can be extracted only from the first electrode 13 as shown in an outline arrow in FIG. 9C. In this case, the Second electrode 14 is preferably made from a material with high reflectance or a reflection film is preferably provided over the second electrode 14.

In the light-emitting element 12, the layer 15 may be stacked so that the light-emitting element 12 operates to make the potential of the second electrode 14 be higher than that of the first electrode 13 when applying voltage. Alternatively, in the light-emitting element 12, the layer 15 may be stacked so that the light-emitting element 12 operates to make the potential of the second electrode 14 be lower than that of the first electrode 13 when applying voltage. In the former case, the transistor 11 is an N-channel transistor, whereas in the latter case, the transistor 11 is a P-channel transistor.

Figure 11:
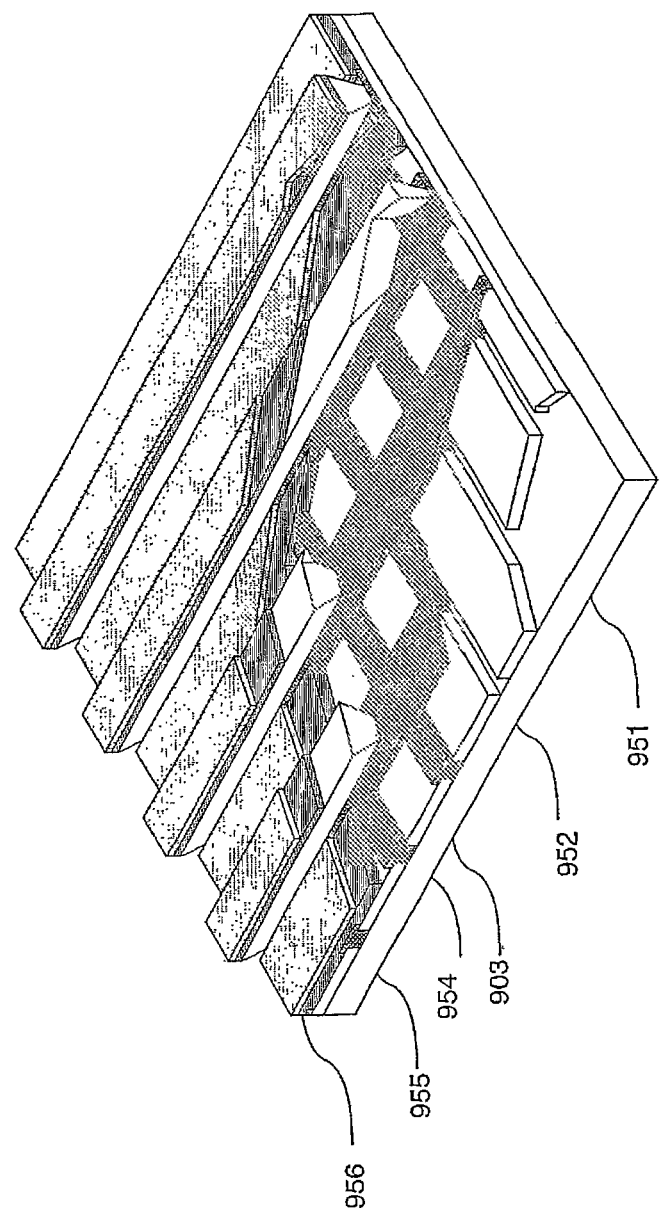
FIG. 11 is a view for showing an electronic device.

As set forth above, this embodiment explains an active light-emitting device that controls driving of a light-emitting element by a transistor; however, a passive light-emitting device which drives a light-emitting element without particularly providing a driving element such as a transistor may be employed as well. FIG. 11 shows a perspective view of a passive light-emitting device which is manufactured applying the present invention. In FIG. 11, a layer 1905 which is formed by stacking sequentially a layer containing a light-emitting material, an electron-generating layer, and a hole-generating layer between an electrode 1902 and an electrode 1906. The edge of the electrode 1902 is covered with an insulating layer 1903. A partition wall layer 1904 is provided over the insulating layer 1903. The nearer the sidewall of the partition wall layer is to a substrate surface, the narrower the distance between one sidewall and the other sidewall is to have inclination. In other words, a cross section of the partition wall layer 1904 in a minor axis is a trapezoid, in which the lower base (a base in the same direction as the face direction of the insulating layer 1903 and in contact with the insulating layer 1903) is shorter than the upper base (a base in the same direction as the face of the insulating layer 1903 and not in contact with the insulating layer 1903). Accordingly, defectiveness of a light-emitting element due to static electricity or the like can be prevented by providing the partition wall layer 1904. In addition, a passive light-emitting device can also be driven with low power consumption by including a light-emitting element of the present invention that is operated with a low drive voltage.

Embodiment 8

Since a light-emitting device including the light-emitting element according to the present invention can display an image with good color, an electronic device which can provide an image with bright color can be obtained by applying the light-emitting device according to the present invention to a display portion of the electronic device.

Figure 10A:
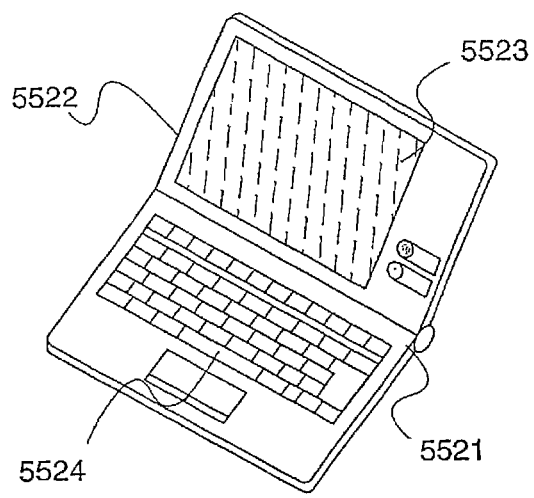
FIGS. 10A to 10C are views for showing electronic devices.
Figure 10B:
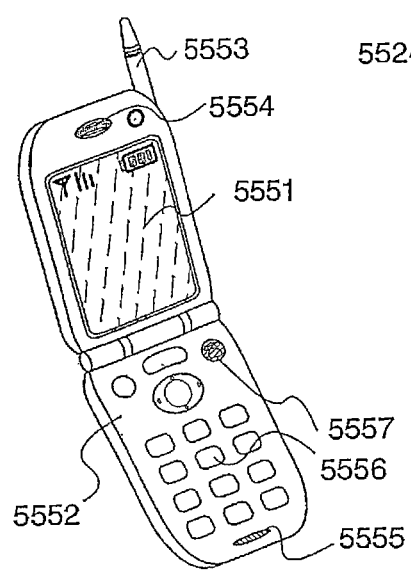
Figure 10C:
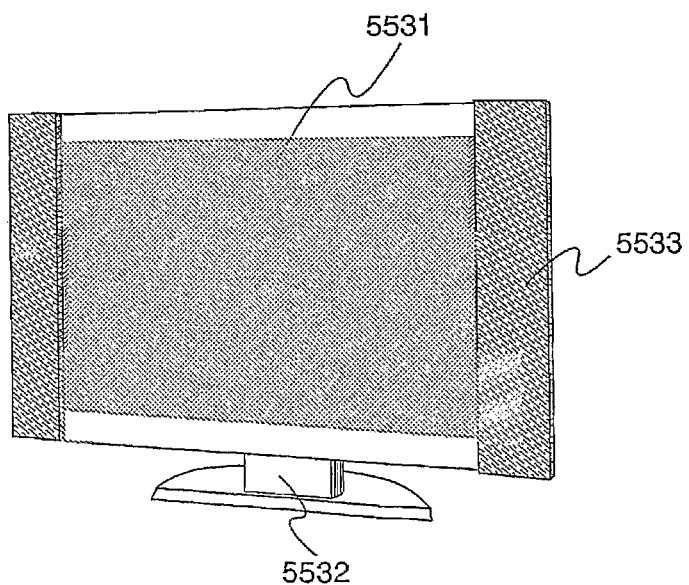

Each of FIGS. 10A to 10C shows one example of an electronic device mounted with a light-emitting device applied with the present invention.

FIG. 10A is a laptop computer manufactured by applying the present invention, which includes a main body 5521, a housing 5522, a display portion 5523, a keyboard 5524, and the like. The personal computer can be completed by incorporating the light-emitting device having a light-emitting element according to the present invention therein as the display portion.

FIG. 10B is a telephone set manufactured by applying the present invention, which includes a main body 5552, a display portion 5551, an audio output portion 5554, an audio input portion 5555, operation switches 5556 and 5557, an antenna 5553, and the like. The telephone set can be completed by incorporating a light-emitting device having a light-emitting element according to the present invention therein as the display portion.

FIG. 10C is a television receiver manufactured by applying the present invention, which includes a display portion 5531, a housing 5532, speakers 5533, and the like. The television receiver can be completed by incorporating a light-emitting device having a light-emitting element according to the present invention therein as the display portion.

As set forth above, a light-emitting device of the present invention is suitable to be used as the display portions of various kinds of electronic devices.

Although a personal computer is explained in this embodiment, the light-emitting device having a light-emitting element according to the present invention can be mounted to a telephone, a navigation device, a camera, or the like.

EXAMPLE 1

Hereinafter, a synthesis example of an organometallic complex according to the present invention is explained. The present invention is not limited to the organometallic complex of the following synthesis example.

SYNTHESIS EXAMPLE 1

A method for synthesizing (acetylacetonato)bis(2-methyl-3-phenylquinoxalinato) iridium (III) [abbreviated as Ir(mpq)$_2$ (acac)] represented by a structural formula (16) is explained. The method for synthesizing Ir(mpq)$_2$(acac) is not limited to that explained in this synthesis example.

Another synthesis example can be used.

Step 1: Synthesis of a Ligand (Abbreviated as Hmpq)

3.23 g of 1-phenyl-1,2-propanedione and 2.48 g of 1,2-phenylendiamine were refluxed in a chloroform solvent in nitrogen atmosphere for 4 hours. An organic layer was washed with 1 mol/L hydrochloric acid, and washed with a saturated salt solution, then, dried. The solvent was distilled off to give a ligand, 2-methyl-3-phenylquinoxaline (abbreviated as Hmpq) (pale orange powder, yields of 98%). A synthesis scheme of the step 1 (b-1) is represented as follows:

Formula 44

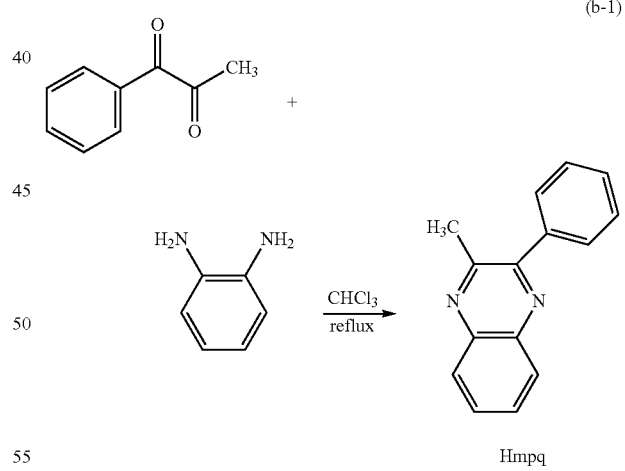

(b-1)

Step 2: Synthesis of Binuclear Complex (Abbreviated as [Ir(mpq)$_2$Cl]$_2$)

1.97 g of the ligand, Hmqp and 1.07 g of iridium chloride hydrochloride hydrate (IrCl$_3$.HCl.H$_2$O) were mixed with each other with a mixed solution of 21 ml of 2-ethoxyethanol and 7 ml of water as a solvent. The solution was refluxed in nitrogen atmosphere for 16 hours to give a binuclear complex (abbreviated as [Ir(mpq)$_2$Cl]$_2$) (reddish brown powder, yields of 78%). A synthesis scheme of the step 2 (b-2) is represented as follows:

Formula 45

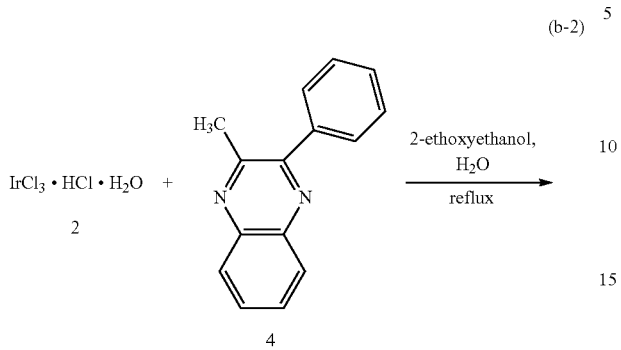

(b-2)

Step 3: Synthesis of an Organometallic Complex (Abbreviated as Ir(mpq)$_2$(acac)) Used for a Light-emitting Element According to the Present Invention 0.90 g of the [Ir(mpq)$_2$Cl]$_2$ obtained in the step 2, 0.21 ml of acetylacetone (abbreviated as Hacac), and 0.72 g of sodium carbonate were mixed with each other with 20 ml of 2-ethoxyethanol as a solvent. The solution was refluxed in nitrogen atmosphere for 16 hours to give red powder (yields of 46%). A synthesis scheme of the step 3 (b-3) is represented as follows:

Formula 46

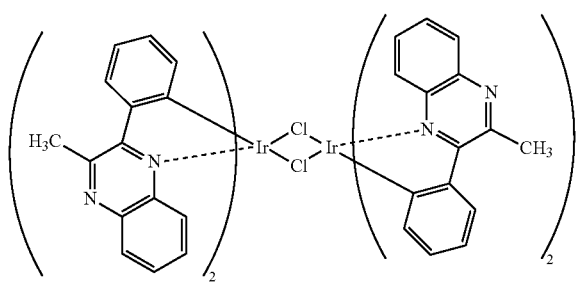

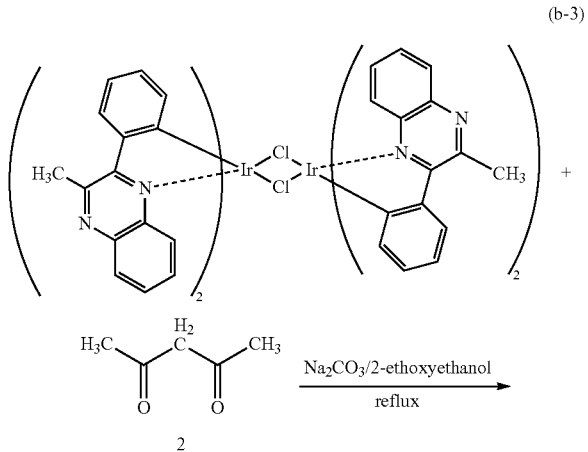

(b-3)

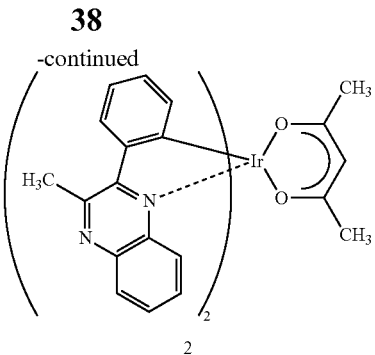

The obtained red powder was analyzed by nuclear magnetic resonance spectroscopy ($^1$H-NMR) and the product was identified to be Ir(mpq)$_2$(acac) which is one of the organometallic complexes according to the present invention. The result was as follows:

$^1$H-NMR. δ (CDCl$_3$): 8.22 (t, 4H), 8.01 (d, 2H), 7.62 (t, 2H), 7.39 (t, 2H), 7.03 (t, 2H), 6.66 (t, 2H), 6.53 (d, 2H), 4.53 (s, 1H), 3.36 (s, 6H), 1.46 (s, 6H).

Decomposition temperature T$_d$ of the obtained Ir(mpq)$_2$(acac) was measured by Thermo-Gravimetric/Differential Thermal Analyzer (from Seiko Instrument Inc., TG/DTA-320 type) and the result was T$_d$=330° C. The result shows that the obtained product shows good heat resistance.

Figure 12:
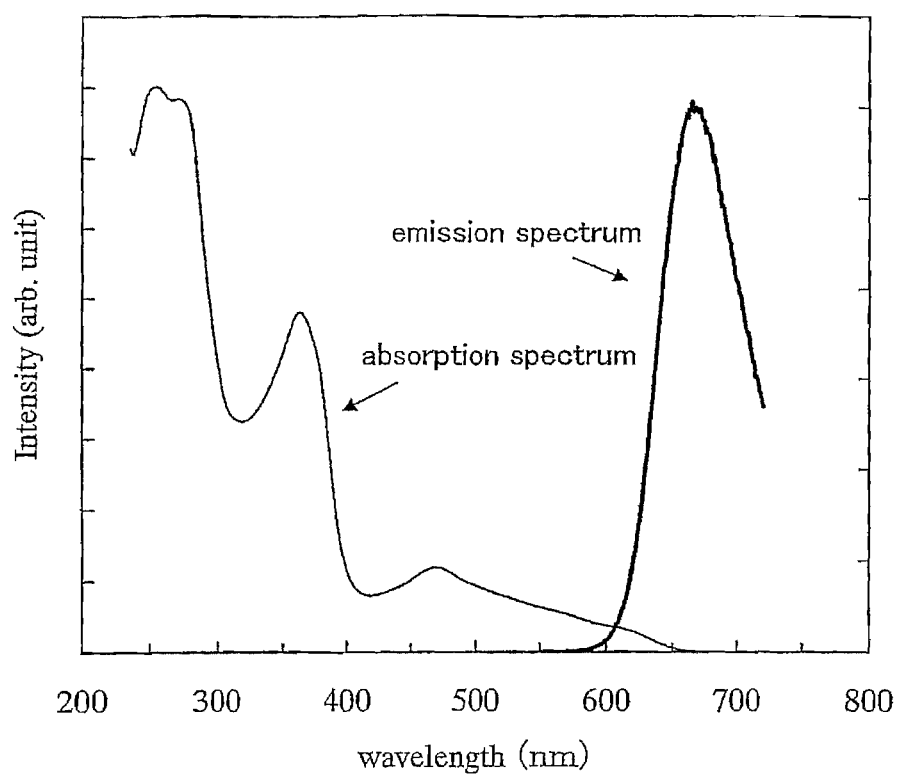
FIG. 12 is a view for showing emission and absorption spectra of $Ir(mpq)_2(acac)$ which is one of organometallic complexes according to the present invention.

FIG. 12 shows an absorption spectrum and an emission spectrum (Photo Luminescence) of the obtained Ir(mpq)$_2$(acac) in dichloromethane. The emission spectrum was obtained when using light at a wavelength of 469 nm taken out by spectroscopy of halogen lamp light by slit as exciting light. In FIG. 12, an abscissa axis represents a wavelength (nm), whereas an ordinate axis represents intensity [arbitrary unit (arb. unit)]. As shown in FIG. 12, the Ir(mpq)$_2$(acac), the organometallic complex according to the present invention, has absorption peaks at 362 nm, 469 nm, 565 nm, and 615 nm. The emission spectrum is emission having an emission peak at 665 nm. The emission is visible to be red emission.

The obtained Ir(mpq)$_2$(acac) has a plurality of emission peaks at a long wavelength side. The peaks are absorption specific for an organometallic complex frequently observed in an ortho-metalated complex or the like, which may correspond to singlet MLCT transition, triplet π-π* transition, or triplet MLCT (Metal to ligand charge transfer) transition. Especially, the absorption peak at the longest-wavelength side is broadly skew in a visible region, which shows that the absorption spectrum is an absorption spectrum specific to triplet MLCT transition. Hence, the Ir(mpq)$_2$(acac) is identified to be a compound capable of direct light exciting or intersystem crossing to a triplet excited state.

Further, gas containing oxygen was injected into a dichloromethane solution including the obtained Ir(mpq)$_2$(acac) to examine light intensity of the Ir(mpq)$_2$(acac) dissolved with oxygen is emitted. Argon was injected into a dichloromethane solution including the obtained Ir(mpq)$_2$(acac) to examine light intensity of the light emission which is obtained when making the Ir(mpq)$_2$(acac) dissolved with argon emit light. As a result, light intensity of the light emission derived from the Ir(mpq)$_2$(acac) dissolved with argon is stronger than that of the light emission derived from the Ir(mpq)$_2$(acac) dissolved with oxygen. There is the same tendency of a material exhibiting phosphorescence. Therefore, light emission derived from the Ir(mpq)$_2$(acac) is phosphorescence.

SYNTHESIS EXAMPLE 2

A method for synthesizing (acetylacetonato)bis[2-(4-fluorophenyl)-3-methylquinoxalinato]iridium (III) (abbreviated as Ir(MFpq)$_2$(acac)) as represented by a structural formula (19) is explained. A method for synthesizing Ir(MFpq)$_2$(acac) is not limited to this synthesis example. Another synthesis method can be used.

Step 1: Synthesis of a Ligand (HMFpq)

2.04 g of magnesium and 5 ml of tetrahydrofuran (abbreviated as THF) were suspended, and a tiny amount of 1,2-dibromoethane was added to the obtained suspension. Then, a solution of 14.72 g of 4-bromofluorobenzene and 85 ml of THF was dropped to the suspension and stirred under heat-reflux for 30 minutes. 2.13 g of 2-methylquinoxaline is added to the solution cooled to a room temperature. The solution was stirred under heat-reflux for four hours. 10% of hydrochloric acid was added to the solution cooled to a room temperature to fractionate an organic layer with chloroform. After drying with magnesium sulfide, solvent was condensed. By purifying with a column chromatography (dichloromethane), 2-(4-fluorophenyl)-3-methylquixaline (abbreviated as HMfpq) was obtained (beige powder, yields of 20%). A synthesis scheme of the step 1 (c-1) is represented as follows. In this synthesis example, a ligand (Hmfpq) is obtained by the reaction of Grignard reagent of 4-bromofluorobenzene and 2-methylquinoxaline. However, the ligand (HMfpq) can also be obtained by the reaction of 4-bromofluorobenzene which is lithated by alkyllithium or the like and 2-methylquinoxaline. In that case, the HMfpq can be obtained at higher yields than those in this synthesis example.

Formula 47

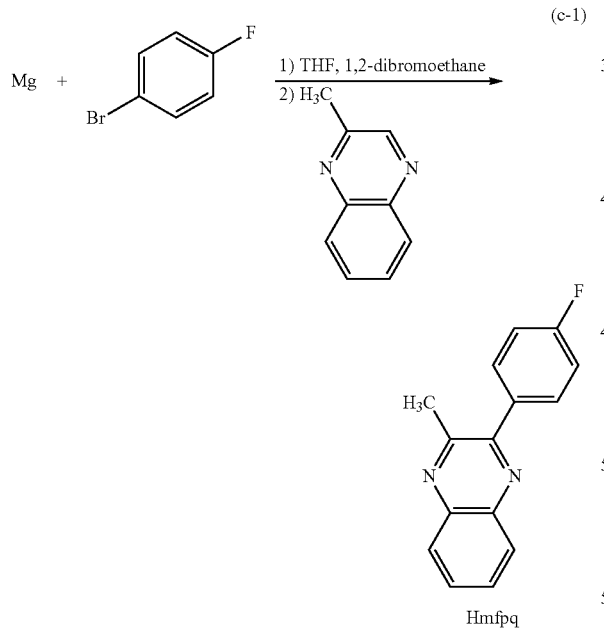

Step 2: Synthesis of Binuclear Complex (Abbreviated as [Ir(MFpq)$_2$Cl]$_2$)

1.60 g of a ligand, Hmqp and 0.80 g of iridium chloride hydrate (IrCl$_3$.H$_2$O) were mixed with each other with a mixed solution of 30 ml of 2-ethoxyethanol and 10 ml of water as a solvent. The solution was refluxed in nitrogen atmosphere for 20 hours to give a binuclear complex (abbreviated as [Ir(MFpg)$_2$Cl]$_2$ (reddish brown powder, yields of 91%). A synthesis scheme of the step 2 (c-2) is represented as follows:

Formula 48

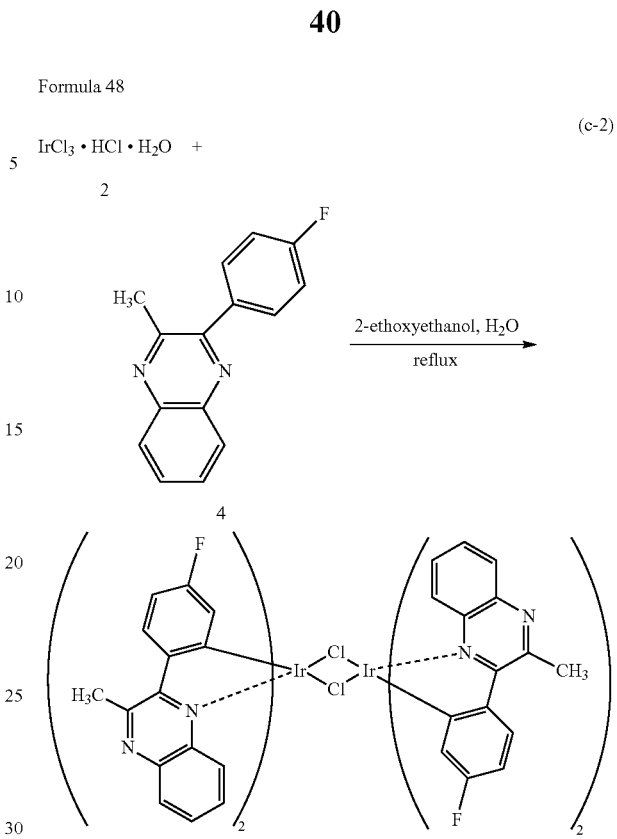

Step 3: Synthesis of Organometallic Compound According to the Present Invention (Ir(MFpq)$_2$(acac))

1.70 g of the [Ir(MFpq)$_2$Cl]$_2$ obtained in the Step 2, 0.37 ml of acetylacetone-(Hacac), and 1.28 g of sodium carbonate were mixed with each other with 30 ml of 2-ethoxyethanol as a solvent. The solution was refluxed in nitrogen atmosphere for 16 hours to give (acetylacetonato)bis[2-(4-fluorophenyl)-3-methylquinoxalineto]iridium (III) (abbreviated as Ir(MFpq)$_2$(acac)) which is the organometallic compound according to the present invention (red powder, yields of 49%). A synthesis scheme of the step 3 (c-3) is represented as follows:

Formula 49

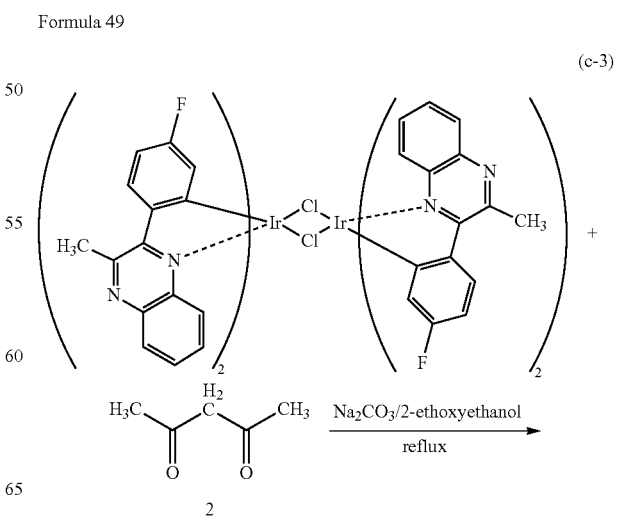

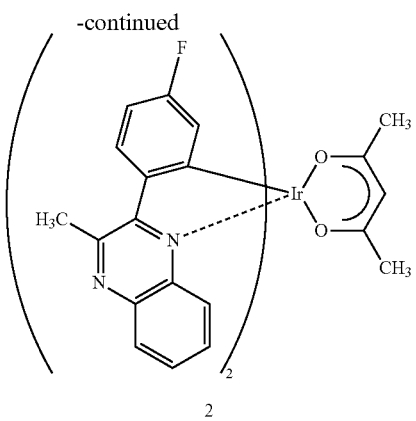

-continued

2

¹H-NMR. δ (CDCl₃): 8.24-8.15 (m, 4H), 8.02 (dd, 2H), 7.64 (m, 2H), 7.42 (m, 2H), 6.75 (td, 2H), 6.15 (dd, 2H), 4.55 (s, 1H), 3.33 (s, 6H), 1.54 (s, 3H), 1.47 (s, 3H).

Decomposition temperature $T_d$ of the obtained Ir(MFpq)₂(acac) which is the organometallic compound according to the present invention was measured by TG/DTA and the result was $T_d$=330° C. The result shows that the obtained product shows good heat resistance.

Figure 41:
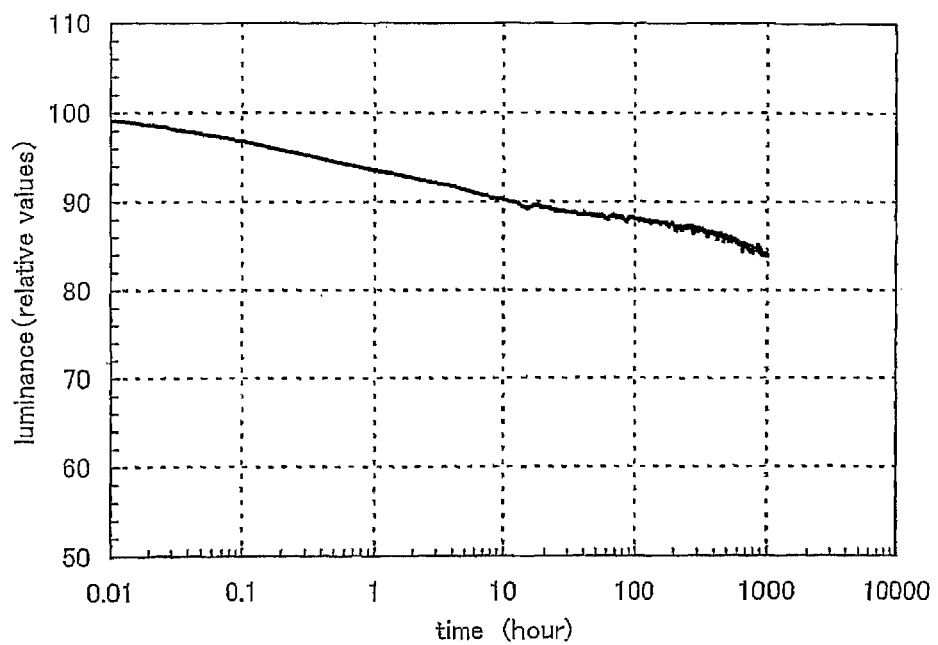
FIG. 41 is a view for showing emission and absorption spectra of $Ir(MFpq)_2(acac)$ which is one of organometallic complexes according to the present invention.

FIG. 41 shows an absorption spectrum and an emission spectrum (PL) of the obtained Ir(MFpq)₂(acac) in dichloromethane. The organometallic compound according to the present invention, Ir(MFpq)₂(acac), has absorption peaks at 595 nm (sh), 547 nm (sh), 464 m, and 363 nm. The emission spectrum was red emission having an emission peak at 633 nm.

SYNTHESIS EXAMPLE 3

A method for synthesizing (acetylacetonato)(2-methyl-3-phenylquinoxalinato) platinum (II) [abbreviated as Pt(mpq)(acac)] as represented by the following structural formula (50), which is one of organometallic compounds represented by general formulae (1) to (4) is explained. A method for synthesizing Pt(mpq)(acac) is not limited to this synthesis example. Another synthesis method can be used. The synthesis method of 2-methyl-3-phenylquinoxaline (abbreviated as Hmpq) which is a ligand employed in this synthesis method is not further explained here since it was explained in the synthesis method 1.

Formula 50

(50)

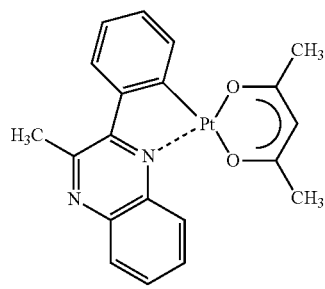

1.53 g of a ligand, Hmqp and 1.15 g of potassium tetrachloro platinate (K₂[PtCl₄]) were mixed with each other with a mixed solution of 30 ml of 2-ethoxyethanol and 10 ml of water as a solvent. The solution was refluxed in nitrogen atmosphere for 16 hours. The solvent was removed from a reaction system. 0.43 ml of acetylacetone (Hacac) and 1.47 g of sodium carbonate were mixed with each other with 30 ml of 2-ethoxyethanol as a solvent. The mixed solution was refluxed in nitrogen atmosphere for 16 hours to give the organometallic compound according to the present invention, Pt(mpq)(acac) (orange powder, yields of 8%). A synthesis scheme (d-1) of this synthesis is represented as follows:

Formula 51

(d-1)

K₂[PtCl₄] +

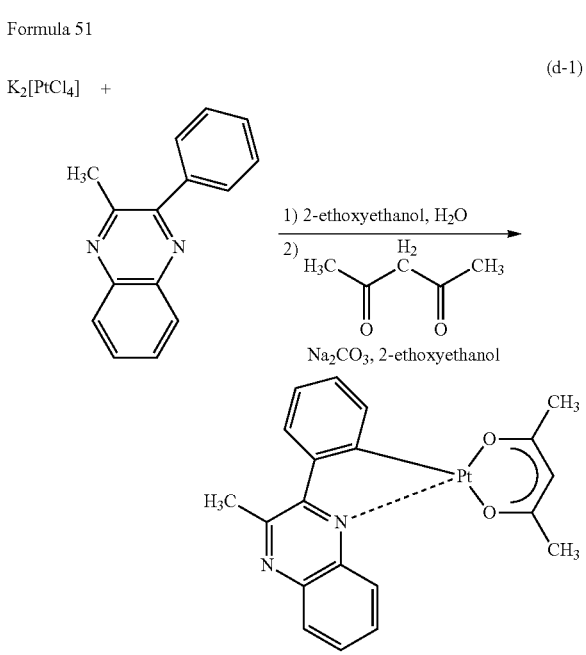

¹H-NMR. δ (CDCl₃): 9.31 (m, 1H), 7.92 (m, 2H), 7.86 (dd, 2H), 7.71 (m, 2H), 7.28 (m, 1H), 7.20 (m, 1H), 5.57 (s, 1H), 3.18 (s, 3H), 2.08 (s, 3H), 2.03 (s, 3H).

Decomposition temperature $T_d$ of the obtained [Pt(mpq)(acac)] which is the organometallic compound according to the present invention was measured by TG/DTA and the result was $T_d$=237° C. The result shows that the obtained product shows good heat resistance.

Figure 42:
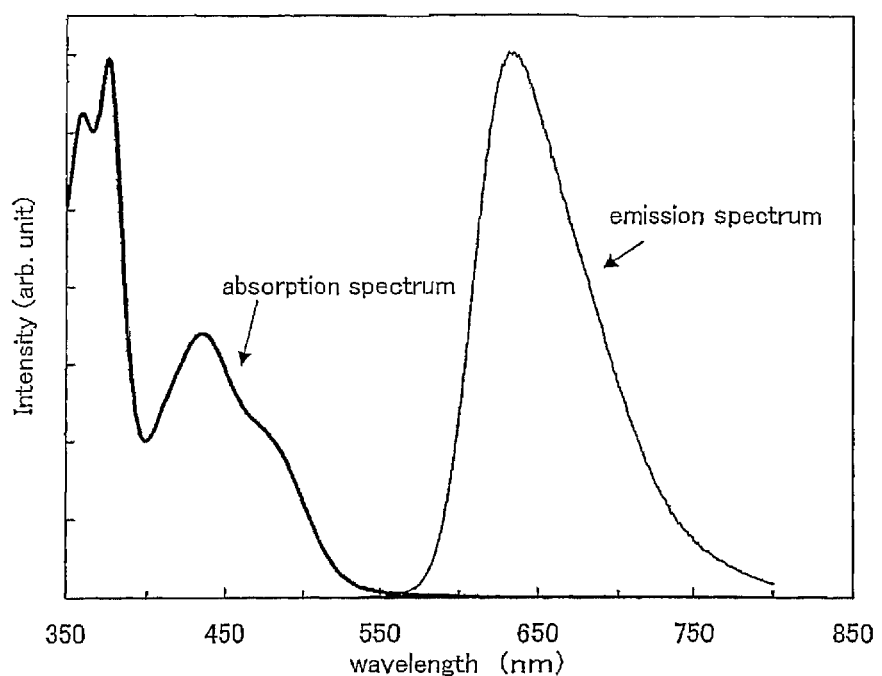
FIG. 42 is a view for showing emission and absorption spectra of $Pt(mpq)(acac)$ which is one of organometallic complexes according to the present invention.

FIG. 42 shows an absorption spectrum and an emission spectrum (PL) of the obtained Pt(mpq)(acac) in dichloromethane. The organometallic compound according to the present invention, Pt(mpq)(acac), has absorption peaks at 530 nm (sh), 482 nm (sh), 435 m, 376 nm, 360 nm, and 344 nm (sh). The emission spectrum was red emission having an emission peak at 632 nm.

EXAMPLE 2

In this example, a manufacturing method and an operation characteristic of a light-emitting element employing Ir(mpq)₂(acac) synthesized in Synthesis Example 1 as a light-emitting substance are explained with reference to FIGS. 13 to 17.

Figure 13:
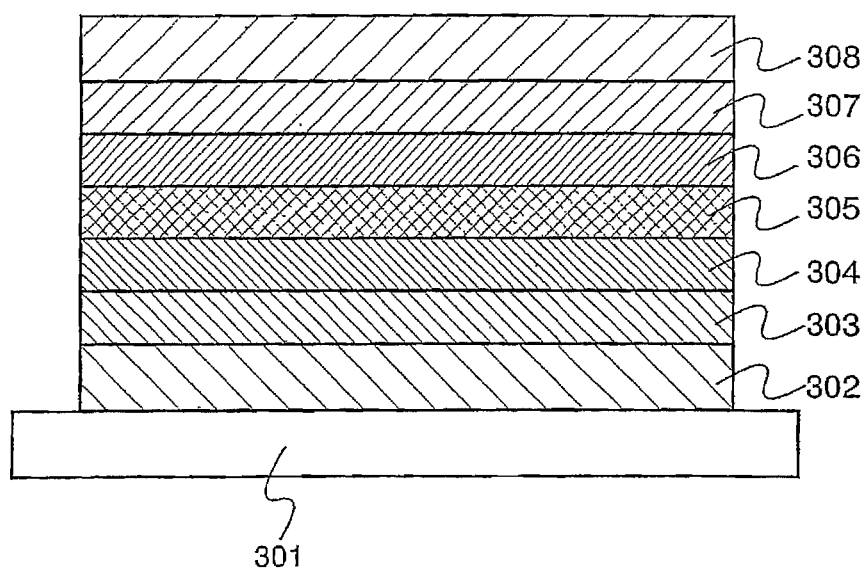
FIG. 13 is an explanatory view for showing a method for manufacturing a light-emitting element according to the present invention.

As shown in FIG. 13, a first electrode 302 is formed by depositing indium tin oxide containing silicon oxide by a sputtering method over a glass substrate 301. The first electrode 302 is formed to have a thickness of 110 nm.

Then, the glass substrate 301 provided with the first electrode 302 is secured to a holder installed in a vacuum-deposition apparatus so that a face provided with the first electrode 302 of the glass substrate 301 is face down.

After reducing pressure in the vacuum-deposition apparatus to 1×10⁻⁴ Pa, a first layer 303 is formed from DNTPD over the first electrode 302. The first layer 303 is formed to have a thickness of 50 nm. The first layer 303 serves as a hole injecting layer when operating the light-emitting element.

Then, a second layer 304 is formed from NPB by a vapor deposition method over the first layer 303. The second layer 304 is formed to have a thickness of 10 nm. The second layer 304 serves as a hole transporting layer when operating the light-emitting element.

And then, a third layer 305 containing CBP and Ir(mpq)$_2$(acac) is formed by a co-evaporation method. The third layer 305 is formed to have a thickness of 30 nm and to have a mass ratio between CBP and Ir(mpq)$_2$(acac) of 1:0.08. Therefore, Ir(mpq)$_2$(acac) is contained in a layer having a matrix of CBP. The third layer 305 serves as a light-emitting layer when operating the light-emitting element. In that case, Ir(mpq)$_2$(acac) is referred to as a guest, whereas CBP is referred to as a host.

A fourth layer 306 is formed from BCP by a vapor deposition method over the third layer 305. The fourth layer 306 is fowled to have a thickness of 10 nm. The fourth layer 306 serves as an electron transporting layer when operating the light-emitting element. An electron transporting layer which has a larger ionization potential than that of the host and which has a function of preventing holes from penetrating from a layer serving as a light-emitting layer (the third layer 305 in this example) to an electrode serving as a cathode (a second electrode 308 in this example) may be especially referred to as a hole blocking layer.

A fifth layer 307 containing Alq$_3$ and Li is formed by a co-evaporation method over a fourth layer 306. She fifth layer 307 was formed to have a thickness of 55 nm and to have a mass ratio between Alq$_a$ and Li of 1:0.01. The fifth layer 307 serves as an electron injecting layer when operating a light-emitting element.

A second electrode 308 made from aluminum is formed over the fifth layer 307. The second electrode 308 is formed to have a thickness of 200 nm.

The light-emitting element manufactured as noted above emits light in the following procedure: current is flown when voltage is applied to the light-emitting element so that electric potential of the first electrode 302 is higher than that of the second electrode 308, and electrons and holes are recombined within the third layer 305 serving as a light-emitting layer to generate excited energy, then, excited Ir(mpq)$_2$(acac) emits light while returning to the ground state.

The light-emitting element is sealed without exposing to the air under nitrogen atmosphere in a glove box. Then, operation characteristics of the light-emitting element are measured. The measurement is carried out at a room temperature (in the atmosphere kept at 25° C.).

Figure 14:
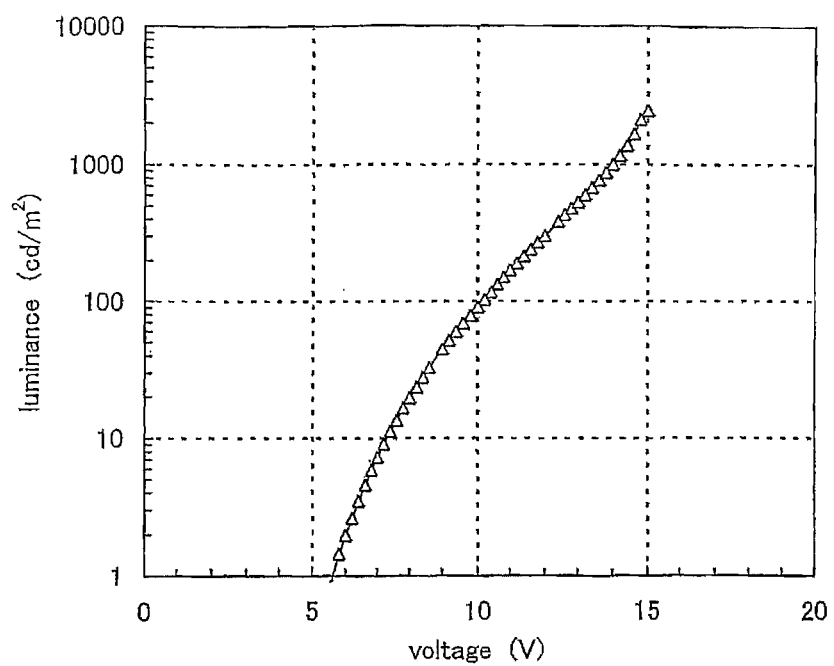
FIG. 14 is a view for showing a voltage-luminance characteristic of a light-emitting element according to Example 2.
Figure 15:
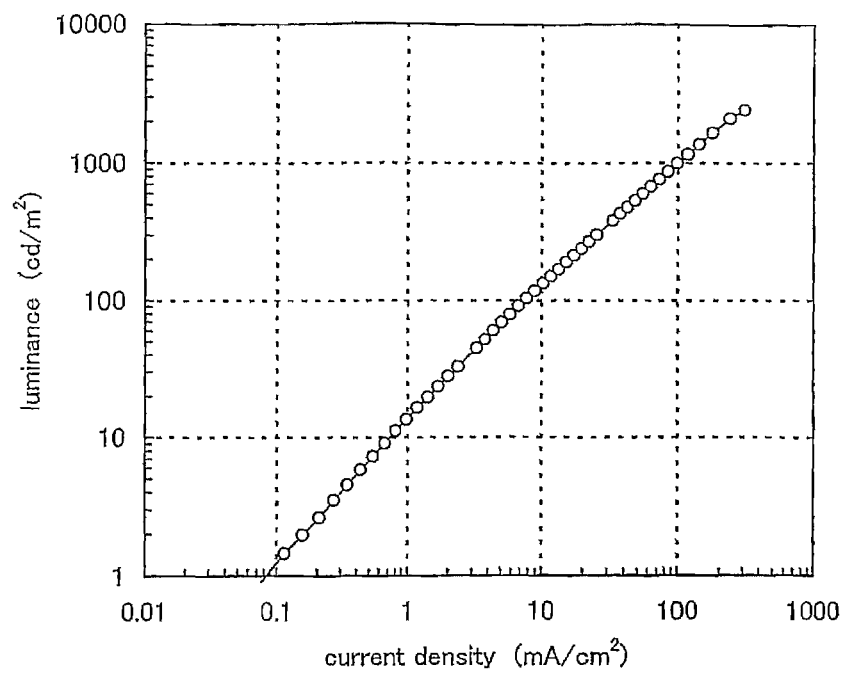
FIG. 15 is a view for showing a current density-luminance characteristic of a light-emitting element according to Example 2.
Figure 16:
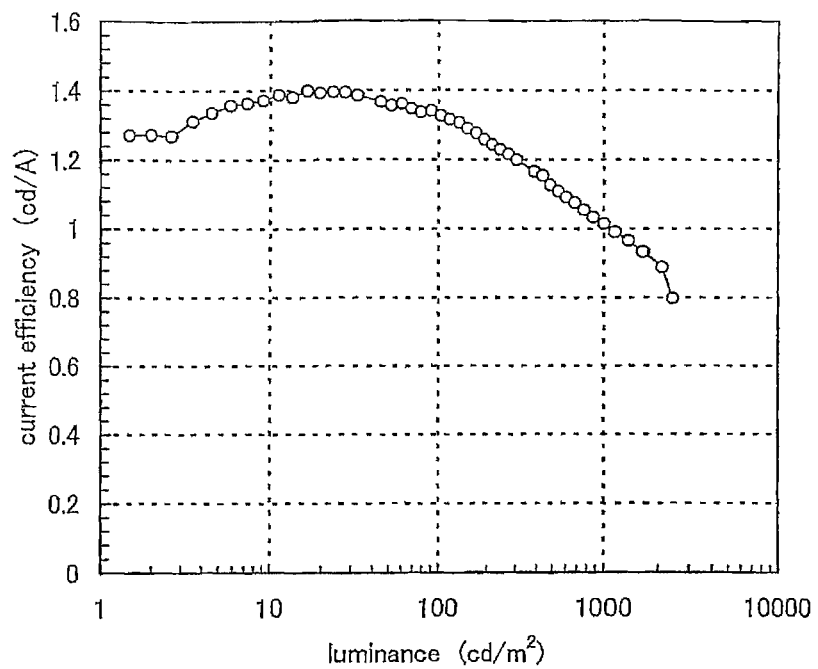
FIG. 16 is a view for showing a luminance-current efficiency characteristic of a light-emitting element according to Example 2.

FIGS. 14 to 16 are measurement results. FIG. 14 shows a measurement result of voltage-luminance characteristics, FIG. 15 shows a measurement result of current density-luminance characteristics, and FIG. 16 shows a measurement result of luminance-current efficiency characteristics. In FIG. 14, an abscissa axis represents voltage (V), whereas an ordinate axis represents luminance (cd/m²). In FIG. 15, an abscissa axis represents current density (mA/cm²), whereas an ordinate axis represents luminance (cd/m²). In FIG. 16, an abscissa axis represents luminance (cd/m²), whereas an ordinate axis represents current efficiency (cd/A). From these results, the light-emitting element according to this example emits light at current density of 42.3 mA/cm² and luminance of 480 cd/m² at an applied voltage of 12.8 V. The light-emitting element indicates good levels of current efficiency of 1.1 cd/A and external quantum efficiency of 7.8%.

Figure 17:
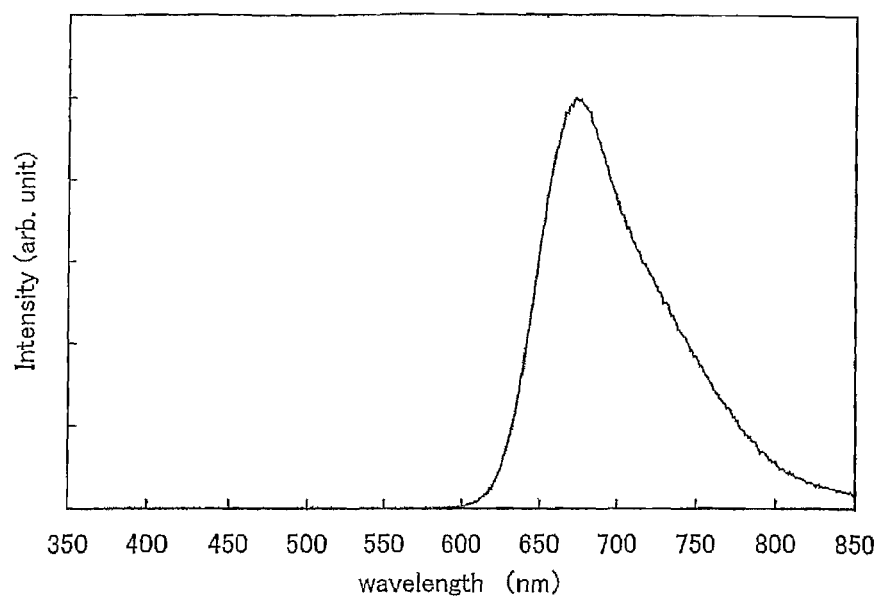
FIG. 17 is a view for showing an emission spectrum of a light-emitting element according to Example 2.

FIG. 17 shows an emission spectrum of the light-emitting element manufactured in this example. In FIG. 17, an abscissa axis represents a wavelength (nm), whereas an ordinate axis represents intensity (arbitrary unit). As shown in FIG. 17, the light-emitting element according to this example has a peak of the emission spectrum at 672 nm and exhibits light emission derived from Ir(mpq)$_2$(acac) with the chromaticity coordinates x=0.74, y=0.26 in a CIE color coordinate system. Therefore, it can be known that the light-emitting element according to this example exhibits deep red light emission with good color purity.

EXAMPLE 3

In this example, a manufacturing method and an operation characteristic of a light-emitting element employing Ir(mpq)$_2$(acac) synthesized in Synthesis Example 1 as a light-emitting substance are explained with reference to FIGS. 13, 18 to 21.

As shown in FIG. 13, a first electrode 302 is formed by depositing indium tin oxide containing silicon oxide by a sputtering method over a glass substrate 301. The first electrode 302 is fowled to have a thickness of 110 nm.

Then, the glass substrate 301 provided with the first electrode 302 is secured to a holder installed in a vacuum-deposition apparatus so that a face provided with the first electrode 302 of the glass substrate 301 is face down.

After reducing pressure in the vacuum-deposition apparatus to 1×10⁻⁴ Pa, a first layer 303 is formed from DNTPD over the first electrode 302. The first layer 303 is formed to have a thickness of 50 nm. The first layer 303 serves as a hole injecting layer when operating the light-emitting element.

Then, a second layer 304 is formed from NPB by a vapor deposition method over the first layer 303. The second layer 304 is formed to have a thickness of 10 nm. The second layer 304 serves as a hole transporting layer when operating the light-emitting element.

And then, a third layer 305 containing NPB and Ir(mpq)$_2$(acac) is formed by a co-evaporation method. The third layer 305 is formed to have a thickness of 30 nm and to have a mass ratio between NPB and Ir(mpq)$_2$(acac) of 1:0.08. Therefore, Ir(mpq)$_2$(acac) is contained in a layer having a matrix of NPB. The third layer 305 serves as a light-emitting layer when operating the light-emitting element. In that case, Ir(mpq)$_2$(acac) is referred to as a guest, whereas NPB is referred to as a host.

A fourth layer 306 is formed from Alq$_3$ by a vapor deposition method over the third layer 305. The fourth layer 306 is formed to have a thickness of 10 nm. The fourth layer 306 serves as an electron transporting layer when operating the light-emitting element.

A fifth layer 307 containing Alq$_3$ and Li is formed by a co-evaporation method over a fourth layer 306. The fifth layer 307 was formed to have a thickness of 55 nm and to have a mass ratio between Alq$_3$ and Li of 1:0.01. The fifth layer 307 serves as an electron injecting layer when operating a light-emitting element.

A second electrode 308 made from aluminum is formed over the fifth layer 307. The second electrode 308 is formed to have a thickness of 200 nm.

The light-emitting element manufactured as noted above emits light in the following procedure: current is flown when voltage is applied to the light-emitting element so that electric potential of the first electrode 302 is higher than that of the second electrode 308, and electrons and holes are recombined within the third layer 305 serving as a light-emitting layer to generate excited energy, then, excited Ir(mpq)$_2$(acac) emits light while returning to the ground state.

The light-emitting element is sealed without exposing to the air under nitrogen atmosphere in a glove box. Then, operation characteristics of the light-emitting element are measured. The measurement is carried out at a room temperature (in the atmosphere kept at 25° C.).

Figure 18:
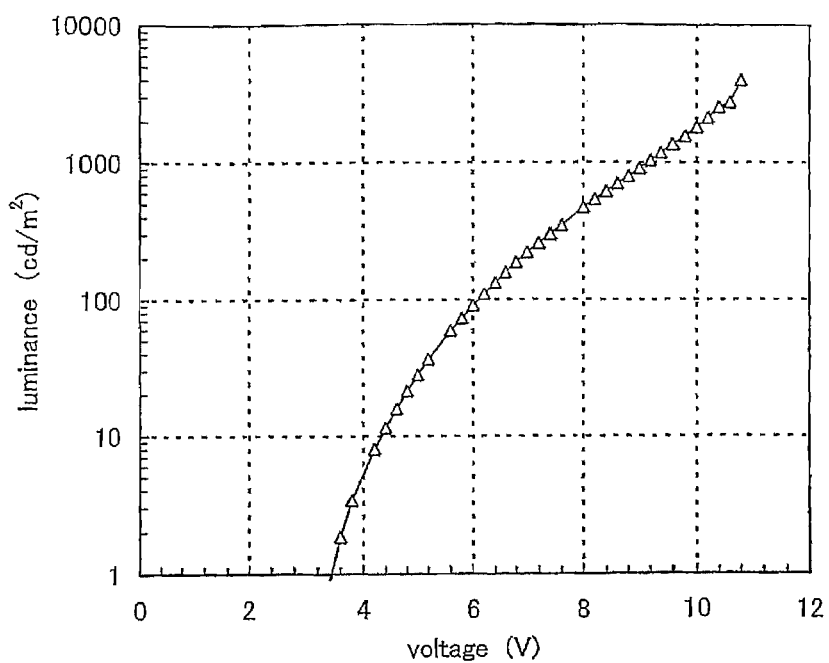
FIG. 18 is a view for showing a voltage-luminance characteristic of a light-emitting element according to Example 3.
Figure 19:
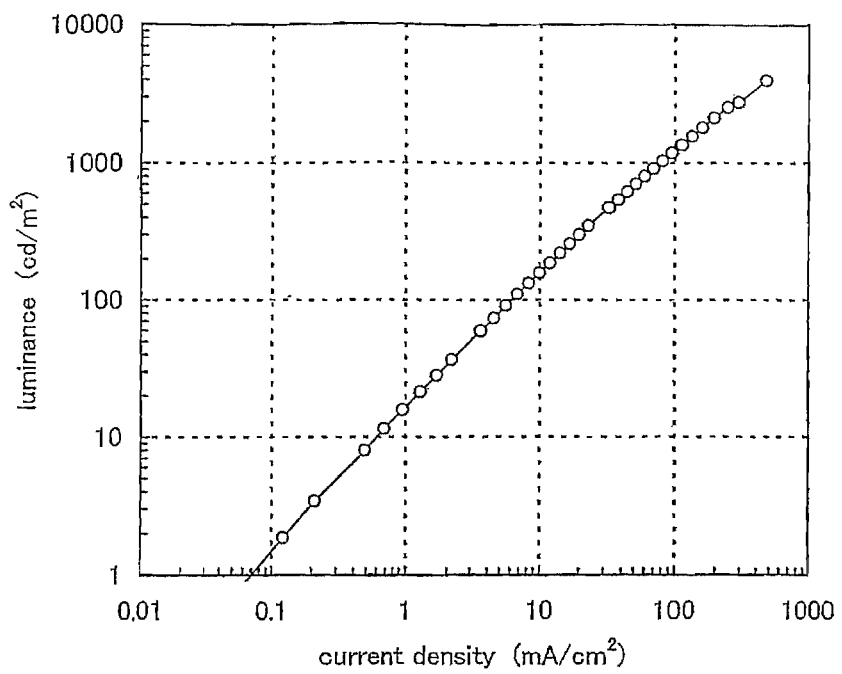
FIG. 19 is a view for showing a current density-luminance characteristic of a light-emitting element according to Example 3.
Figure 20:
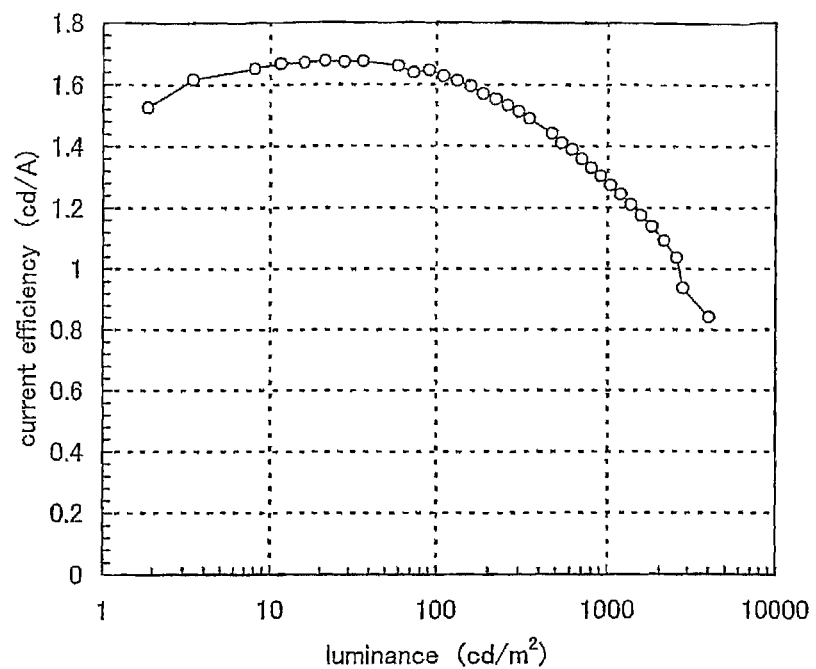
FIG. 20 is a view for showing a luminance-current efficiency characteristic of a light-emitting element according to Example 3.

FIGS. 18 to 20 are measurement results. FIG. 18 shows a measurement result of voltage-luminance characteristics, FIG. 19 shows a measurement result of current density-luminance characteristics, and FIG. 20 shows a measurement result of luminance-current efficiency characteristics. In FIG. 18, an abscissa axis represents voltage (V), whereas an ordinate axis represents luminance (cd/m$^2$). In FIG. 19, an abscissa axis represents current density (mA/cm$^2$), whereas an ordinate axis represents luminance (cd/m$^2$). In FIG. 20, an abscissa axis represents luminance (cd/m$^2$), whereas an ordinate axis represents current efficiency (cd/A). From these results, the light-emitting element according to this example emits light at current density of 32.8 mA/cm$^2$ and luminance of 470 cd/m$^2$ at an applied voltage of 8.0 V. The light-emitting element indicates good levels of current efficiency of 1.4 cd/A and external quantum efficiency of 9.0%.

Figure 21:
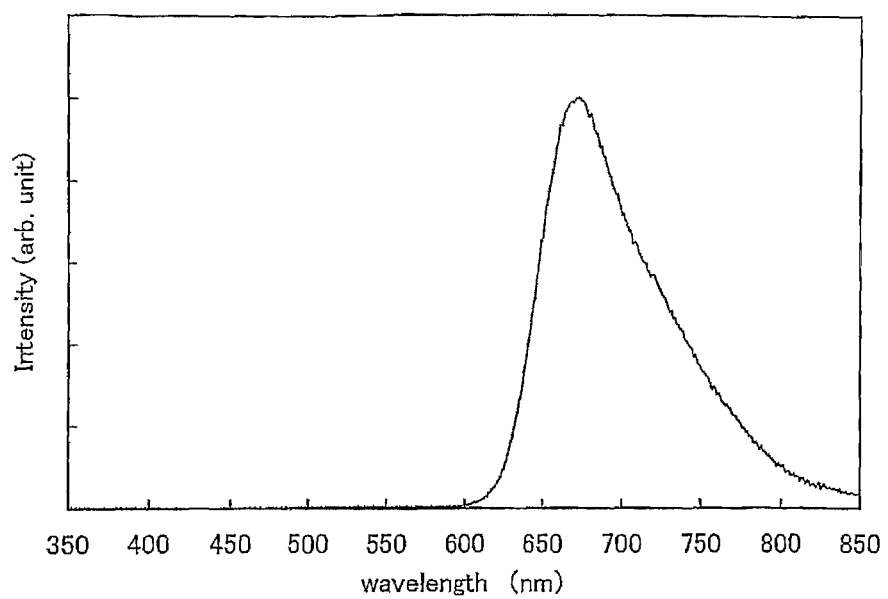
FIG. 21 is a view for showing an emission spectrum of a light-emitting element according to Example 3.

FIG. 21 shows an emission spectrum of the light-emitting element manufactured in this example. In FIG. 21, an abscissa axis represents a wavelength (nm), whereas an ordinate axis represents intensity (arbitrary unit). As shown in FIG. 21, the light-emitting element according to this example has a peak of the emission spectrum at 673 nm and exhibits light emission derived from Ir(mpq)$_2$(acac) with the chromaticity coordinates x=0.73, y=0.27 in a CIE color coordinate system. Therefore, it can be known that the light-emitting element according to this example exhibits deep red light emission with good color purity.

Figure 22:
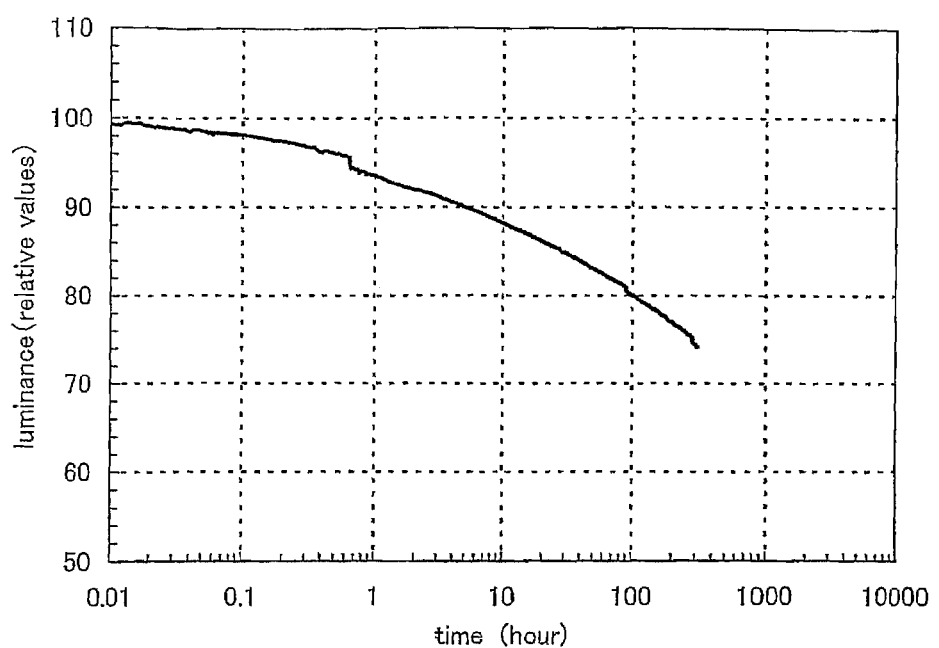
FIG. 22 is a view for showing changes in luminance with emission time of a light-emitting element according to Example 3.

The variation in luminance with light-emitting time (lifetime characteristic) of the light-emitting element manufactured according to this example is measured. The measurement was carried out in the way that current at a current value required for light emission at a luminance of 470 cd/m$^2$ is applied to the light-emitting element to achieve light emission and the luminance is measured at any given points in time. In FIG. 22, an abscissa axis represents light-emitting time (hour), whereas an ordinate axis represents relative values (no unit) against luminance at an initial state assuming that the luminance at the initial state is 100. As shown in FIG. 22, it can be predicted that a half-value period of the light-emitting element according to the present invention is approximate 10,000 hours. Therefore, the light-emitting element according to the present invention shows a favorable lifetime characteristic and has high reliability.

EXAMPLE 4

In this example, a manufacturing method and an operation characteristic of a light-emitting element employing Ir(mpq)$_2$(acac) synthesized in Synthesis Example 1 as a light-emitting substance are explained with reference to FIGS. 13, 23 to 27.

As shown in FIG. 13, a first electrode 302 is formed by depositing indium tin oxide containing silicon oxide by a sputtering method over a glass substrate 301. The first electrode 302 is formed to have a thickness of 110 nm.

Then, the glass substrate 301 provided with the first electrode 302 is secured to a holder installed in a vacuum-deposition apparatus so that a face provided with the first electrode 302 of the glass substrate 301 is face down.

After reducing pressure in the vacuum-deposition apparatus to 1×10$^{-4}$ Pa, a first layer 303 is formed from DNTPD over the first electrode 302. The first layer 303 is formed to have a thickness of 50 nm. The first layer 303 serves as a hole injecting layer when operating the light-emitting element.

Then, a second layer 304 is formed from NPB by a vapor deposition method over the first layer 303. The second layer 304 is formed to have a thickness of 10 nm. The second layer 304 serves as a hole transporting layer when operating the light-emitting element.

And then, a third layer 305 containing Alq$_3$ and Ir(mpq)$_2$(acac) is formed by a co-evaporation method. The third layer 305 is formed to have a thickness of 30 nm and to have a mass ratio between Alq$_a$ and Ir(mpq)$_2$(acac) of 1:0.08. Therefore, Ir(mpq)$_2$(acac) is contained in a layer having a matrix of Alq$_3$. The third layer 305 serves as a light-emitting layer when operating the light-emitting element. In that case, Ir(mpq)$_2$(acac) is referred to as a guest, whereas Alq$_3$ is referred to as a host.

A fourth layer 306 is formed from Alq$_3$ by a vapor deposition method over the third layer 305. The fourth layer 306 is formed to have a thickness of 10 nm. The fourth layer 306 serves as an electron transporting layer when operating the light-emitting element.

A fifth layer 307 containing Alq$_a$ and Li is formed by a co-evaporation method over a fourth layer 306. The fifth layer 307 was formed to have a thickness of 55 nm and to have a mass ratio between Alq$_3$ and Li of 1:0.01. The fifth layer 307 serves as an electron injecting layer when operating a light-emitting element.

A second electrode 308 made from aluminum is formed over the fifth layer 307. The second electrode 308 is formed to have a thickness of 200 nm.

The light-emitting element manufactured as noted above emits light in the following procedure: current is flown when voltage is applied to the light-emitting element so that electric potential of the first electrode 302 is higher than that of the second electrode 308, and electrons and holes are recombined within the third layer 305 serving as a light-emitting layer to generate excited energy, then, excited Ir(mpq)$_2$(acac) emits light while returning to the ground state.

The light-emitting element is sealed without exposing to the air under nitrogen atmosphere in a glove box. Then, operation characteristics of the light-emitting element are measured. The measurement is carried out at a room temperature (in the atmosphere kept at 25° C.).

Figure 23:
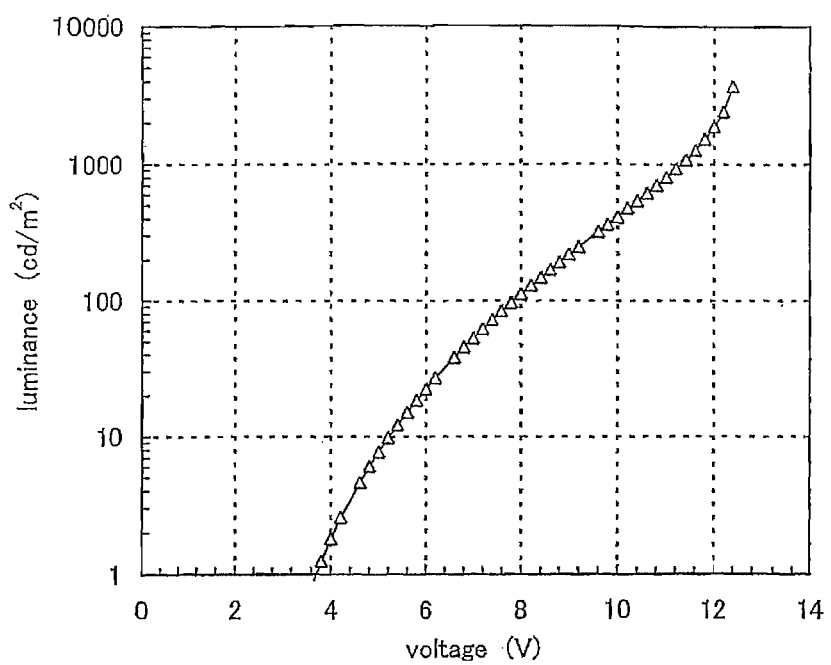
FIG. 23 is a view for showing a voltage-luminance characteristic of a light-emitting element according to Example 4.
Figure 24:
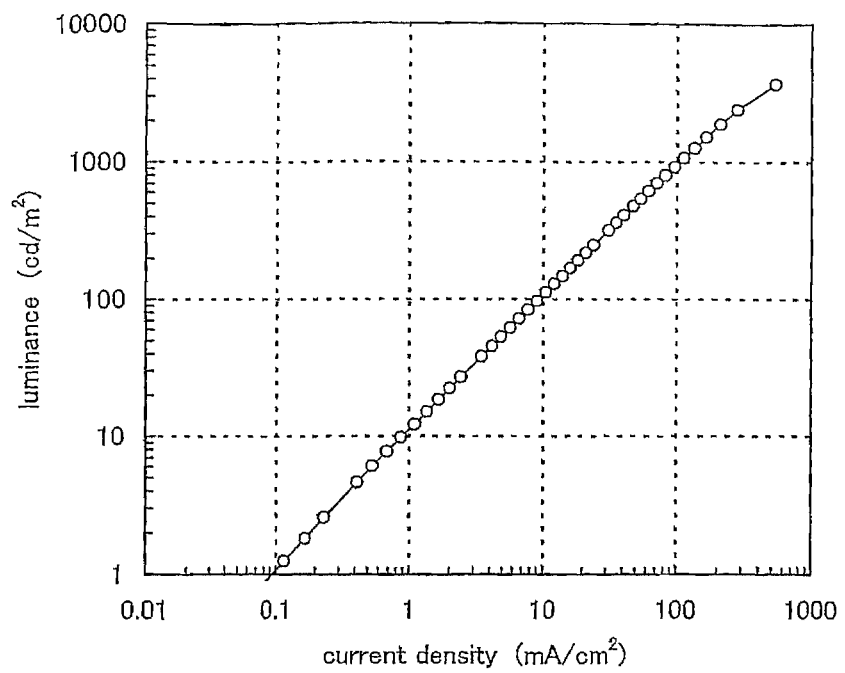
FIG. 24 is a view for showing a current density-luminance characteristic of a light-emitting element according to Example 4.
Figure 25:
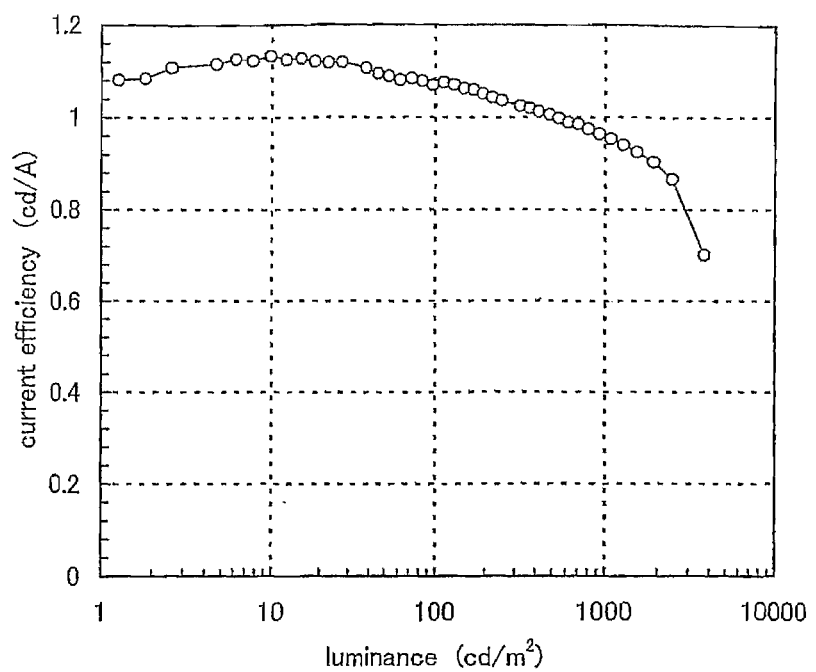
FIG. 25 is a view for showing a luminance-current efficiency characteristic of a light-emitting element according to Example 4.

FIGS. 23 to 25 are measurement results. FIG. 23 shows a measurement result of voltage-luminance characteristics, FIG. 24 shows a measurement result of current density-luminance characteristics, and FIG. 25 shows a measurement result of luminance-current efficiency characteristics. In FIG. 23, an abscissa axis represents voltage (V), whereas an ordinate axis represents luminance (cd/m$^2$). In FIG. 24, an abscissa axis represents current density (mA/cm$^2$), whereas an ordinate axis represents luminance (cd/m$^2$). In FIG. 25, an abscissa axis represents luminance (cd/m$^2$), whereas an ordinate axis represents current efficiency (cd/A). From these results, the light-emitting element according to this example emits light at current density of 47.7 mA/cm$^2$ and luminance of 480 cd/m$^2$ at an applied voltage of 10.2 V. The light-emitting element indicates good levels of current efficiency of 1.0 cd/A and external quantum efficiency of 6.8%.

Figure 26:
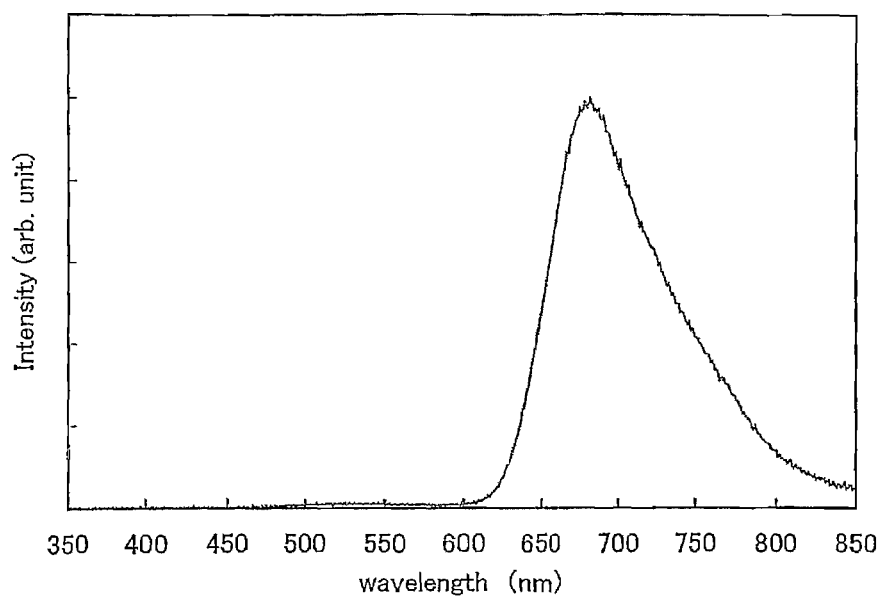
FIG. 26 is a view for showing an emission spectrum of a light-emitting element according to Example 4.

FIG. 26 shows an emission spectrum of the light-emitting element manufactured in this example. In FIG. 26, an abscissa axis represents a wavelength (nm), whereas an ordinate axis represents intensity (arbitrary unit). As shown in FIG. 26, the light-emitting element according to this example has a peak of the emission spectrum at 681 nm and exhibits light emission derived from Ir(mpq)$_2$(acac) with the chromaticity coordinates x=0.69, y=0.30 in a CIE color coordinate system. Therefore, it can be known that the light-emitting element according to this example exhibits red light emission with good color purity.

Figure 27:
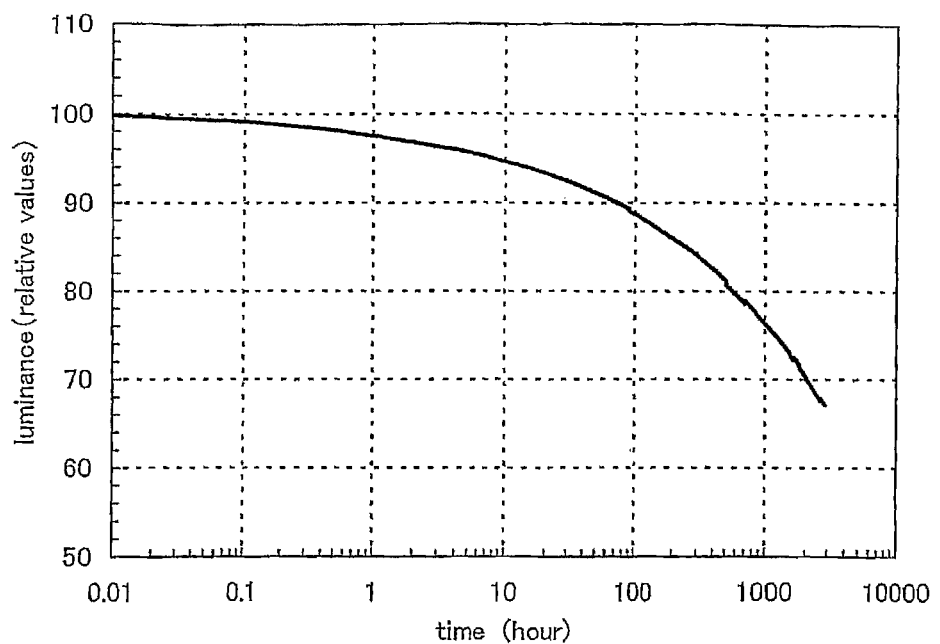
FIG. 27 is a view for showing changes in luminance with emission time of a light-emitting element according to Example 4.

The variation in luminance with light-emitting time (lifetime characteristic) of the light-emitting element manufactured according to this example is measured. The measurement was carried out in the way that current at a current value required for light emission at a luminance of 480 cd/m$^2$ is applied to the light-emitting element to achieve light emission and the luminance is measured at any given points in time. In FIG. 27, an abscissa axis represents light-emitting time (hour), whereas an ordinate axis represents relative values (no unit) against luminance at an initial state assuming that the luminance at the initial state is 100. As shown in FIG. 27, it can be predicted that a half-value period of the light-emitting element according to the present invention is approximate 10,000 hours. Therefore, the light-emitting element according to the present invention shows a favorable lifetime characteristic and has high reliability.

EXAMPLE 5

In this example, a manufacturing method and an operation characteristic of a light-emitting element employing Ir(MFpq)$_2$(acac) synthesized in Synthesis Example 2 as a light-emitting substance are explained with reference to FIGS. 13, 28 to 31.

As shown in FIG. 13, a first electrode 302 is fowled by depositing indium tin oxide containing silicon oxide by a sputtering method over a glass substrate 301. The first electrode 302 is formed to have a thickness of 110 nm.

Then, the glass substrate 301 provided with the first electrode 302 is secured to a holder installed in a vacuum-deposition apparatus so that a face provided with the first electrode 302 of the glass substrate 301 is face down.

After reducing pressure in the vacuum-deposition apparatus to 1×10$^{-4}$ Pa, a first layer 303 is formed from NBP and molybdenum trioxide by co-evaporation over the first electrode 302. The first layer 303 is formed to have a thickness of 50 nm. The mass ratio between NBP and molybdenum trioxide is 4:1. The first layer 303 serves as a hole injecting layer when operating the light-emitting element.

Then, a second layer 304 is formed from NPB by a vapor deposition method over the first layer 303. The second layer 304 is formed to have a thickness of 10 nm.

The second layer 304 serves as a hole transporting layer when operating the light-emitting element.

And then, a third layer 305 containing CBP and Ir(MFpq)$_2$(acac) is formed by a co-evaporation method. The third layer 305 is formed to have a thickness of 30 nm and to have a mass ratio between CBP and Ir(MFpq)$_2$(acac) of 1:0.08. Therefore, Ir(MFpq)$_2$(acac) is contained in a layer having a matrix of CBP. The third layer 305 serves as a light-emitting layer when operating the light-emitting element. In that case, Ir(MFpq)$_2$(acac) is referred to as a guest, whereas CBP is referred to as a host.

A fourth layer 306 is formed from BCP by a vapor deposition method over the third layer 305. The third layer 305 is formed to have a thickness of 10 nm. The third layer 305 serves as an electron transporting layer when operating the light-emitting element.

A fifth layer 307 containing Alq$_3$ and Li is faulted by a co-evaporation method over a fourth layer 306. The fifth layer 307 was formed to have a thickness of 55 nm and to have a mass ratio between Alq$_3$ and Li of 1:0.01. The fifth layer 307 serves as an electron injecting layer when operating a light-emitting element.

A second electrode 308 made from aluminum is formed over the fifth layer 307. The second electrode 308 is formed to have a thickness of 200 nm.

The light-emitting element manufactured as noted above emits light in the following procedure: current is flown when voltage is applied to the light-emitting element so that electric potential of the first electrode 302 is higher than that of the second electrode 308, and electrons and holes are recombined within the third layer 305 serving as a light-emitting layer to generate excited energy, then, excited Ir(MFpq)$_2$(acac) emits light while returning to the ground state.

The light-emitting element is sealed without exposing to the air under nitrogen atmosphere in a glove box. Then, operation characteristics of the light-emitting element are measured. The measurement is carried out at a room temperature (in the atmosphere kept at 25° C.).

Figure 28:
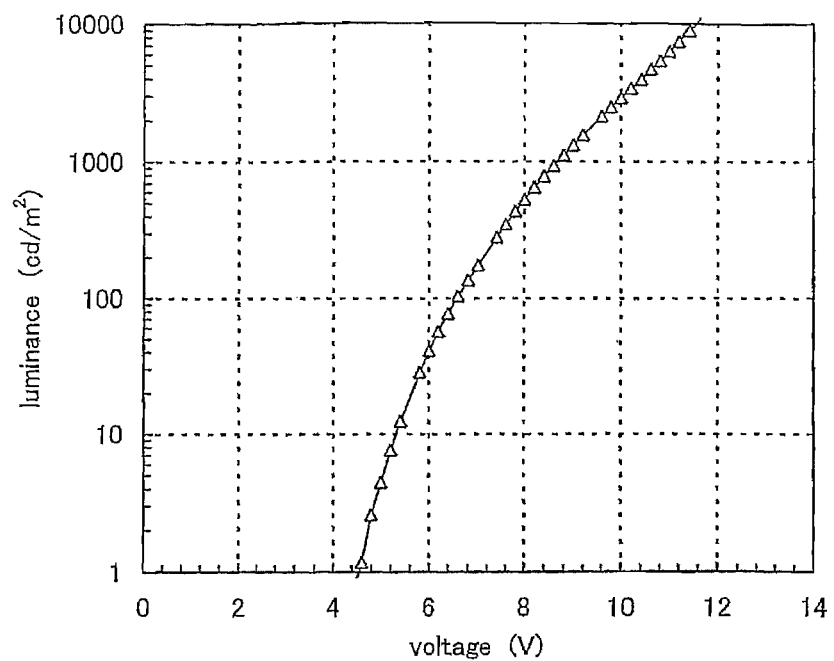
FIG. 28 is a view for showing a voltage-luminance characteristic of a light-emitting element according to Example 5.
Figure 29:
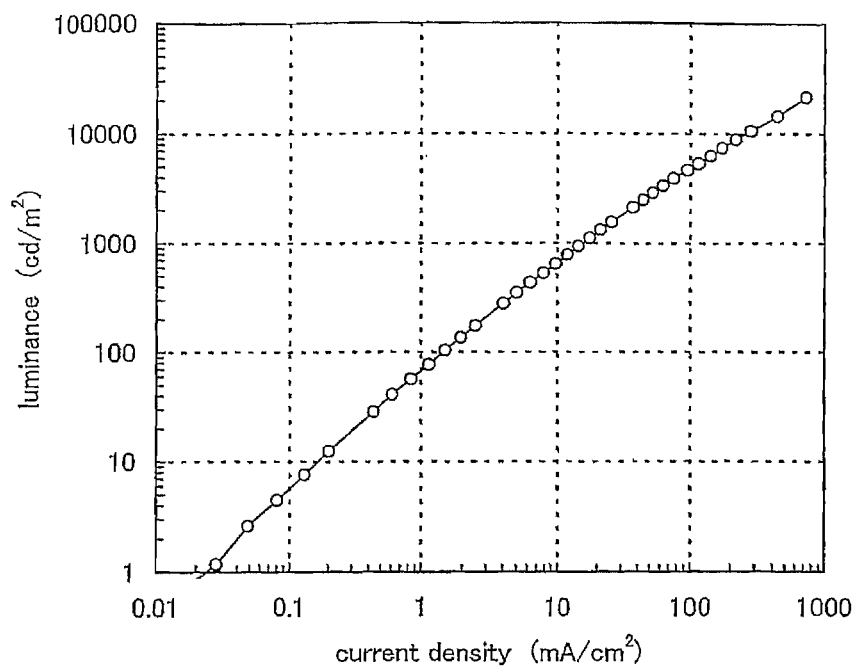
FIG. 29 is a view for showing a current density-luminance characteristic of a light-emitting element according to Example 5.
Figure 30:
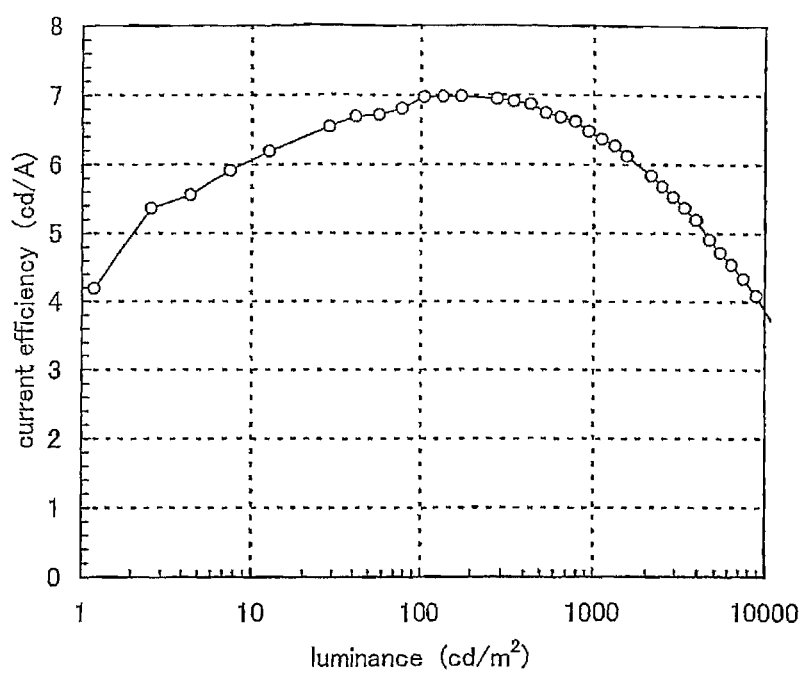
FIG. 30 is a view for showing a luminance-current efficiency characteristic of a light-emitting element according to Example 5.

FIGS. 28 to 30 are measurement results. FIG. 28 shows a measurement result of voltage-luminance characteristics, FIG. 29 shows a measurement result of current density-luminance characteristics, and FIG. 30 shows a measurement result of luminance-current efficiency characteristics. In FIG. 28, an abscissa axis represents voltage (V), whereas an ordinate axis represents luminance (cd/m$^2$). In FIG. 29, an abscissa axis represents current density (mA/cm$^2$), whereas an ordinate axis represents luminance (cd/m$^2$). In FIG. 30, an abscissa axis represents luminance (cd/m$^2$), whereas an ordinate axis represents current efficiency (cd/A). From these results, the light-emitting element according to this example emits light at current density of 14.4 mA/cm$^2$ and luminance of 930 cd/m$^2$ at an applied voltage of 8.6 V. The light-emitting element indicates good levels of current efficiency of 6.5 cd/A and external quantum efficiency of 11%.

Figure 31:
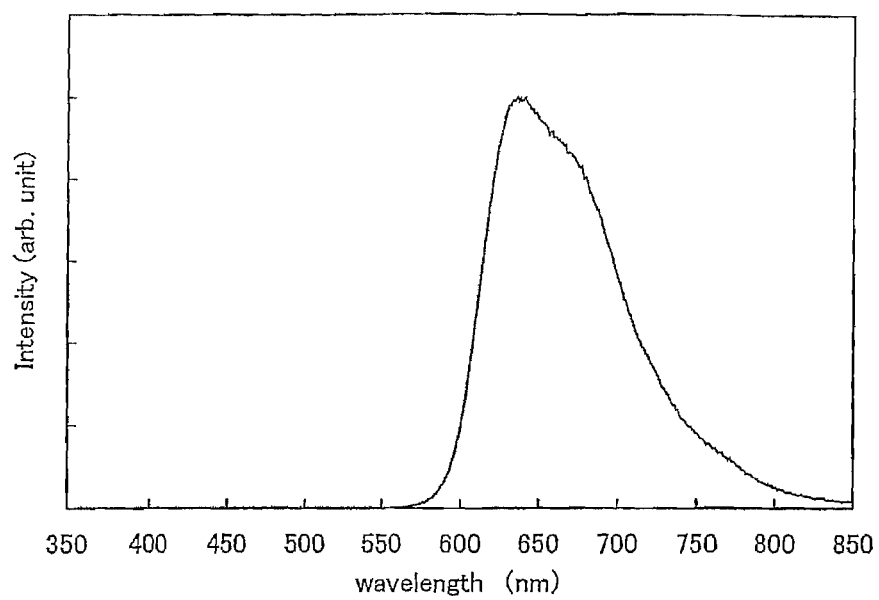
FIG. 31 is a view for showing an emission spectrum of a light-emitting element according to Example 5.

FIG. 31 shows an emission spectrum of the light-emitting element manufactured in this example. In FIG. 31, an abscissa axis represents a wavelength (nm), whereas an ordinate axis represents intensity (arbitrary unit). As shown in FIG. 31, the light-emitting element according to this example has a peak of the emission spectrum at 681 nm and exhibits light emission derived from Ir(MFpq)$_2$(acac) with the chromaticity coordinates x=0.70, y=0.30 in a CIE color coordinate system. Therefore, it can be known that the light-emitting element according to this example exhibits red light emission with good color purity.

EXAMPLE 6

In this example, a manufacturing method and an operation characteristic of a light-emitting element employing Ir(MFpq)$_2$(acac) synthesized in Synthesis Example 2 as a light-emitting substance are explained with reference to FIGS. 13, 32 to 34.

As shown in FIG. 13, a first electrode 302 is formed by depositing indium tin oxide containing silicon oxide by a sputtering method over a glass substrate 301. The first electrode 302 is formed to have a thickness of 110 nm.

Then, the glass substrate 301 provided with the first electrode 302 is secured to a holder installed in a vacuum-deposition apparatus so that a face provided with the first electrode 302 of the glass substrate 301 is face down.

After reducing pressure in the vacuum-deposition apparatus to 1×10$^{-4}$ Pa, a first layer 303 is formed from DNTPD and molybdenum trioxide by co-evaporation over the first electrode 302. The first layer 303 is formed to have a thickness of 50 nm. The mass ratio between NBP and molybdenum trioxide is 4:2. The first layer 303 serves as a hole injecting layer when operating the light-emitting element.

Then, a second layer 304 is formed from NPB by a vapor deposition method over the first layer 303. The second layer 304 is formed to have a thickness of 10 nm. The second layer 304 serves as a hole transporting layer when operating the light-emitting element.

And then, a third layer 305 containing NPB and Ir(MFpq)$_2$(acac) is formed by a co-evaporation method. The third layer 305 is formed to have a thickness of 30 nm and to have a mass ratio between NPB and Ir(MFpq)$_2$(acac) of 1:0.1. Therefore, Ir(MFpq)$_2$(acac) is contained in a layer having a matrix of NPB. The third layer 305 serves as a light-emitting layer when operating the light-emitting element. In that case, Ir(MFpq)$_2$(acac) is referred to as a guest, whereas NPB is referred to as a host.

A fourth layer 306 is formed from Alq$_3$ by a vapor deposition method over the third layer 305. The third layer 305 is formed to have a thickness of 10 nm. The third layer 305 serves as an electron transporting layer when operating the light-emitting element.

A fifth layer 307 containing Alq$_3$ and Li is formed by a co-evaporation method over a fourth layer 306. The fifth layer 307 was formed to have a thickness of 50 nm and to have a mass ratio between Alq$_3$ and Li of 1:0.01. The fifth layer 307 serves as an electron injecting layer when operating a light-emitting element.

A second electrode 308 made from aluminum is formed over the fifth layer 307. The second electrode 308 is formed to have a thickness of 200 nm.

The light-emitting element manufactured as noted above emits light in the following procedure: current is flown when voltage is applied to the light-emitting element so that electric potential of the first electrode 302 is higher than that of the second electrode 308, and electrons and holes are recombined within the third layer 305 serving as a light-emitting layer to generate excited energy, then, excited Ir(MFpq)$_2$(acac) emits light while returning to the ground state.

The light-emitting element is sealed without exposing to the air under nitrogen atmosphere in a glove box. Then, operation characteristics of the light-emitting element are measured. The measurement is carried out at a room temperature (in the atmosphere kept at 25° C.).

Figure 32:
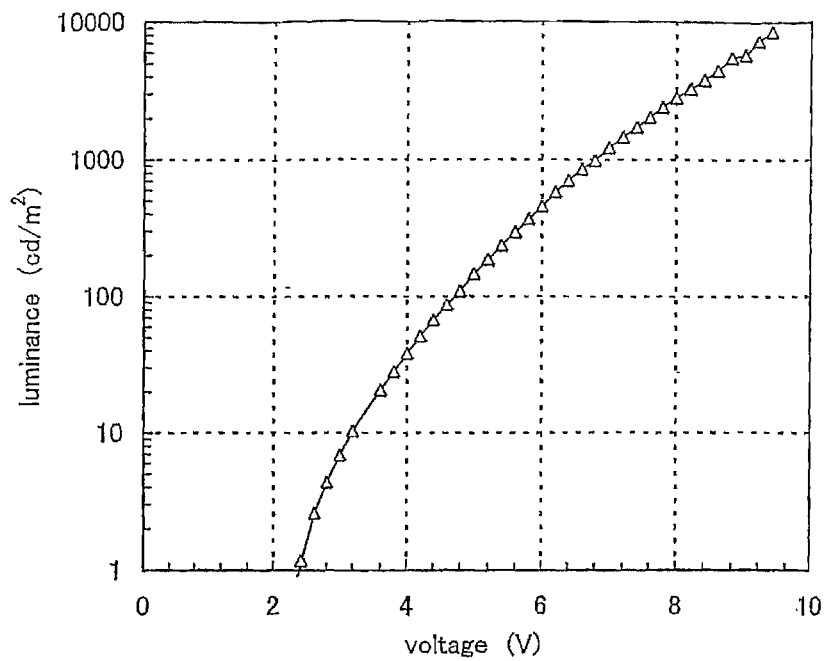
FIG. 32 is a view for showing a voltage-luminance characteristic of a light-emitting element according to Example 6.
Figure 33:
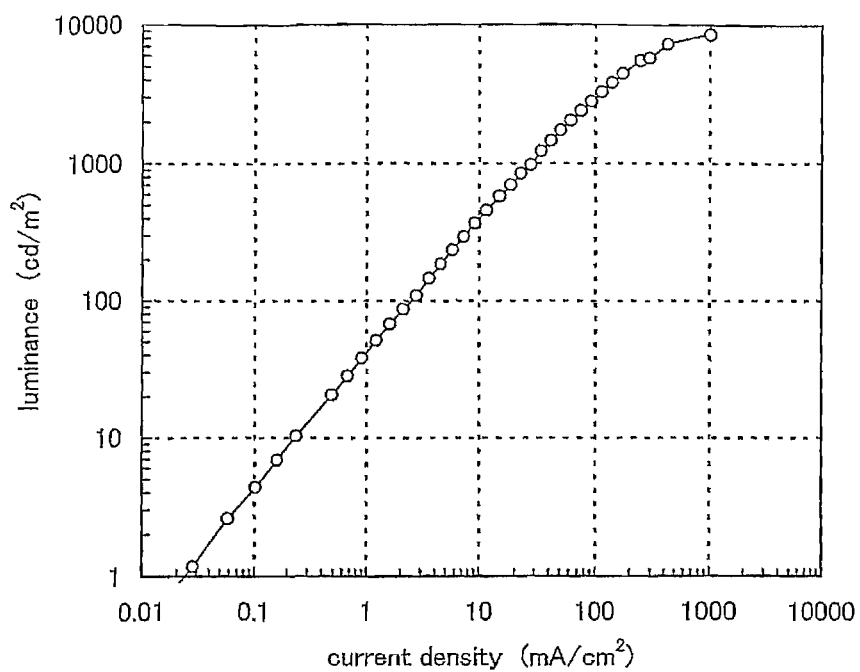
FIG. 33 is a view for showing a current density-luminance characteristic of a light-emitting element according to Example 6.
Figure 34:
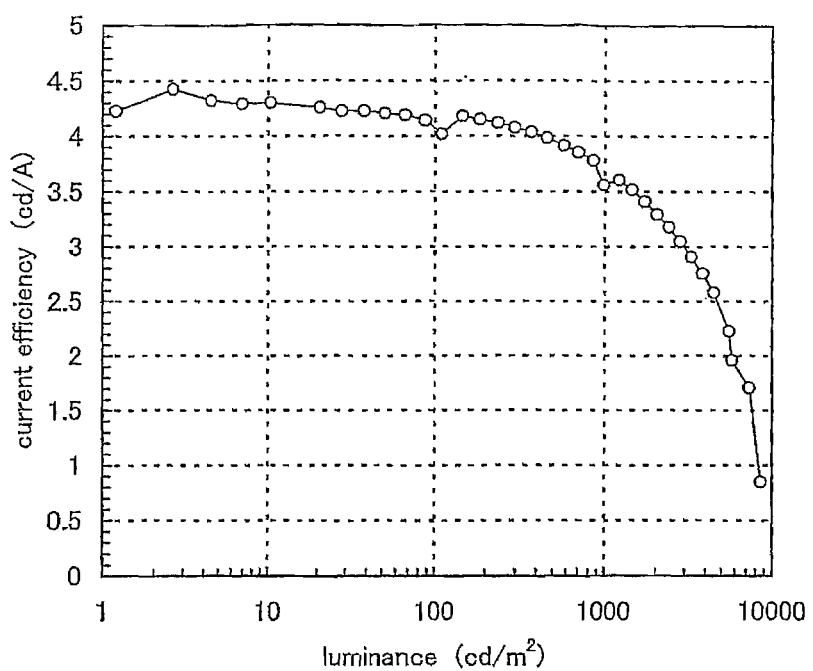
FIG. 34 is a view for showing a luminance-current efficiency characteristic of a light-emitting element according to Example 6.

FIGS. 32 to 34 are measurement results. FIG. 32 shows & measurement result of voltage-luminance characteristics, FIG. 33 shows a measurement result of current density-luminance characteristics, and FIG. 34 shows a measurement result of luminance-current efficiency characteristics. In FIG. 32, an abscissa axis represents voltage (V), whereas an ordinate axis represents luminance (cd/m$^2$). In FIG. 33, an abscissa axis represents current density (mA/cm$^2$), whereas an ordinate axis represents luminance (cd/m$^2$). In FIG. 34, an abscissa axis represents luminance (cd/m$^2$), whereas an ordinate axis represents current efficiency (cd/A). From these results, the light-emitting element according to this example emits light at current density of 27.6 mA/cm$^2$ and luminance of 980 cd/m$^2$ at an applied voltage of 6.8 V. The light-emitting element indicates good levels of current efficiency of 3.6 cd/A and external quantum efficiency of 5.0%.

Figure 35:
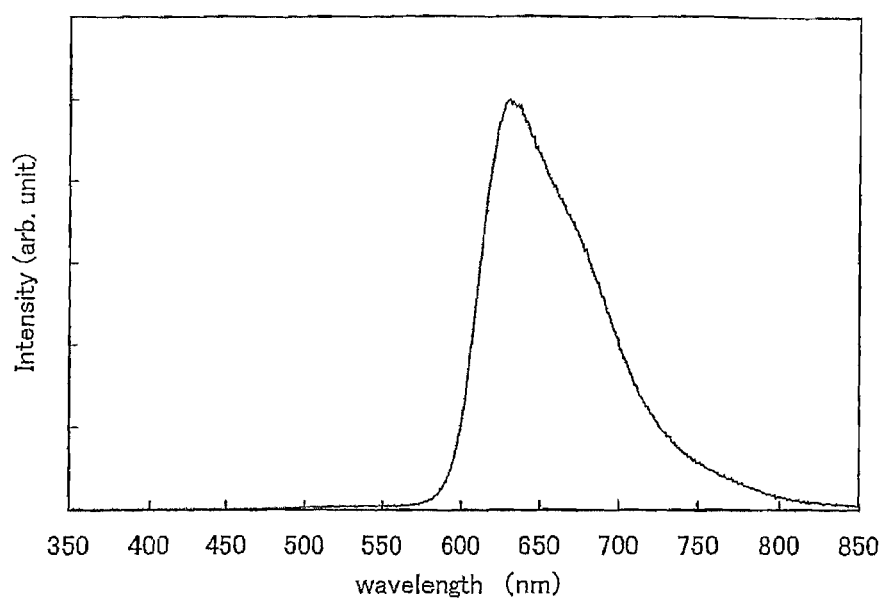
FIG. 35 is a view for showing an emission spectrum of a light-emitting element according to Example 6.

FIG. 35 shows an emission spectrum of the light-emitting element manufactured in this example. In FIG. 35, an abscissa axis represents a wavelength (nm), whereas an ordinate axis represents intensity (arbitrary unit). As shown in FIG. 35, the light-emitting element according to this example has a peak of the emission spectrum at 631 nm and exhibits light emission derived from Ir(MFpq)$_2$(acac) with the chromaticity coordinates x=0.68, y=0.31 in a CIE color coordinate system. Therefore, it can be known that the light-emitting element according to this example exhibits red light emission with good color purity.

Figure 36:
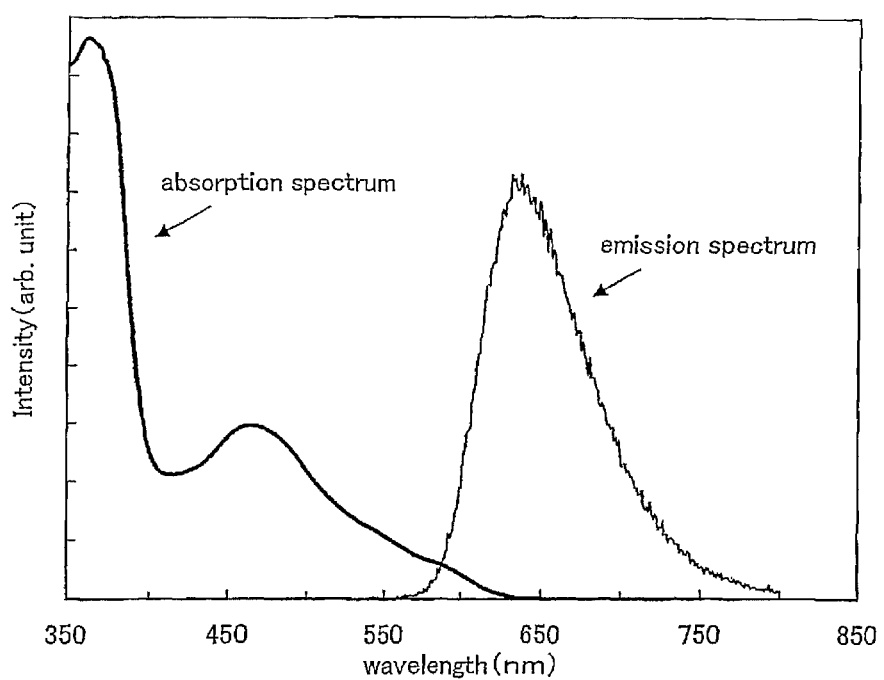
FIG. 36 is a view for showing changes in luminance with emission time of a light-emitting element according to Example 6.

The variation in luminance with light-emitting time (lifetime characteristic) of the light-emitting element manufactured according to this example is measured. The measurement was carried out in the way that current at a current value required for light emission at a luminance of 980 cd/m$^2$ is applied to the light-emitting element to achieve light emission and the luminance is measured at any given points in time. In FIG. 36, an abscissa axis represents light-emitting time (hour), whereas an ordinate axis represents relative values (no unit) against luminance at an initial state assuming that the luminance at the initial state is 100. As shown in FIG. 36, it can be predicted that a half-value period of the light-emitting element according to the present invention is approximate 10,000 hours. Therefore, the light-emitting element according to the present invention shows a favorable lifetime characteristic and has high reliability.

EXAMPLE 7

In this example, a manufacturing method and an operation characteristic of a light-emitting element employing Ir(MFpq)$_2$(acac) synthesized in Synthesis Example 2 as a light-emitting substance are explained with reference to FIGS. 13, 37 to 40.

As shown in FIG. 13, a first electrode 302 is formed by depositing indium tin oxide containing silicon oxide by a sputtering method over a glass substrate 301. The first electrode 302 is formed to have a thickness of 110 nm.

Then, the glass substrate 301 provided with the first electrode 302 is secured to a holder installed in a vacuum-deposition apparatus so that a face provided with the first electrode 302 of the glass substrate 301 is face down.

After reducing pressure in the vacuum-deposition apparatus to 1×10$^{-4}$ Pa, a first layer 303 is formed from DNTPD and molybdenum trioxide by co-evaporation over the first electrode 302. The first layer 303 is formed to have a thickness of 50 nm. The mass ratio between NBP and molybdenum trioxide is 4:2. The first layer 303 serves as a hole injecting layer when operating the light-emitting element.

Then, a second layer 304 is fowled from NPB by a vapor deposition method over the first layer 303. The second layer 304 is formed to have a thickness of 10 nm. The second layer 304 serves as a hole transporting layer when operating the light-emitting element.

And then, a third layer 305 containing TPAQn and Ir(MFpq)$_2$(acac) is formed by a co-evaporation method. The third layer 305 is formed to have a thickness of 30 nm and to have a mass ratio between TPAQn and Ir(MFpq)$_2$(acac) of 1:0.1. Therefore, Ir(MFpq)$_2$(acac) is contained in a layer having a matrix of TPAQn. The third layer 305 serves as a light-emitting layer when operating the light-emitting element. In that case, Ir(MFpq)$_2$(acac) is referred to as a guest, whereas TPAQn is referred to as a host.

A fourth layer 306 is formed from Alq$_3$ by a vapor deposition method over the third layer 305. The third layer 305 is formed to have a thickness of 10 nm. The third layer 305 serves as an electron transporting layer when operating the light-emitting element.

A fifth layer 307 containing Alq$_3$ and Li is formed by a co-evaporation method over a fourth layer 306. The fifth layer 307 was formed to have a thickness of 55 nm and to have a mass ratio between Alq$_3$ and Li of 1:0.01. The fifth layer 307 serves as an electron injecting layer when operating a light-emitting element.

A second electrode 308 made from aluminum is formed over the fifth layer 307. The second electrode 308 is formed to have a thickness of 200 nm.

The light-emitting element manufactured as noted above emits light in the following procedure: current is flown when voltage is applied to the light-emitting element so that electric potential of the first electrode 302 is higher than that of the second electrode 308, and electrons and holes are recombined within the third layer 305 serving as a light-emitting layer to generate excited energy, then, excited Ir(MFpq)$_2$(acac) emits light while returning to the ground state.

The light-emitting element is sealed without exposing to the air under nitrogen atmosphere in a glove box. Then, operation characteristics of the light-emitting element are measured. The measurement is carried out at a room temperature (in the atmosphere kept at 25° C.).

Figure 37:
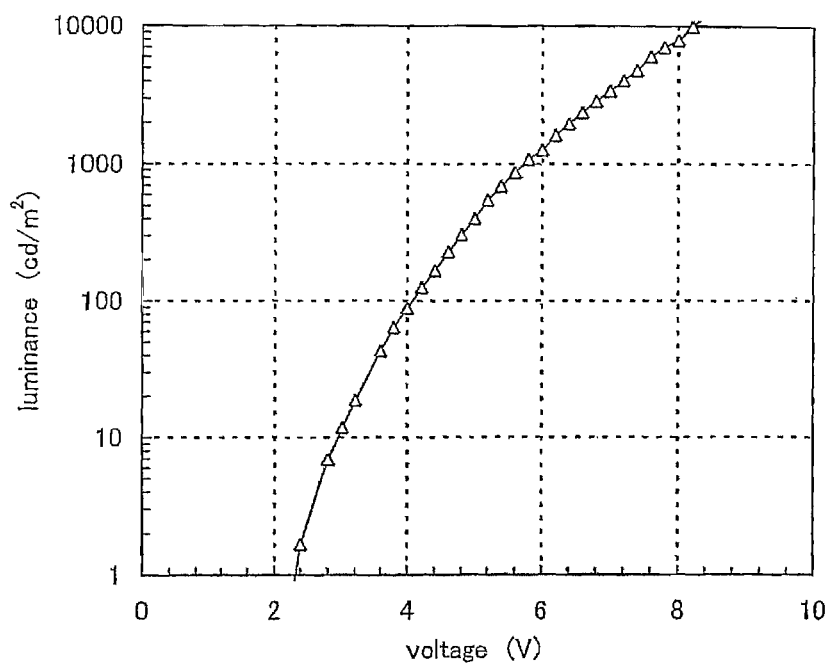
FIG. 37 is a view for showing a voltage-luminance characteristic of a light-emitting element according to Example 7.
Figure 38:
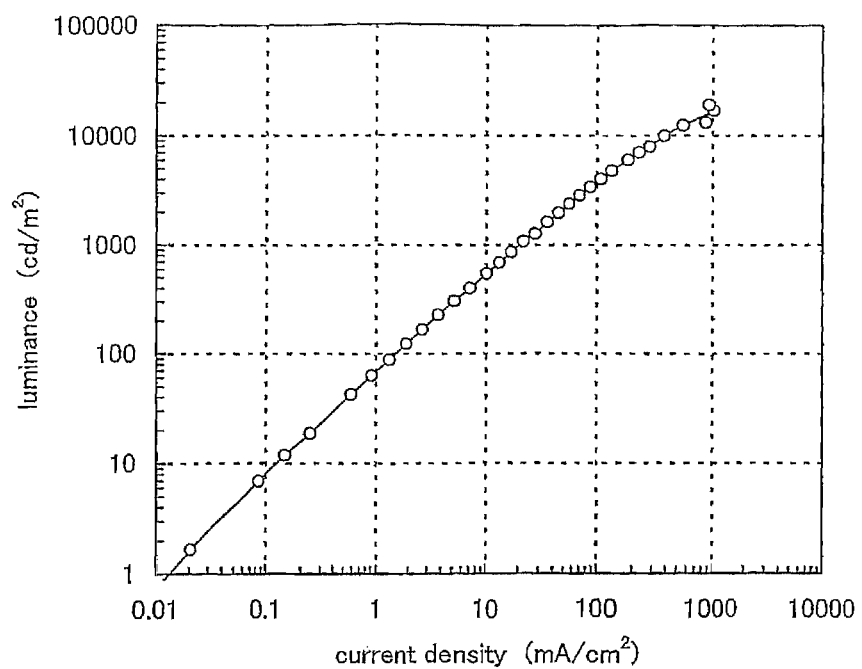
FIG. 38 is a view for showing a current density-luminance characteristic of a light-emitting element according to Example 7.
Figure 39:
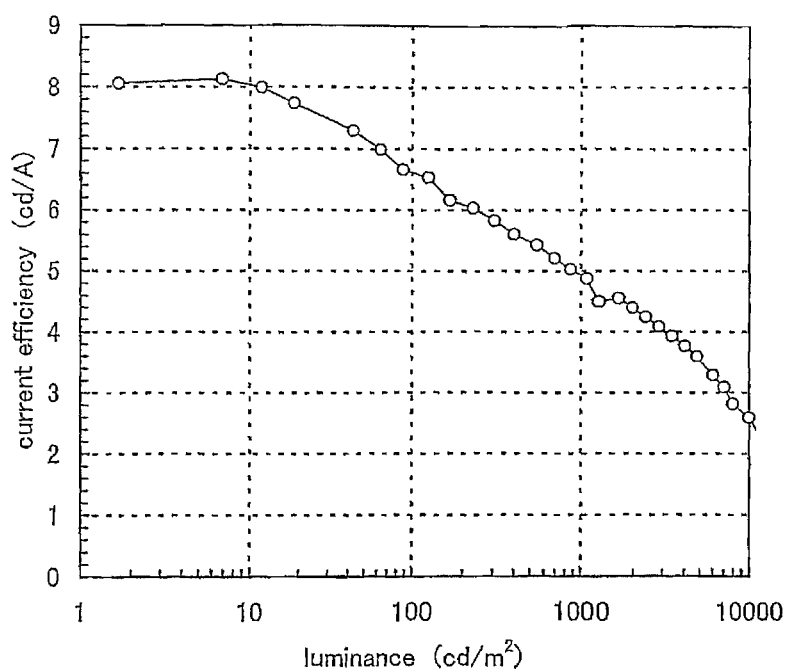
FIG. 39 is a view for showing a luminance-current efficiency characteristic of a light-emitting element according to Example 7.

FIGS. 37 to 39 are measurement results. FIG. 37 shows a measurement result of voltage-luminance characteristics, FIG. 38 shows a measurement result of current density-luminance characteristics, and FIG. 39 shows a measurement result of luminance-current efficiency characteristics. In FIG. 37, an abscissa axis represents voltage (V), whereas an ordinate axis represents luminance (cd/m$^2$). In FIG. 38, an abscissa axis represents current density (mA/cm$^2$), whereas an ordinate axis represents luminance (cd/m$^2$). In FIG. 39, an abscissa axis represents luminance (cd/m$^2$), whereas an ordinate axis represents current efficiency (cd/A). From these results, the light-emitting element according to this example emits light at current density of 22.2 mA/cm$^2$ and luminance of 1100 cd/m$^2$ at an applied voltage of 5.8 V. The light-emitting element indicates good levels of current efficiency of 4.9 cd/A and external quantum efficiency of 6.4%.

Figure 40:
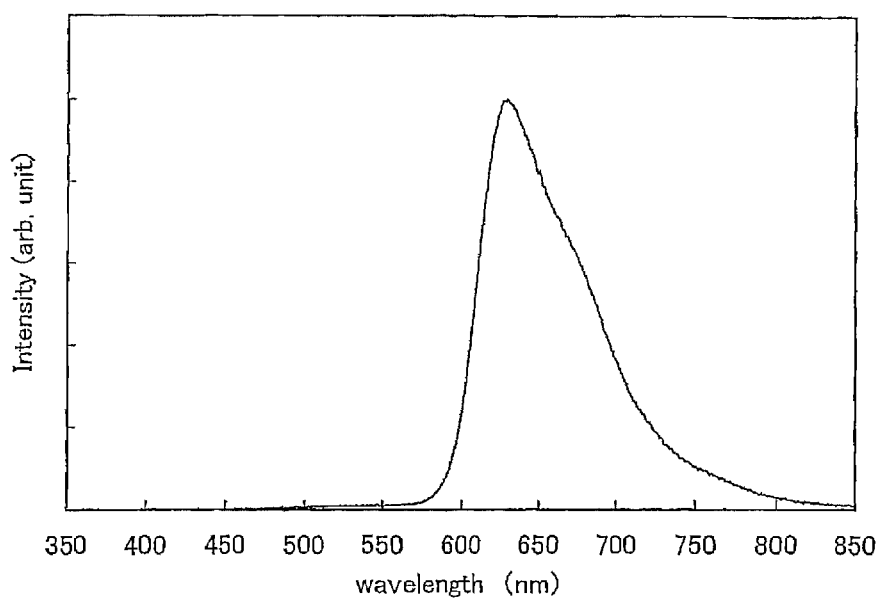
FIG. 40 is a view for showing an emission spectrum of a light-emitting element according to Example 7.

FIG. 40 shows an emission spectrum of the light-emitting element manufactured in this example. In FIG. 40, an abscissa axis represents a wavelength (nm), whereas an ordinate axis represents intensity (arbitrary unit). As shown in FIG. 40 the light-emitting element according to this example has a peak of the emission spectrum at 630 mu and exhibits light emission derived from Ir(MFpq)$_2$(acac) with the chromaticity coordinates x=0.68, y=0.32 in a CIE color coordinate system. Therefore, it can be known that the light-emitting element according to this example exhibits deep red light emission.

This application is based on Japanese Patent Application serial no. 2004-351770 filed in Japan Patent Office on 2004/12/03, the contents of which are hereby incorporated by reference.

Although the present invention has been fully described by way of examples with reference to the accompanying drawings, it is to be understood that various changes and modifications will be apparent to those skilled in the art. Therefore, unless otherwise such changes and modifications depart from the scope of the present invention hereinafter described, they should be construed as being included therein.

What is claimed is:

1. A light-emitting device comprising:
a first electrode;
a second electrode; and
a layer between the first electrode and the second electrode, the layer comprising an organometallic complex comprising a structure represented by a formula (3):

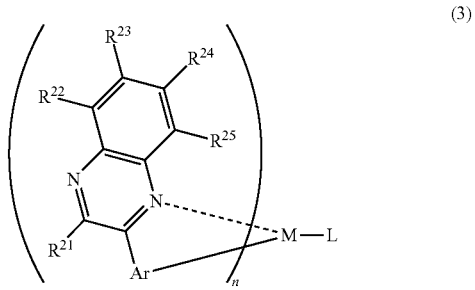

wherein $R^{21}$ represents an alkyl group having 1 to 4 carbon atoms; each of $R^{22}$ to $R^{25}$ represents any one of hydrogen, a halogen element, an acyl group, an alkyl group, an alkoxyl group, an aryl group, a cyano group, and a heterocyclic group; Ar represents an aryl group or a heterocyclic group; M represents a Group 9 element or a Group 10 element, in which n=2 when M represents a Group 9 element whereas n=1 when M represents a Group 10 element; and L represents a monoanionic ligand having a beta-diketone structure, a monoanionic bidentate chelate ligand having a carboxyl group, or a monoanionic bidentate chelate ligand having a phenolic hydroxyl group.

2. A light-emitting device comprising:
a first electrode;
a second electrode; and
a layer between the first electrode and the second electrode, the layer comprising an organometallic complex comprising a structure represented by a formula (4):

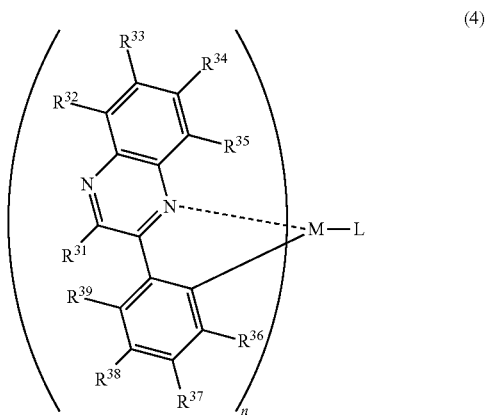

wherein $R^{31}$ represents an alkyl group having 1 to 4 carbon atoms; each of $R^{32}$ to $R^{35}$ represents any one of hydrogen, a halogen element, an acyl group, an alkyl group, an alkoxyl group, an aryl group, a cyano group, and a heterocyclic group; one of $R^{36}$ to $R^{39}$ represents an electron withdrawing group and each of the others represents any one of hydrogen, an acyl group, an alkyl group, an alkoxyl group, an aryl group, a heterocyclic group, and an electron withdrawing group; M represents a Group 9 element or a Group 10 element, in which n=2 when M represents a Group 9 element whereas n=1 when M represents a Group 10 element; and L represents a monoanionic ligand having a beta-diketone structure, a monoanionic bidentate chelate ligand having a carboxyl group, or a monoanionic bidentate chelate ligand having a phenolic hydroxyl group.

3. A light-emitting device comprising:
a first electrode;
a second electrode; and
a layer between the first electrode and the second electrode, the layer comprising an organometallic complex comprising a structure represented by a formula (3):

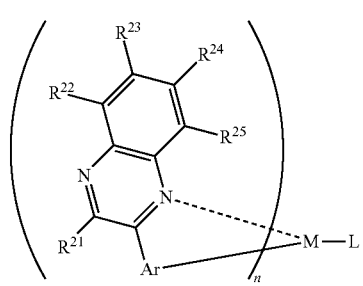

(3)

wherein $R^{21}$ represents an alkyl group having 1 to 4 carbon atoms; each of $R^{22}$ to $R^{25}$ represents hydrogen; Ar represents an aryl group; M represents a Group 9 element or a Group 10 element, in which n=2 when M represents a Group 9 element whereas n=1 when M represents a Group 10 element; and L represents a monoanionic ligand having a beta-diketone structure, a monoanionic bidentate chelate ligand having a carboxyl group, or a monoanionic bidentate chelate ligand having a phenolic hydroxyl group.

4. A light-emitting device comprising:
a first electrode;
a second electrode; and
a layer between the first electrode and the second electrode, the layer comprising an organometallic complex comprising a structure represented by a formula (4):

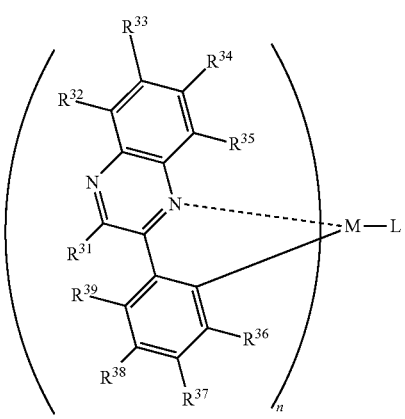

(4)

wherein $R^{31}$ represents an alkyl group having 1 to 4 carbon atoms; each of $R^{32}$ to $R^{35}$ represents hydrogen; each of $R^{36}$ to $R^{39}$ represents one of hydrogen and an electron withdrawing group; M represents a Group 9 element or a Group 10 element, in which n=2 when M represents a Group 9 element whereas n=1 when M represents a Group 10 element; and L represents a monoanionic ligand having a beta-diketone structure, a monoanionic bidentate chelate ligand having a carboxyl group, or a monoanionic bidentate chelate ligand having a phenolic hydroxyl group.

5. A light-emitting device comprising:
a first electrode;
a second electrode; and
a layer between the first electrode and the second electrode, the layer comprising an organometallic complex represented by any one of structural formulae 12 to 14:

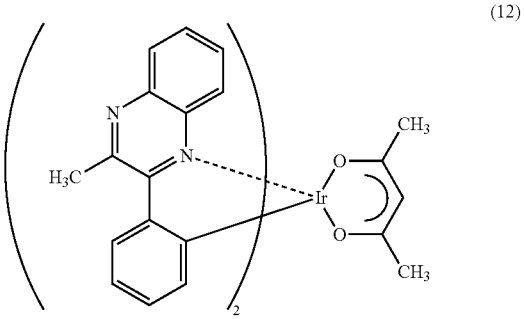

(12)

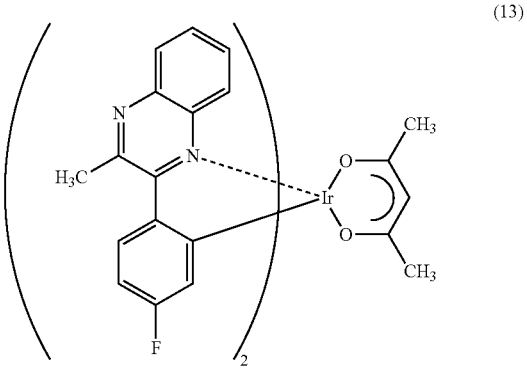

(13)

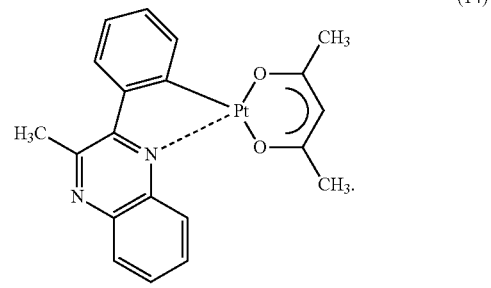

(14)

6. The light-emitting device according to claim 3, wherein L represents a monoanionic chelate ligand represented by any one of structural formulae 5 to 11:

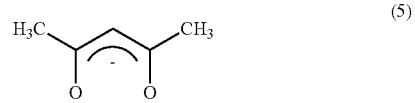

(5)

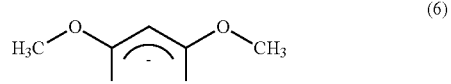

(6)

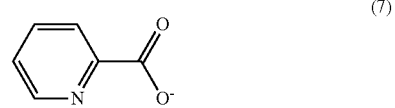

(7)

(8) 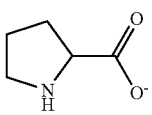

(9) 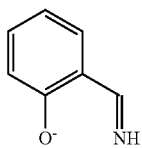

(10) 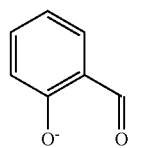

(11) 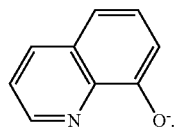

7. The light-emitting device according to claim 4, wherein L represents a monoanionic chelate ligand represented by any one of structural formulae 5 to 11:

(5) 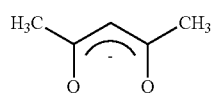

(6) 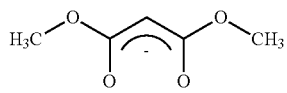

(7) 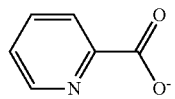

(8) 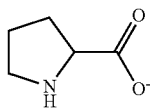

(9) 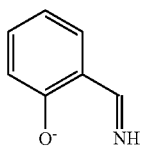

(10) 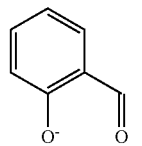

(11) 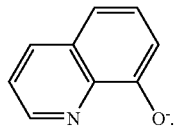

8. The light-emitting device according to claim 2, wherein the electron withdrawing group is a halogen element.

9. The light-emitting device according to claim 4, wherein the electron withdrawing group is a halogen element.

10. The light-emitting device according to claim 2, wherein the electron withdrawing group is a cyano group.

11. The light-emitting device according to claim 4, wherein the electron withdrawing group is a cyano group.

12. The light-emitting device according to claim 2, wherein the electron withdrawing group is a perfluorocarbon.

13. The light-emitting device according to claim 4, wherein the electron withdrawing group is a perfluorocarbon.

14. The light-emitting device according to claim 2, wherein the electron withdrawing group is a fluorine.

15. The light-emitting device according to claim 4, wherein the electron withdrawing group is a fluorine.

16. The light-emitting device according to claim 2, wherein the electron withdrawing group is a chlorine.

17. The light-emitting device according to claim 4, wherein the electron withdrawing group is a chlorine.

18. The light-emitting device according to claim 1,
wherein the layer further comprises a material having a ratio value of mobility of one of electrons and holes to the other of electrons and holes, and
wherein the ratio value is more than 100.

19. The light-emitting device according to claim 2,
wherein the layer further comprises a material having a ratio value of mobility of one of electrons and holes to the other of electrons and holes, and
wherein the ratio value is more than 100.

20. The light-emitting device according to claim 3,
wherein the layer further comprises a material having a ratio value of mobility of one of electrons and holes to the other of electrons and holes, and
wherein the ratio value is more than 100.

21. The light-emitting device according to claim 4,
wherein the layer further comprises a material having a ratio value of mobility of one of electrons and holes to the other of electrons and holes, and
wherein the ratio value is more than 100.

22. The light-emitting device according to claim 5,
wherein the layer further comprises a material having a ratio value of mobility of one of electrons and holes to the other of electrons and holes, and
wherein the ratio value is more than 100.

23. The light-emitting device according to claim 1, further comprising a hole transporting layer and an electron transporting layer between the first electrode and the second electrode,
wherein the layer is provided between the hole transporting layer and the electron transporting layer.

24. The light-emitting device according to claim 2, further comprising a hole transporting layer and an electron transporting layer between the first electrode and the second electrode,
wherein the layer is provided between the hole transporting layer and the electron transporting layer.

25. The light-emitting device according to claim 3, further comprising a hole transporting layer and an electron transporting layer between the first electrode and the second electrode,
wherein the layer is provided between the hole transporting layer and the electron transporting layer.

26. The light-emitting device according to claim 4, further comprising a hole transporting layer and an electron transporting layer between the first electrode and the second electrode,
wherein the layer is provided between the hole transporting layer and the electron transporting layer.

27. The light-emitting device according to claim 5, further comprising a hole transporting layer and an electron transporting layer between the first electrode and the second electrode,
wherein the layer is provided between the hole transporting layer and the electron transporting layer.

28. An electronic device including the light-emitting device according to claim 1 in a display portion of the electronic device, wherein the electronic device is selected from a television receiver, a telephone set, and a laptop computer.

29. An electronic device including the light-emitting device according to claim 2 in a display portion of the electronic device, wherein the electronic device is selected from a television receiver, a telephone set, and a laptop computer.

30. An electronic device including the light-emitting device according to claim 3 in a display portion of the electronic device, wherein the electronic device is selected from a television receiver, a telephone set, and a laptop computer.

31. An electronic device including the light-emitting device according to claim 4 in a display portion of the electronic device, wherein the electronic device is selected from a television receiver, a telephone set, and a laptop computer.

32. An electronic device including the light-emitting device according to claim 5 in a display portion of the electronic device, wherein the electronic device is selected from a television receiver, a telephone set, and a laptop computer.

* * * * *

UNITED STATES PATENT AND TRADEMARK OFFICE
CERTIFICATE OF CORRECTION

PATENT NO.       : 8,512,880 B2
APPLICATION NO.  : 12/878049
DATED            : August 20, 2013
INVENTOR(S)      : Hideko Inoue et al.

It is certified that error appears in the above-identified patent and that said Letters Patent is hereby corrected as shown below:

In the Specification

At column 1, line 10, "Light" should be --light--;

At column 20, line 60, "organoinetallic" should be --organometallic--;

At column 20, line 61, "Alternatively;" should be --Alternatively,--;

At column 22, line 11, "fowled" should be --formed--;

At column 22, line 39, "(4-tent-buthylphenyl)" should be --(4-tert-buthylphenyl)--;

At column 23, line 36, "fowls" should be --forms--;

At column 25, line 46, "9,10-di(2-naphtyl)-2-tent-buthylanthracene" should be --9,10-di(2-naphtyl)-2-tert-buthylanthracene--;

At column 26, line 21, "fowled" should be --formed--;

At column 31, line 53, "lumber)," should be --number),--;

At column 31, line 62, "is," should be --is--;

At column 33, line 20, "20 μm" should be --20nm--;

At column 33, line 58, "transistor n" should be --transistor 11--;

At column 34, line 51, "Material" should be --material--;

At column 34, line 61, "Second" should be --second--;

At column 37, line 36, "Used" should be --used--;

At column 39, line 66, "(MFpg)" should be --(MFpq)--;

At column 43, line 22, "fowled" should be --formed--;

At column 43, line 32, "She" should be --The--;

At column 43, line 34, "$Alg_a$" should be --$Alq_3$--;

At column 44, line 25, "fowled" should be --formed--;

At column 44, line 49, "$Alg_3$" should be --$Alq_3$--;

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,512,880 B2

At column 44, line 54, "$Alg_3$" should be --$Alq_3$--;

At column 46, line 14, "$Alg_a$" should be --$Alq_3$--;

At column 46, line 25, "$Alq_a$" should be --$Alq_3$--;

At column 47, line 31, "fowled" should be --formed--;

At column 47, line 65, "faulted" should be --formed--;

At column 49, line 44, "&" should be --a--;

At column 50, line 43, "fowled" should be --formed--; and

At column 51, line 41, "630 mu" should be --630 nm--.